(12) United States Patent
Burford et al.

(10) Patent No.: US 10,745,392 B2
(45) Date of Patent: Aug. 18, 2020

(54) BENZENESULFONAMIDE COMPOUNDS AND THEIR USE AS THERAPEUTIC AGENTS

(71) Applicant: Xenon Pharmaceuticals Inc., Burnaby (CA)

(72) Inventors: Kristen Nicole Burford, Burnaby (CA); Thilo Focken, Burnaby (CA); Verner Alexander Lofstrand, Burnaby (CA); Michael Scott Wilson, Burnaby (CA); Alla Yurevna Zenova, Vancouver (CA)

(73) Assignee: Xenon Pharmaceuticals Inc., Burnaby (CA)

( * ) Notice: Subject to any disclaimer, the term of this patent is extended or adjusted under 35 U.S.C. 154(b) by 0 days.

(21) Appl. No.: 16/440,459

(22) Filed: Jun. 13, 2019

(65) Prior Publication Data

US 2019/0382398 A1  Dec. 19, 2019

Related U.S. Application Data

(60) Provisional application No. 62/684,436, filed on Jun. 13, 2018.

(51) Int. Cl.
*C07D 417/12* (2006.01)
*A61P 25/08* (2006.01)
*C07D 277/52* (2006.01)
*C07D 413/12* (2006.01)

(52) U.S. Cl.
CPC ............ *C07D 417/12* (2013.01); *A61P 25/08* (2018.01); *C07D 277/52* (2013.01); *C07D 413/12* (2013.01)

(58) Field of Classification Search
CPC .............................. C07D 417/12; A61P 25/08
See application file for complete search history.

(56) References Cited

U.S. PATENT DOCUMENTS

| | | | |
|---|---|---|---|
| 3,845,770 A | 11/1974 | Theeuwes et al. | |
| 4,326,525 A | 4/1982 | Swanson et al. | |
| 5,877,193 A | 3/1999 | Cesura et al. | |
| 5,958,910 A | 9/1999 | Cesura et al. | |
| 8,222,281 B2 | 7/2012 | Toda et al. | |
| 9,481,677 B2 | 11/2016 | Liu et al. | |
| 9,630,929 B2 * | 4/2017 | Sun ...................... | C07D 401/12 |
| 10,246,453 B2 | 4/2019 | Andrez et al. | |
| 2009/0023740 A1 | 1/2009 | Fulp et al. | |
| 2010/0267782 A1 | 10/2010 | Beaudoin et al. | |
| 2014/0045862 A1 | 2/2014 | Shinozuka et al. | |
| 2014/0256736 A1 | 9/2014 | Liu et al. | |
| 2014/0315878 A1 | 10/2014 | Storer et al. | |
| 2014/0315933 A1 | 10/2014 | Owen et al. | |
| 2018/0162868 A1 | 6/2018 | Andrez et al. | |
| 2019/0194184 A1 | 6/2019 | Andrez et al. | |

FOREIGN PATENT DOCUMENTS

| | | |
|---|---|---|
| EP | 2 813 491 A1 | 12/2014 |
| WO | WO 98/50016 A2 | 11/1998 |
| WO | WO 00/42003 A1 | 7/2000 |
| WO | WO 01/05393 A2 | 1/2001 |
| WO | WO 01/40222 A1 | 6/2001 |
| WO | WO 03/076406 A1 | 9/2003 |
| WO | WO 2004/002481 A1 | 1/2004 |
| WO | WO 2005/021536 A2 | 3/2004 |
| WO | WO 2004/092123 A2 | 10/2004 |
| WO | WO 2005/000309 A2 | 1/2005 |
| WO | WO 2005/005421 A1 | 1/2005 |
| WO | WO 2005/013914 A2 | 2/2005 |
| WO | WO 2006/066109 A2 | 6/2006 |
| WO | WO 2006/129199 A1 | 12/2006 |
| WO | WO 2007/039171 A1 | 4/2007 |
| WO | WO 2007/075895 A2 | 7/2007 |
| WO | WO 2008/019967 A2 | 2/2008 |
| WO | WO 2008/051494 A1 | 5/2008 |
| WO | WO 2009/012242 A2 | 1/2009 |
| WO | WO 2009/013171 A2 | 1/2009 |
| WO | WO 2009/157418 A1 | 12/2009 |
| WO | WO 2010/002956 A2 | 1/2010 |
| WO | WO 2010/029300 A1 | 3/2010 |
| WO | WO 2010/079443 A1 | 7/2010 |
| WO | WO 2012/004743 A1 | 1/2012 |
| WO | WO 2012/022265 A1 | 2/2012 |
| WO | WO 2013/025883 A1 | 2/2013 |
| WO | WO 2013/063459 A1 | 5/2013 |
| WO | WO 2013/064983 A1 | 5/2013 |
| WO | WO 2013/122897 A1 | 8/2013 |
| WO | WO 2014/061970 A1 | 4/2014 |
| WO | WO 2014/066490 A1 | 5/2014 |
| WO | WO 2014/066491 A1 | 5/2014 |
| WO | WO 2014/170793 A1 | 10/2014 |
| WO | WO 2014/198849 A1 | 12/2014 |
| WO | WO 2014/201206 A1 | 12/2014 |
| WO | WO 2015/035278 A1 | 3/2015 |
| WO | WO 2015/038533 A2 | 3/2015 |
| WO | WO 2015/077905 A1 | 6/2015 |
| WO | WO 2015/080988 A1 | 6/2015 |
| WO | WO 2015/099841 A1 | 7/2015 |
| WO | WO 2016/177340 A1 | 11/2016 |
| WO | WO 2017/106409 A1 | 6/2017 |
| WO | WO 2017/201468 A1 | 11/2017 |
| WO | WO 2018/093694 A1 | 5/2018 |
| WO | WO 2018/106284 A1 | 6/2018 |

OTHER PUBLICATIONS

U.S. Appl. No. 16/555,983, filed Aug. 29, 2019, Andrez et al.
U.S. Appl. No. 16/556,055, filed Aug. 29, 2019, Andrez et al.
Barton et al., "Pharmacological characterization of the 6 Hz psychomotor seizure model of partial epilepsy," *Epilepsy Research* 47: 217-227, 2001.
Bean et al., "Lidocaine Block of Cardiac Sodium Channels," *J. Gen. Physiol.* 81: 613-642, May 1983.

(Continued)

*Primary Examiner* — Golam M Shameem
(74) *Attorney, Agent, or Firm* — Fish & Richardson P.C.

(57) ABSTRACT

This invention is directed to benzenesulfonamide compounds, as stereoisomers, enantiomers, tautomers thereof or mixtures thereof; or pharmaceutically acceptable salts, solvates or prodrugs thereof, for the treatment of diseases or conditions associated with voltage-gated sodium channels, such as epilepsy and/or epileptic seizure disorders.

47 Claims, No Drawings

(56) References Cited

OTHER PUBLICATIONS

Boerma et al., "Remarkable Phenytoin Sensitivity in 4 Children with SCN8A-related Epilepsy: A Molecular Neuropharmacological Approach," *Neurotherapeutics* 13: 192-197, 2016.
Bordwell et al., "The Reduction of Sulfones to Sulfides," *JACS* 73: 2251-2253, May 1951.
Burgess et al., "Mutation of a new sodium channel gene, Scn8a, in the mouse mutant 'motor endplate disease'," *Nature Genetics* 10: 461-465, Aug. 1995.
Carroll et al., "Mutation screening of SCN2A in schizophrenia and identification of a novel loss-of-function mutation," *Psychiatr. Genet.* 26: 60-65, 2016.
Catterall, "Sodium Channels, Inherited Epilepsy, and Antiepileptic Drugs," *Annu. Rev. Pharmacol. Toxicol.* 54: 317-338, 2014.
Cestéle et al., "Molecular mechanisms of neurotoxin action on voltage-gated sodium channels," *Biochimie* 82: 883-892, 2000.
Cheah et al., "Correlations in timing of sodium channel expression, epilepsy, and sudden death in Dravet syndrome," *Channels* 7(6): 468-472, Nov./Dec. 2013.
Cojocariu et al., "Sinteza unor $N^4$-(2-hidroxi-4-clorbenzoil)-sulfamide cu activitate antimicotica potentiala," *Revista de Chimie* 30(12): C-1261, 1979 (3 pages).
De Kovel et al., "Characterization of a de novo SCN8A mutation in a patient with epileptic encephalopathy," *Epilepsy Research* 108: 1511-1518, 2014.
Dravet et al., *Handbook of Clinical Neurology, vol. 111 ($3^{rd}$ series)—Pediatric Neurology Part 1*, Elsevier B.V., Amsterdam, Netherlands, 2013, Chapter 65, "Dravet syndrome (severe myoclonic epilepsy in infancy)," pp. 627-633.
Dutton et al., "Preferential inactivation of Scn1a in parvalbumin interneurons increases seizure susceptibility," *Neurobiology of Disease* 49: 211-220, 2013.
Estacion et al., "A novel de novo mutation of SCN8A ($Na_v1.6$) with enhanced channel activation in a child with epileptic encephalopathy," *Neurobiology of Disease* 69: 117-123, 2014.
Focken et al., "Discovery of Aryl Sulfonamides as Isoform-Selective Inhibitors of Nav1.7 with Efficacy in Rodent Pain Models," *ACS Med.Chem. Lett.* 7: 277-282, 2016.
Fukasawa et al., "A case of recurrent encephalopathy with SCN2A missense mutation," *Brain & Development* 37: 631-634, 2015.
Gardner et al., "A Facile Reduction of Sulfones to Sulfides," *Can. J. Chem.* 51: 1419-1421, 1973.
Hadži et al., "The Role of Hydrogen Bonding in Drug-Receptor Interactions," *Journal of Molecular Structure* 237: 139-150, 1990.
Hawkins et al., Hlf is a genetic modifier of epilepsy caused by voltage-gated sodium channel mutations, *Epilepsy Research* 119: 20-23, 2016.
Hawkins et al., "Neuronal voltage-gated ion channels are genetic modifiers of generalized epilepsy with febrile seizures plus," *Neurobiology of Disease* 41: 655-660, 2011.
Helbig, "Genetic Causes of Generalized Epilepsies," *Semin. Neurol.* 35: 288-292, 2015.
Hille, "Local Anesthetics: Hydrophilic and Hydrophobic Pathways for the Drug-Receptor Reaction," *The Journal of General Physiology* 69: 497-515, 1977.
Hitchcock et al., "Perspective: Structure—Brain Exposure Relationships," *Journal of Medicinal Chemistry* 49(26): 7559-7583, Dec. 28, 2006.
Hossfeld, "Paper Partition Chromatography of Simple Phenols," *J. Am. Chem. Soc.* 73: 852-854, 1951.
Howell et al., "SCN2A encephalopathy: A major cause of epilepsy of infancy with migrating focal seizures," *Neurology* 85: 958-966, 2015.
Hu et al., "Distinct contributions of $NA_v1.6$ and $Na_v1.2$ in action potential initiation and backpropagation," *Nature Neuroscience* 12(8): 996-1002, Aug. 2009 (9 pages).
James et al., "A modular, gold-catalysed approach to the synthesis of lead-like piperazine scaffolds," *Org. Lett.* 15(23): 6094-6097, 2013.
Kearney et al., "A Gain-of-Function Mutation in the Sodium Channel Gene Scn2a Results in Seizures and Behavioral Abnormalities," *Neuroscience* 102(2): 307-317, 2001.
Kong et al., "SCN8A mutations in Chinese children with early onset epilepsy and intellectual disability," *Epilepsia* 56(3): 431-438, 2015.
Kuzma et al., "Progress in the Development of Ultra-Long-Acting Local Anesthetics," *Regional Anesthesia* 22(6): 543-551, 1997.
Larsen et al., "The phenotypic spectrum of SCN8A encephalopathy," *Neurology* 84: 480-489, 2015.
Leuwer et al., "An improved model for the binding of lidocaine and structurally related local anaesthetics to fast-inactivated voltage-operated sodium channels, showing evidence of cooperativity," *British Journal of Pharmacology* 141: 47-54, 2004.
Liu et al., "Mutations in Cardiac Sodium Channels: Clinical Implications," *Am. J. Pharmacogenomics* 3(3): 173-179, 2003.
Löscher et al., "Which animal models should be used in the search for new antiepileptic drugs? A proposal based on experimental and clinical considerations," *Epilepsy Res.* 2: 145-181, 1988.
Luci et al., "Synthesis and Structure—Activity Relationship Studies of 4-((2-Hydroxy-3-methoxybenzyl)amino)benzenesulfonamide Derivatives as Potent and Selective Inhibitors of 12-Lipoxygenase,"*J. Med. Chem.* 57: 495-506, 2014.
Makinson et al., "An Scn1a epilepsy mutation in Scn8a alters seizure susceptibility and behavior," *Experimental Neurology.* 275: 46-58, 2016.
Makinson et al., "Role of the hippocampus in $Na_v1.6$ (Scn8a) mediated seizure resistance," *Neurobiology of Disease* 68: 16-25, 2014.
Martin et al., "The voltage-gated sodium channel Scn8a is a genetic modifier of severe myoclonic epilepsy of infancy," *Human Molecular Genetics* 16(23): 2892-2899, 2007.
Martin et al., "Altered Function of the SCN1A Voltage-gated Sodium Channel Leads to γ-Aminobutyiic Acid-ergic (GABAergic) Interneuron Abnormalities," *The Journal of Biological Chemisty* 285(13): 9823-9834, Mar. 26, 2010.
Massey et al., "Mechanisms of sudden unexpected death in epilepsy: the pathway to prevention," *Nature Reviews Neurology* 10: 271-282, May 2014.
Matsukawa et al., "Studies on Chemotherapeutics. XII. Syntheses of p-Hydroxybenezenesulfonamide Derivatives," *Yakugaku Zasshi* 70(10): 557-561, 1950.
McKusik et al., Epileptic Encephalopathy, Early Infantile 6, EIEE6, Online Mendelian Inheritance in Man: John Hopkins University, 2012, 12 pages, URL=http:omin.org/entry/607208, download date Sep. 6, 2017.
Miller et al., "Mapping genetic modifiers of survival in a mouse model of Dravet syndrome," *Genes, Brain and Behavior* 13: 163-172, 2014.
Mistry et al., "Strain- and age-dependent hippocampal neuron sodium currents correlate with epilepsy severity in Dravet syndrome mice," *Neurobiology of Disease* 65: 1-11, 2014.
Norinder et al., "QSAR investigation of NaV1.7 active compounds using the SVM/Signature approach and the Bioclipse Modeling platform," *Bioorganic & Medicinal Chemistry Letters* 23: 261-263, 2013.
Ogiwara et al., "$Na_v1.1$ Localizes to Axons of Parvalbumin-Positive Inhibitory Interneurons: A Circuit Basis for Epileptic Seizures in Mice Carrying an Scn1a Gene Mutation," *The Journal of Neuroscience* 27(22): 5903-5914, May 30, 2007.
Ohba et al., "Early onset epileptic encephalopathy caused by de novo Scn8A mutations," *Epilepsia* 55(7): 994-1000, 2014.
Patani et al., "Bioisosterism: A Rational Approach in Drug Design," *Chem. Rev.* 96: 3147-3176, 1996.
Payne et al., "Identification of KD5170: A novel mercaptoketone-based histone deacetylase inhibitor," *Bioorganic & Medicinal Chemistry Letters* 18: 6093-6096, 2008.
Piredda et al., "Effect of Stimulus Intensity on the Profile of Anticonvulsant Activity of Phenytoin, Ethosuximide and Valproate," *The Journal of Pharmacology and Experimental Therapeutics* 232(3): 741-745, 1985.
Prasanthy et al., "Synthesis and Biological Evaluation of 1-Substituted Imidazole Derivatives," *Int. J Pharma* 1(2): 92-99, 2011.

(56) References Cited

OTHER PUBLICATIONS

Raymond et al., "Expression of Alternatively Spliced Sodium Channel α-Subunit Genes," *Journal of Biological Chemistry* 279(44): 46234-46241, Oct. 29, 2004.
Rogers et al., "Characterization of Endogenous Sodium Channels in the ND7-23 Neuroblastoma Cell Line: Implications for Use as a Heterologous Ion Channel Expression System Suitable for Automated Patch Clamp Screening," *Assay and Drug Development Technologies* 14(2): 109-130, Mar. 2016.
Royeck et al., "Role of Axonal $Na_v1.6$ Sodium Channels in Action Potential Initiation of CA1 Pyramidal Neurons," *J. Neurophysiol.* 100: 2361-2380, 2008.
Saitoh et al., "Missense mutations in sodium channel SCN1A and SCN2A predispose children to encephalopathy with severe febrile seizures," *Epilepsy Research* 117: 1-6, 2015.
Samanta et al., "De novo R853Q mutation of SCN2A gene and West syndrome," *Acta Neurol. Belg.* 115: 773-776, 2015.
Schwarz et al., "Mutations in the sodium channel gene SCN2A cause neonatal epilepsy with late-onset episodic ataxia," *J. Neurol.* 263: 334-343, 2016.
Stumpf et al., "Development of an Expedient Process for the Multi-Kilogram Synthesis of Chk1 Inhibitor GDC-0425," *Org. Process Res. Dev.* 19: 661-672, 2015.
Suzuki et al., "Morphogenetic Effect of Kainate on Adult Hippocampal Neurons Associated with a Prolonged Expression of Brain-derived Neurotrophic Factor," *Neuroscience* 64(3): 665-674, 1995.
Toman et al., "Properties of Maximal Seizures, and Their Alteration by Anticonvulsant Drugs and Other Agents," *J. Neurophysiol.* 9: 231-239, 1946.
Trudeau et al., "Heterozygosity for a protein truncation mutation of sodium channel SCN8A in a patient with cerebellar atrophy, ataxia, and mental retardation," *J. Med. Genet.* 43: 527-530, 2006.
Tuncer et al., "A clinical variant in SCN1A inherited from a mosaic father cosegregates with a novel variant to cause Dravet syndrome in a consanguineous family," *Epilepsy Research* 113: 5-10, 2015.
Vaher et al., "De Novo SCN8A Mutation Identified by Whole-Exome Sequencing in a Boy With Neonatal Epileptic Encephalopathy, Multiple Congenital Anomalies, and Movement Disorders," *Journal of Child Neurology* 29(12): NP202-NP206, 2014.
Veeramah et al., "De Novo Pathogenic SCN8A Mutation Identified by Whole-Genome Sequencing of a Family Quartet Affected by Infantile Epileptic Encephalopathy and SUDEP," *The American Journal of Human Genetics* 90: 502-510, Mar. 9, 2012.
Vega et al., "Reduced expression of $Na_v1.6$ sodium channels and compensation of $Na_v1.2$ channels in mice heterozygous for a null mutation in Scn8a," *Neuroscience Letters* 442: 69-73, 2008.
Wagnon et al., "Convulsive seizures and SUDEP in a mouse model of SCN8A epileptic encephalopathy," *Human Molecular Genetics* 24(2): 506-515, 2015.
Ward, "Chiral Separations," *Anal. Chem.* 74: 2863-2872, 2002.
White et al., "The early identification of anticonvulsant activity: role of the maximal electroshock and subcutaneous pentylenetetrazol seizure models," *Ital. J. Neurol. Sci* 16: 73-77, 1995.
Wilmshurst et al., Summary of recommendations for the management of infantile seizures: Task Force Report for the ILAE Commission of Pediatrics, *Epilepsia* 56(8): 1185-1197, 2015.
Wu et al., "Development of New Benzenesulfonamides As Potent and Selective $Na_v1.7$ Inhibitors for the Treatment of Pain," *J. Med. Chem.* 60: 2513-2525, 2017.
Yu et al., "Reduced sodium current in GABAergic interneurons in a mouse model of severe myoclonic epilepsy in infancy," *Nature Neuroscience* 9(9): 1142-1149, Sep. 2006.
Zerem et al., "Paternal germline mosaicism of a SCN2A mutation results in Ohtahara syndrome in half siblings," *European Journal of Paediatric Neurology* 18: 567-571, 2014.
International Search Report and Written Opinion, dated Sep. 25, 2017, for International Application No. PCT/US2017/033666, 30 pages.
International Preliminary Report on Patentability, dated Jun. 20, 2019, for International Application No. PCT/US2017/033666, 20 pages.
International Search Report and Written Opinion, dated Jul. 4, 2017, for International Application No. PCT/US2017/033634, 13 pages.
International Preliminary Report on Patentability, dated Nov. 20, 2018, for International Application No. PCT/US2017/033634, 7 pages.
International Search Report and Written Opinion, dated Sep. 11, 2019, for International Application No. PCT/US2019/037011, 13 pages.

\* cited by examiner

BENZENESULFONAMIDE COMPOUNDS AND THEIR USE AS THERAPEUTIC AGENTS

CROSS-REFERENCE TO RELATED APPLICATION

This application claims the benefit under 35 U.S.C. § 119(e) of U.S. Provisional Patent Application No. 62/684,436, filed Jun. 13, 2018, which is incorporated herein by reference in its entirety.

FIELD OF THE INVENTION

The present invention is directed to benzenesulfonamide compounds and pharmaceutical compositions comprising the compounds and methods of using the compounds and the pharmaceutical compositions in treating sodium channel-mediated diseases or conditions, such as epilepsy and/or epileptic seizure disorder, as well as other diseases and conditions associated with the mediation of sodium channels.

BACKGROUND OF THE INVENTION

Voltage gated sodium channels ($Na_V$'s) are critical determinants of cellular excitability in muscle and nerve (Hille, B, *Ion Channels of Excitable Membranes* (2001), Sunderland, Mass., Sinauer Associates, Inc.). Four isoforms in particular, $Na_V1.1$, $Na_V1.2$, $Na_V1.3$, and $Na_V1.6$, account for the majority of sodium current in the neurons of the central nervous system. $Na_V1.3$ is primarily expressed embryonically. Beyond the neonatal stage, $Na_V1.1$, $Na_V1.2$, and $Na_V1.6$ are the critical isoforms that regulate neuronal signaling in the brain (Catterall, W. A., *Annual Review of Pharmacology and Toxicology* (2014), Vol. 54, pp. 317-338).

$Na_V1.5$ is expressed mainly in cardiac myocytes (Raymond, C. K. et al., *J. Biol. Chem.* (2004), Vol. 279, No. 44, pp. 46234-41), including atria, ventricles, the sino-atrial node, atrio-ventricular node and cardiac Purkinje fibers. Mutations in human $Na_V1.5$ result in multiple arrhythmic syndromes, including, for example, long QT3 (LQT3), Brugada syndrome (BS), an inherited cardiac conduction defect, sudden unexpected nocturnal death syndrome (SUNDS) and sudden infant death syndrome (SIDS) (Liu, H., et al., *Am. J. Pharmacogenomics* (2003), Vol. 3, No. 3, pp. 173-9). Sodium channel blocker therapy has been used extensively in treating cardiac arrhythmias.

Epilepsy is a condition characterized by excessive synchronous excitability in the brain that arises when the delicate balance of excitatory and inhibitory signals in the brain fall out of equilibrium. This can happen either due to an excess of excitation, or a deficiency of inhibition. Mutations in the genes encoding $Na_V$ channels have been linked to both types of disequilibrium.

$Na_V1.1$ has been identified as the primary $Na_V$ isoform of inhibitory interneurons (Yu, F. H. et al., *Nat. Neurosci.* (2006), Vol. 9, pp. 1142-1149). These interneurons synapse on many other neurons, including excitatory glutamatergic neurons. Action potentials in the interneurons induce the release of the neurotransmitter GABA onto other neurons, hyperpolarizing them and thus dampening excitation. This results in a negative feedback that enables controlled signaling and prevents local signals from expanding into waves of excitation that spread across large brain regions. Because of this critical role in inhibitory interneurons, mutations that impair $Na_V1.1$ channel function can lead to a failure of those neurons to activate and release GABA (Ogiwara, I. et al., *J. Neurosci.* (2007), Vol. 27, pp. 5903-5914; Martin, M. S. et al., *J. Biol. Chem.* (2010), Vol. 285, pp. 9823-9834; Cheah, C. S. et al., *Channels (Austin)* (2013), Vol. 7, pp. 468-472; and Dutton, S. B., et al., (2013), Vol. 49, pp. 211-220). The result is a loss in the inhibitory tone of the brain and a failure to contain the excitability of the glutamatergic neurons. This failure of the inhibitory interneurons can result in aberrant wide-scale synchronous firing of neurons across regions of the brain (epilepsy).

Mutations in the gene encoding $Na_V1.1$ (SCN1A) fall into two broad classes, those that cause generalized epilepsy with febrile seizures plus (GEFS+) and those that cause severe myoclonic epilepsy of infancy (SMEI), also known as Dravet Syndrome or early infantile epileptic encephalopathy 6 (EIEE6) (McKusik, V. K. et al., *A Epileptic Encephalopathy, Early Infantile 6, EIEE6* (2012), Online Mendelian Inheritance in Man: John Hopkins University). SMEI mutations are heterozygous autosomal dominant mutations and are often caused by a gene deletion or truncation that leads to a channel with little or no function. The mutations arise de novo, or in a few cases have been shown to arise in asymptomatic mosaic parents (Tuncer, F. N. et al., *Epilepsy Research* (2015), Vol. 113, pp. 5-10). Patients are born phenotypically normal and meet developmental milestones until the onset of seizures, typically between the age of 6 months and 1 year. This time of onset is believed to be a consequence of the normal decrease in the expression of the embryonic isoform $Na_V1.3$ and the coincident rise of $Na_V1.1$. When the $Na_V1.1$ channels fail to reach normal levels, the phenotype is revealed (Cheah, C. S. et al., *Channels (Austin)* (2013), Vol. 7, pp. 468-472). The initial seizure is often triggered by a febrile episode and can manifest as status epilepticus. Seizures continue and increase in frequency and severity for the first several years of life and can reach frequencies of over 100 episodes per day. Seizures may be triggered by fever or may arise spontaneously without apparent cause. After seizure onset patients begin to miss developmental milestones and significant cognitive and behavioral deficits accrue (Dravet, C. and Oguni, H., *Handbook of Clinical Neurology* (2013), Vol. 111, pp. 627-633). 80 to 85% of phenotypically diagnosed Dravet syndrome patients are believed to have a responsible mutation in SCN1A, while the other 15-20% of patients have other mutations or are of unknown etiology. There is a high rate of sudden unexplained death in epilepsy (SUDEP) in SMEI patients, with an estimated 37% of patients dying by SUDEP, but the mechanism for this catastrophic outcome remains unclear (Massey, C. A., et al., *Nature Reviews Neurology* (2014), Vol. 10, pp. 271-282). Clinically useful anti-epileptic drugs that target voltage-gated sodium channels non-selectively, like carbamazepine and phenytoin, are contra-indicated for SMEI patients as they can exacerbate seizures in these patients (Wlmshurst, J. M. et al., *Epilepsia* (2015), Vol. 56, pp. 1185-1197). This is presumed to be because patients cannot tolerate further reductions in $Na_V1.1$ function.

GEFS+ is often caused by missense SCN1A mutations that induce relatively mild channel dysfunction, consistent with the relatively milder seizure phenotype. A large and growing number of mutations have been identified, and both the severity and the penetrance of the phenotype varies considerably. Many GEFS+ patients outgrow the seizure phenotype, however not all do, and GEFS+ patients with childhood epilepsy are considerably more prone to have epilepsy as adults than are the general population. Mutations that cause deficits in other genes involved with GABA-ergic signaling, like SCN1B that encodes the sodium channel auxiliary subunit and GABRG2 that encodes a subunit of $GABA_A$ receptors can also give rise to GEFS+ (Helbig, I., Seminars in *Neurology* (2015) Vol. 35, pp. 288-292).

Transgenic mice have been developed that harbor the same mutations identified in SMEI and GEFS+ patients. In both cases the mice replicate the human phenotype well, though the penetrance of the phenotype can be significantly impacted by the genetic background. Some mouse strains tolerate the mutations relatively well, while in other strains the same mutations can cause drastic seizure phenotypes. These differences are presumed to be due to differing levels of expression of other genes that modulate the excitation phenotype (Miller, A. R. et al., *Genes, Brain, and Behavior* (2014), Vol. 13, pp. 163-172; Mistry, A. M. et al., *Neurobiology of Disease* (2014), Vol. 65, pp. 1-11; and Hawkins, N. A. et al., *Epilepsy Research* (2016), Vol. 119, pp. 20-23).

In the brain, $Na_V1.2$ and $Na_V1.6$ are primarily expressed in excitatory glutamatergic neurons. Both channels are especially dense in the action initial segment (AIS), a region of the neuron adjacent to the neuronal soma that acts to integrate inputs and initiates action potential propagation to the soma and the distal dendrites (Royeck, M. et al., *J. Neurophysiol.* (2008), Vol. 100, pp. 2361-2380; Vega, A. V. et al., *Neurosci. Lett.* (2008), Vol. 442, pp. 69-73; and Hu, W. et al., *Nat. Neurosci.* (2009), Vol. 12, pp. 996-1002). $Na_V1.6$ tends to be especially densely localized the early AIS (distal from the soma) where it is thought to act to trigger action potential initiation. $Na_V1.2$ is more highly localized to the segment of the AIS most proximal to the soma. Mutations in both SCN2A ($Na_V1.2$) and SCN8A ($Na_V1.6$) have been linked to epilepsy and cognitive delay. The effects of the mutations are diverse both at the level of the impact on channel function, and on the patient phenotype. Both $Na_V1.2$ and $Na_V1.6$ are also expressed in peripheral neurons. $Na_V1.6$ is especially dense at the nodes of Ranvier of myelinated neurons, where it is critical for maintaining salutatory conduction and high speed neuronal signaling.

Only a handful of $Na_V1.2$ mutations have been described, but they are primarily linked with central nervous system pathologies, especially epilepsy (Kearney, J. A. et al., *Neuroscience* (2001), Vol. 102, pp. 307-317; Zerem, A. et al., *European Journal of Paediatric Neurology: EJPN: Official Journal of the European Paediatric Neurology Society* (2014), Vol. 18, pp. 567-571; Fukasawa, T. et al., *Brain & Development* (2015), Vol. 37, pp. 631-634; Howell, K. B. et al., *Neurology* (2015), Vol. 85, pp. 958-966; Saitoh, M. et al., *Epilepsy Research* (2015), Vol. 117, pp. 1-6; Samanta, D. et al., *Acta Neurologica Belgica* (2015), Vol. 115, pp. 773-776; Carroll, L. S. et al., *Psychiatric Genetics* (2016), Vol. 26, pp. 60-65; and Schwarz, N. et al., *Journal of Neurology* (2016), Vol. 263, pp. 334-343). The epilepsy mutations are presumed to be primarily gain of function mutations, meaning that they lead to an increase in the amount of sodium current and thereby increasing excitability. Establishing the impact on channel function in vivo beyond reasonable doubt is challenging and some of these mutations may yet lead to loss of function phenotypes.

Mutations in SCN8A have likewise been reported to show a range of gain and loss of function effects on the $Na_V1.6$ channel though, for $Na_V1.6$, most mutations examined have been associated with gain of function phenotypes. Mutations in $Na_V1.6$ have been linked with epilepsy and autism spectrum disorders (Trudeau, M. M. et al., *Journal of Medical Genetics* (2006), Vol. 43, pp. 527-530; Veeramah, K. R. et al., *Am. J. Hum. Genet.* (2012), Vol. 90, pp. 502-510; Vaher, U. et al., *Journal of Child Neurology* (2013); de Kovel, C. G. et al., *Epilepsy Research* (2014); Estacion, M. et al., *Neurobiology of Disease* (2014), Vol. 69, pp. 117-123; Ohba, C. et al., *Epilepsia* (2014), Vol. 55, pp. 994-1000; Wagnon, J. L. et al., *Human Molecular Genetics* (2014); Kong, W. et al., *Epilepsia* (2015), Vol. 56, pp. 431-438; and Larsen, J. et al., *Neurology* (2015), Vol. 84, pp. 480-489). The best described SCN8A mutant patients have a syndrome known as early infantile epileptic encephalopathy, 13 (EIEE13). Over 100 EIEE13 patients have been identified. Patients typically present with intractable seizures between birth and 18 months of age. Patients have developmental and cognitive delay, and motor impairment often associated with chronic muscular hypotonia. The most severely impacted patients never gain sufficient motor control to walk. Many are not verbal. Less severe phenotypes learn to walk and talk but are motor-impaired and miss cognitive and social milestones. Most of the identified mutations are missense mutations, and it is assumed that the specific functional impact of the mutation contributes to the variability in the phenotype, though genetic background is also likely involved (Larsen, J. et al., *Neurology* (2015), Vol. 84, pp. 480-489). In contrast to SMEI patients, anecdotal evidence suggests that antiepileptic drugs that target voltage-gated sodium channels non-selectively can ameliorate symptoms in EIEE13 patients, though no controlled clinical trials have been completed (Boerma, R. S. et al., *Neurotherapeutics: The Journal of the American Society for Experimental Neuro Therapeutics* (2016), Vol. 13, pp. 192-197). While phenytoin does seem to provide efficacy for EIEE13 patients, it does so at a cost. Efficacy is only achieved at very high doses where the significant adverse effects are tolerated only because the patients are in such dire need. Adverse effects commonly associated with phenytoin therapy include hepatic necrosis, hypertrichosis, nervousness, tremor of hands, numbness, dizziness, drowsiness, tremor, depression, confusion, fatigue, constipation, vertigo, ataxia, mental status changes, myasthenia, mood changes, restlessness, irritability, and excitement. It seems likely that a drug that selectively targets $Na_V1.6$ would retain efficacy while reducing its adverse event burden.

Loss of function mutations in SCN8A in mice lead to a phenotype known as motor endplate disease (med) and multiple mutations and phenotypes were linked to the med gene region prior to the identification of the SCN8A gene (Burgess, D. L. et al., *Nat. Genet.* (1995), Vol. 10, pp. 461-465). Mice with $SCN8A^{med}$ mutations have varying degrees of muscle hypotonia, consistent with the degree of dysfunction of the $Na_V1.6$ function. Mice with the $SCN8A^{med/jo}$ have $Na_V1.6$ channels that have a loss of function, but not null, phenotype. $SCN8A^{med}$ and $SCN8A^{med/jo}$ mice are resistant to seizures induced by chemical insult (flurothyl, kainic acid, and picrotoxin) (Martin, M. S. et al., *Human Molecular Genetics* (2007), Vol. 16, pp. 2892-2899; Hawkins, N. A. et al., *Neurobiology of Disease* (2011), Vol. 41, pp. 655-660; and Makinson, C. D. et al., *Neurobiology of Disease* (2014), Vol. 68, pp. 16-25). Curiously, when $SCN8A^{med/jo}$ mice are crossed with $SCN1A^{null}$ mutant mice to produce a mouse that is heterozygous for both the $SCN1A^{null}$ allele and the $SCN8A^{med/jo}$ allele the double mutant mice have a much improved seizure and cognitive phenotype than those with only an $SCN1A^{null}$ mutation (Martin, M. S. et al., *Human Molecular Genetics* (2007), Vol. 16, pp. 2892-2899). Such mice have a spontaneous seizure and death rate similar to wild type mice and their seizure threshold after chemical insult is also increased. A similar result occurs upon crossing mice with missense mutations of SCN1A (a model for GEFS+) and mice with SCN8A loss of function mutations. Having a single allele of SCN8A$^{med/jo}$ protected the GEFS+ model mice from seizures and premature death (Hawkins, N. A. et al., *Neurobiology of Disease* (2011), Vol. 41, pp. 655-660). The ability of SCN8A knock down to improve seizure resistance is not limited to knockouts where the gene is globally absent throughout animal development. Knock down of SCN8A in adult mice either globally or specifically in the hippocampus via a CRE-LOX inducible knockout approach also improved resistance to electrically and chemically induced seizures Makinson, C. D. et al., *Neurobiology of Disease* (2014), Vol. 68, pp. 16-25). These data suggest that the suppression of inhibitory signaling caused by decreased $Na_V1.1$ current can be offset, at least in part, by suppressing excitatory signaling via decreased in $Na_V1.6$ current.

Voltage-gated sodium channel antagonism is the most common mechanism of widely prescribed antiepileptic drugs (AED's) (Ochoa, J. R. et al., *Sodium Channel Blockers. In: Antiepileptic Drugs* (2016), Vol. (Benbadis, S., ed) Medscape News & Perspectives). Carbamazepine, Eslicarbazepine, Oxcarbazepine, Lacosamide, Lamotrigine, Phenytoin, Rufinamide and Zonisamide are all believed to act primarily by blocking that function of $Na_V$ channels. Despite the presumed mechanism of action, these drugs are relatively promiscuous. They block all $Na_V$ channel isoforms indiscriminately, thus block of $Na_V1.1$ would be expected to proconvulsant. Block of $Na_V1.6$, and perhaps $Na_V1.2$, would be anticonvulsant. In addition to sodium channels, these compounds also block other targets, including voltage-gated calcium channels. Selective $Na_V$ antagonists that spare $Na_V1.1$ and other off-target receptors are expected to have both improved efficacy and therapeutic index relative to the currently available $Na_V$ blocking drugs.

There is therefore an unmet medical need to treat epilepsy and other $Na_V1.6$ associated pathological states effectively and without adverse side effects due to the blocking of other sodium channels, such as $Na_V1.1$ and/or $Na_V1.5$. The present invention provides methods to meet these critical needs.

SUMMARY OF THE INVENTION

The present invention is directed to benzenesulfonamide compounds and pharmaceutical compositions comprising the compounds and methods of using the compounds and the pharmaceutical compositions of the invention for the treatment of diseases or conditions associated with the activity of voltage-gated sodium channels, particularly, $Na_V1.6$ activity, such as epilepsy and/or epileptic seizure disorder.

Accordingly, in one aspect, this invention is directed to compounds of formula (I):

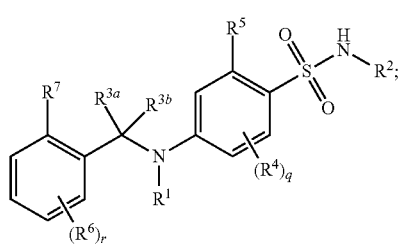

wherein:
q is 1 or 2;
r is 1 or 2;

$R^1$ is hydrogen or alkyl;
$R^2$ is thiazolyl, isothiazolyl or isoxazolyl;
$R^{3a}$ and $R^{3b}$ are each independently hydrogen or alkyl;
each $R^4$ is independently halo or alkyl;
$R^5$ is halo;
each $R^6$ is independently halo or alkoxy;
$R^7$ is azabicyclo[2.2.1]heptanylalkyl or $R^7$ is ((methyl)(prop-2-yl)amino)alkyl when r is 2 and at least one $R^6$ is alkoxy;
as an individual stereoisomer, enantiomer or tautomer thereof or a mixture thereof;
or a pharmaceutically acceptable salt, solvate or prodrug thereof.

The compounds of the invention, which are compounds of formula (I) as described above, as individual stereoisomers, enantiomers or tautomers thereof or mixtures thereof; or as pharmaceutically acceptable salts, solvates or prodrugs thereof, are useful in treating diseases or conditions associated with voltage-gated sodium channels, preferably $Na_V1.6$. Preferably, the compounds of the invention are $Na_V1.6$ inhibitors. More preferably, the compounds of the invention show selectivity of inhibiting $Na_V1.6$ as compared with inhibiting $Na_V1.5$ and/or $Na_V1.1$. Without wishing to be bound by theory, such selectivity is thought to advantageously reduce any side effects which may be associated with the inhibition of $Na_V1.5$ and/or $Na_V1.1$.

In another aspect, the invention provides pharmaceutical compositions comprising a pharmaceutically acceptable excipient and a compound of formula (I), as described above, as a stereoisomer, enantiomer or tautomer thereof or mixtures thereof; or a pharmaceutically acceptable salt, solvate or prodrug thereof.

In another aspect, the invention provides methods for the treatment of epilepsy and/or epileptic seizure disorder in a mammal, preferably a human, wherein the methods comprise administering to the mammal in need thereof a therapeutically effective amount of a compound of the invention, as set forth above, as a stereoisomer, enantiomer or tautomer thereof or mixtures thereof; or a pharmaceutically acceptable salt, solvate or prodrug thereof, or a pharmaceutical composition comprising a therapeutically effective amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

In another aspect, the present invention provides a method for treating or lessening the severity of a disease, condition, or disorder in a mammal where activation or hyperactivity of $Na_V1.6$ is implicated in the disease, condition or disorder, wherein the method comprises administering to the mammal in need thereof a therapeutically effective amount of a compound of the invention, as set forth above, as a stereoisomer, enantiomer or tautomer thereof or mixtures thereof; or a pharmaceutically acceptable salt, solvate or prodrug thereof, or a pharmaceutical composition comprising a therapeutically effective amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

In another aspect, the invention provides methods of treating or ameliorating, but not preventing, epilepsy and/or epileptic seizure disorder in a mammal, wherein the methods comprise administering to the mammal in need thereof a therapeutically effective amount of a compound of the invention, as set forth above, as a stereoisomer, enantiomer or tautomer thereof or mixtures thereof, or a pharmaceutically acceptable salt, solvate or prodrug thereof, or a pharmaceutical composition comprising a therapeutically effective amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

In another aspect, the invention provides pharmaceutical therapy in combination with one or more other compounds of the invention or one or more other accepted therapies or as any combination thereof to increase the potency of an existing or future drug therapy or to decrease the adverse events associated with the accepted therapy. In one embodiment, the present invention relates to a pharmaceutical composition combining compounds of the present invention with established or future therapies for the indications listed herein.

In another aspect, this invention is directed to methods of selectively inhibiting a first voltage-gated sodium channel in a mammal over a second voltage-gated sodium channel, wherein the method comprises administering to the mammal a inhibitory amount of a compound of the invention, as set forth above, as a stereoisomer, enantiomer or tautomer thereof or mixtures thereof; or a pharmaceutically acceptable salt, solvate or prodrug thereof, or a pharmaceutical composition comprising a inhibitory amount of a compound of the invention, as set forth above, as a stereoisomer, enantiomer or tautomer thereof or mixtures thereof, or a pharmaceutically acceptable salt, solvate or prodrug thereof, and a pharmaceutically acceptable excipient.

In another aspect, this invention is directed to the use of the compounds of the invention, as set forth above, as a stereoisomer, enantiomer or tautomer thereof or mixtures thereof, or a pharmaceutically acceptable salt, solvate or prodrug thereof, or the use of a pharmaceutical composition comprising a pharmaceutically acceptable excipient and a compound of the invention, as set forth above, as a stereoisomer, enantiomer or tautomer thereof or mixtures thereof, or a pharmaceutically acceptable salt, solvate or prodrug thereof, in the preparation of a medicament for the treatment of a disease or condition associated with the activity of a voltage-gated sodium channel, preferably $Na_V1.6$, in a mammal and preferably wherein the disease or condition is epilepsy and/or epileptic seizure disorder.

DETAILED DESCRIPTION OF THE INVENTION

Definitions

Certain chemical groups named herein may be preceded by a shorthand notation indicating the total number of carbon atoms that are to be found in the indicated chemical group. For example; $C_7$-$C_{12}$alkyl describes an alkyl group, as defined below, having a total of 7 to 12 carbon atoms, and $C_4$-$C_{12}$cycloalkylalkyl describes a cycloalkylalkyl group, as defined below, having a total of 4 to 12 carbon atoms. The total number of carbons in the shorthand notation does not include carbons that may exist in substituents of the group described.

In addition to the foregoing, as used in the specification and appended claims, unless specified to the contrary, the following terms have the meaning indicated:

"Alkyl" refers to a straight or branched hydrocarbon chain radical consisting solely of carbon and hydrogen atoms, containing no unsaturation, having from one to twelve carbon atoms, preferably one to eight carbon atoms, more preferably one to six carbon atoms, and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, and the like. When specifically stated in the specification, an alkyl group may be optionally substituted by one of the following groups: alkyl, alkenyl, halo, haloalkenyl, cyano, nitro, aryl, cycloalkyl, heterocyclyl, heteroaryl, oxo, trimethylsilanyl, —$OR^{20}$, —$OC(O)$—$R^{20}$, —$N(R^{20})_2$, —$C(O)R^{20}$, —$C(O)OR^{20}$, —$C(O)N(R^{20})_2$, —$N(R^{20})C(O)OR^{22}$, —$N(R^{20})C(O)R^{22}$, —$N(R^{20})S(O)_pR^{22}$ (where p is 1 to 2), —$S(O)_pOR^{22}$ (where p is 1 to 2), —$S(O)_tR^{22}$ (where t is 0 to 2), and —$S(O)_pN(R^{20})_2$ (where p is 1 to 2) where each $R^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each $R^{22}$ is alkyl, haloalkyl, cycloalkyl, cycloalkylalkyl, aryl, aralkyl, heterocyclyl, heterocyclylalkyl, heteroaryl or heteroarylalkyl.

"Alkenyl" refers to a straight or branched hydrocarbon chain radical group consisting solely of carbon and hydrogen atoms, containing at least one double bond, having from two to twelve carbon atoms, preferably two to eight carbon atoms and which is attached to the rest of the molecule by a single bond, e.g., ethenyl, prop-1-enyl, but-1-enyl, pent-1-enyl, penta-1,4-dienyl, and the like. When specifically stated in the specification, an alkenyl group may be optionally substituted by one of the following groups: halo, cyano, nitro, aryl, cycloalkyl, heterocyclyl, heteroaryl, oxo, trimethylsilanyl, —$OR^{20}$, —$OC(O)$—$R^{20}$, —$N(R^{20})_2$, —$C(O)R^{20}$, —$C(O)OR^{20}$, —$C(O)N(R^{20})_2$, —$N(R^{20})C(O)OR^{22}$, —$N(R^{20})C(O)R^{22}$, —$N(R^{20})S(O)_pR^{22}$ (where p is 1 to 2), —$S(O)_pOR^{22}$ (where p is 1 to 2), —$S(O)_tR^{22}$ (where t is 0 to 2), and —$S(O)_pN(R^{20})_2$ (where p is 1 to 2) where each $R^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each $R^{22}$ is alkyl, haloalkyl, cycloalkyl, cycloalkylalkyl, aryl, aralkyl, heterocyclyl, heterocyclylalkyl, heteroaryl or heteroarylalkyl.

"Alkoxy" refers to a radical of the formula —$OR_a$ where $R_a$ is an alkyl group as defined above, e.g., methoxy, ethoxy, n-propoxy, isopropoxy and the like. When specifically stated in the specification, the alkyl group may be optionally substituted as defined above for an alkyl radical. Preferably, "alkoxy" refers to methoxy or isopropoxy.

"Alkylene" or "alkylene chain" refers to a straight or branched divalent hydrocarbon chain linking the rest of the molecule to a radical group or linking two parts of the molecule, consisting solely of carbon and hydrogen, containing no unsaturation and having from one to twelve carbon atoms, e.g., methylene, ethylene, propylene, n-butylene, and the like. The alkylene chain may optionally contain one or more heteroatoms wherein a carbon in the alkylene chain is replaced with a heteroatom selected from oxygen, nitrogen or sulfur. The alkylene chain is attached to the rest of the molecule through a single bond and to the radical group through a single bond or is attached to two parts of the molecule through a single bond at each point of attachment. When specifically stated in the specification, an alkylene chain may be optionally substituted by one of the following groups: alkyl, alkenyl, halo, haloalkenyl, cyano, nitro, aryl, cycloalkyl, heterocyclyl, heteroaryl, oxo, trimethylsilanyl, —$OR^{20}$, —$OC(O)$—$R^{20}$, —$N(R^{20})_2$, —$C(O)R^{20}$, —$C(O)OR^{20}$, —$C(O)N(R^{20})_2$, —$N(R^{20})C(O)OR^{22}$, —$N(R^{20})C(O)R^{22}$, —$N(R^{20})S(O)_pR^{22}$ (where p is 1 to 2), —$S(O)_pOR^{22}$ (where p is 1 to 2), —$S(O)_tR^{22}$ (where t is 0 to 2), and —$S(O)_pN(R^{20})_2$ (where p is 1 to 2) where each $R^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each $R^{22}$ is alkyl, haloalkyl, cycloalkyl, cycloalkylalkyl, aryl, aralkyl, heterocyclyl, heterocyclylalkyl, heteroaryl or heteroarylalkyl.

"Aryl" refers to a hydrocarbon ring system radical comprising hydrogen, 6 to 18 carbon atoms and at least one aromatic ring. For purposes of this invention, the aryl radical may be a monocyclic, bicyclic, tricyclic or tetracyclic ring system, which may included fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. When specifically stated in the specification, an aryl group may be optionally substituted by one or more substituents independently selected from the group consisting of alkyl, alkenyl, halo, haloalkyl, haloalkenyl, cyano, nitro, aryl, aralkyl, cycloalkyl, cycloalkylalkyl, heterocyclyl, heterocyclylalkyl, heteroaryl, heteroarylalkyl, —$R^{21}$—$OR^{20}$, —$R^{21}$—OC(O)—$R^{20}$, —$R^{21}$—N($R^{20}$)$_2$, —$R^{21}$—N($R^{20}$)—$R^{23}$—$OR^{20}$, —$R^{21}$—C(O)$R^{20}$, —$R^{21}$—C(O)$OR^{20}$, —$R^{21}$—C(O)N($R^{20}$)$_2$, —$R^{21}$—N($R^{20}$)C(O)$OR^{22}$, —$R^{21}$—N($R^{20}$)C(O)$R^{22}$, —$R^{21}$—N($R^{20}$)S(O)$_p R^{22}$ (where p is 1 to 2), —$R^{21}$—N=C($OR^{20}$)$R^{20}$, —$R^{21}$—S(O)$_p OR^{22}$ (where p is 1 to 2), —$R^{21}$—S(O)$_t R^{22}$ (where t is 0 to 2), and —$R^{21}$—S(O)$_p$N($R^{20}$)$_2$ (where p is 1 to 2) where each $R^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; each $R^{21}$ is independently a direct bond or a straight or branched alkylene chain; each $R^{22}$ is alkyl, haloalkyl, cycloalkyl, cycloalkylalkyl, aryl, aralkyl, heterocyclyl, heterocyclylalkyl, heteroaryl or heteroarylalkyl, and each $R^{23}$ is a direct bond or a straight or branched alkylene chain. Preferably, the optional substituents on an optionally substituted aryl group for $R^1$ herein are alkyl, optionally substituted cycloalkyl, halo, haloalkyl, cyano, optionally substituted heterocyclyl, optionally substituted heterocyclylalkyl, optionally substituted heteroaryl —$R^{21}$—$OR^{20}$ and —$R^{21}$—N($R^{20}$)$_2$, (where $R^{20}$ and $R^{21}$ are as defined above).

"Cycloalkyl" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, and the like. When specifically stated in the specification, a cycloalkyl group may be optionally substituted by one or more substituents independently selected from the group consisting of alkyl, alkenyl, halo, haloalkyl, haloalkenyl, cyano, nitro, oxo, aryl, aralkyl, cycloalkyl, cycloalkylalkyl, heterocyclyl, heterocyclylalkyl, heteroaryl, heteroarylalkyl, —$R^{21}$—$OR^{20}$, —$R^{21}$—OC(O)—$R^{20}$, —$R^{21}$—N($R^{20}$)—$R^{23}$—$OR^{20}$, —$R^{21}$—N($R^{20}$)$_2$, —$R^{21}$—C(O)$R^{20}$, —$R^{21}$—C(O)$OR^{20}$, —$R^{21}$—C(O)N($R^2$)$_2$, —$R^{21}$—N($R^{20}$)C(O)$OR^{22}$, —$R^{21}$—N($R^{20}$)C(O)$R^{22}$, —$R^{21}$—N($R^{20}$)S(O)$_p R^{22}$ (where p is 1 to 2), —$R^{21}$—N=C($OR^{20}$)$R^{20}$, —$R^{21}$—S(O)$_p OR^{22}$ (where p is 1 to 2), —$R^{21}$—S(O)$_t R^{22}$ (where t is 0 to 2), and —$R^{21}$—S(O)$_p$N($R^{20}$)$_2$ (where p is 1 to 2) where each $R^{20}$ is independently hydrogen, alkyl, haloalkyl, cycloalkyl, cycloalkylalkyl, aryl, aralkyl, heterocyclyl, heterocyclylalkyl, heteroaryl or heteroarylalkyl; each $R^{21}$ is independently a direct bond or a straight or branched alkylene chain; each $R^{22}$ is alkyl, haloalkyl, cycloalkyl, cycloalkylalkyl, aryl, aralkyl, heterocyclyl, heterocyclylalkyl, heteroaryl or heteroarylalkyl, and each $R^{23}$ is a direct bond or a straight or branched alkylene chain.

"Cycloalkylalkyl" refers to a radical of the formula —$R_b R_g$ where $R_b$ is an alkylene chain as defined above and $R_g$ is a cycloalkyl radical as defined above. When specifically stated in the specification, the alkylene chain and/or the cycloalkyl radical may be optionally substituted as defined above for optionally substituted alkylene chain and optionally substituted cycloalkyl.

"Halo" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like. The alkyl part of the haloalkyl radical may be optionally substituted as defined above for an alkyl group.

"Heterocyclyl" refers to a stable 3- to 18-membered non-aromatic ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused, bridged and spiro ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, azetidinyl, 3-azabicyclo[3.1.0]hexan-3-yl, 1-azaspiro[3.3]heptan-1-yl, 5-azaspiro[2.3]hexan-5-yl, azabicyclo[2.2.1]heptanyl, 2-oxa-6-azaspiro[3.3]heptan-6-yl, 1-oxa-6-azaspiro[3.4]octan-6-yl, 1-oxa-6-azaspiro[3.3]heptan-6-yl, 6-oxa-1-azaspiro[3.3]heptan-1-yl, 6-azaspiro[3.4]octan-6-yl, 7-oxa-2-azaspiro[3.5]nonan-2-yl, 2,6-diazaspiro[3.3]heptan-2-yl, dioxolanyl, dioxinyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, 1,2,4-thiadiazol-5(4H)-ylidene, tetrahydrofuryl, trioxanyl, trithianyl, thiazinanyl, tetrahydropyranyl, thiomorpholinyl, thiamorpholinyl, 1-oxo-thiomorpholinyl, and 1,1-dioxo-thiomorpholinyl. When specifically stated in the specification, a heterocyclyl group may be optionally substituted by one or more substituents selected from the group consisting of alkyl, alkenyl, halo, haloalkyl, haloalkenyl, cyano, oxo, thioxo, nitro, aryl, aralkyl, cycloalkyl, cycloalkylalkyl, heterocyclyl, heterocyclylalkyl, heteroaryl, heteroarylalkyl, —$R^{21}$—$OR^{20}$, —$R^{21}$—OC(O)—$R^{20}$, —$R^{21}$—N($R^{20}$)—$R^{23}$—$OR^{20}$, —$R^{21}$—N($R^{20}$)$_2$, —$R^{21}$—C(O)$R^{20}$, —$R^{21}$—C(O)$OR^{20}$, —$R^{21}$—C(O)N($R^{20}$)$_2$, —$R^{21}$—N($R^{20}$)C(O)$OR^{22}$, —$R^{21}$—N($R^{20}$)C(O)$R^{22}$, —$R^{21}$—N($R^{20}$)S(O)$_p R^{22}$ (where p is 1 to 2), —$R^{21}$—N=C($OR^{20}$)$R^{20}$, —$R^{21}$—S(O)$_p OR^{22}$ (where p is 1 to 2), —$R^{21}$—S(O)$_t R^{22}$ (where t is 0 to 2), and —$R^{21}$—S(O)$_p$N($R^{20}$)$_2$ (where p is 1 to 2) where each $R^{20}$ is independently hydrogen, alkyl, alkenyl, haloalkyl, cycloalkyl, cycloalkylalkyl, aryl, aralkyl, heterocyclyl, heterocyclylalkyl, heteroaryl or heteroarylalkyl; each $R^{21}$ is independently a direct bond or a straight or branched alkylene chain; each $R^{22}$ is alkyl, alkenyl, haloalkyl, cycloalkyl, cycloalkylalkyl, aryl, aralkyl, heterocyclyl, heterocyclylalkyl, heteroaryl or heteroarylalkyl, and each $R^{23}$ is a direct bond or a straight or branched alkylene chain.

"Heterocyclylalkyl" refers to a radical of the formula —$R_bR_h$ where $R_b$ is an alkylene chain as defined above and $R_h$ is a heterocyclyl radical as defined above, and if the heterocyclyl is a nitrogen-containing heterocyclyl, the heterocyclyl may be attached to the alkyl radical at the nitrogen atom. When specifically stated in the specification, the alkylene chain of the heterocyclylalkyl radical may be optionally substituted as defined above for an optionally substituted alkylene chain. When specifically stated in the specification, the heterocyclyl part of the heterocyclylalkyl radical may be optionally substituted as defined above for an optionally substituted heterocyclyl group. Preferably the optional substituents on the optionally substituted heterocyclylalkyl group for $R^5$ herein are halo.

"Azabicyclo[2.2.1]heptanylalkyl" refers to a radical of the formula —$R_bR_j$ where $R_b$ is an alkylene chain as defined above and $R_j$ is azabicyclo[2.2.1]heptanyl. Preferably, $R_b$ is a straight or branched divalent hydrocarbon chain consisting solely of carbon and hydrogen, containing no unsaturation and having from one to eight carbon atoms, preferably a straight divalent hydrocarbon chain consisting of one carbon or a branched divalent carbon consisting of two carbons.

"((Methyl)(prop-2-yl)amino)alkyl" refers to the radical of the formula —$R_bN(R_a)_2$ where $R_b$ is an alkylene chain as defined above and one $R_a$ is methyl and the other $R_a$ is prop-2-yl. Preferably, $R_b$ is a straight or branched divalent hydrocarbon chain consisting solely of carbon and hydrogen, containing no unsaturation and having from one to eight carbon atoms, preferably one carbon atom.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzthiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, benzoxazolinonyl, benzimidazolthionyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, pteridinonyl, purinyl, pyrrolyl, pyrazolyl, pyridinyl, pyridinonyl, pyrazinyl, pyrimidinyl, pryrimidinonyl, pyridazinyl, pyrrolyl, pyrido[2,3-d]pyrimidinonyl, quinazolinyl, quinazolinonyl, quinoxalinyl, quinoxalinonyl, quinolinyl, isoquinolinyl, tetrahydroquinolinyl, thiazolyl, thiadiazolyl, thieno[3,2-d]pyrimidin-4-onyl, thieno[2,3-d]pyrimidin-4-onyl, triazolyl, tetrazolyl, triazinyl, and thiophenyl (i.e. thienyl). When specifically stated in the specification, a heteroaryl group may be optionally substituted by one or more substituents selected from the group consisting of alkyl, alkenyl, halo, haloalkyl, haloalkenyl, cyano, oxo, thioxo, nitro, thioxo, aryl, aralkyl, cycloalkyl, cycloalkylalkyl, heterocyclyl, heterocyclylalkyl, heteroaryl, heteroarylalkyl, —$R^{21}$—$OR^{20}$, —$R^{21}$—OC(O)—$R^{20}$, —$R^{21}$—N($R^{20}$)—$R^{23}$—$OR^{20}$, —$R^{21}$—N($R^{20}$)$_2$, —$R^{21}$—C(O)$R^{20}$, —$R^{21}$—C(O)$OR^{20}$, —$R^{21}$—C(O)N($R^{20}$)$_2$, —$R^{21}$—N($R^{20}$)C(O)$OR^{22}$, —$R^{21}$—N($R^{20}$)C(O)$R^{22}$, —$R^{21}$—N($R^{20}$)S(O)$_p$$R^{22}$ (where p is 1 to 2), —$R^{21}$—N=C(O$R^{20}$)$R^{20}$, —$R^{21}$—S(O)$_p$$OR^{22}$ (where p is 1 to 2), —$R^{21}$—S(O)$_p$$R^{22}$ (where t is 0 to 2), and —$R^{21}$—S(O)$_p$N($R^{20}$)$_2$ (where p is 1 to 2) where each $R^{20}$ is independently hydrogen, alkyl, alkenyl, haloalkyl, cycloalkyl, cycloalkylalkyl, aryl, aralkyl, heterocyclyl, heterocyclylalkyl, heteroaryl or heteroarylalkyl; each $R^{21}$ is independently a direct bond or a straight or branched alkylene chain; each $R^{22}$ is alkyl, alkenyl, haloalkyl, cycloalkyl, cycloalkylalkyl, aryl, aralkyl, heterocyclyl, heterocyclylalkyl, heteroaryl or heteroarylalkyl, and each $R^{23}$ is a direct bond or a straight or branched alkylene chain. Preferably, the optional substituents on an optionally substituted bicyclic heteroaryl group for $R^1$ herein are halo. Preferably, the optional substituents on an optionally substituted monocyclic heteroaryl group for $R^1$ herein are alkyl.

"Heteroarylalkyl" refers to a radical of the formula —$R_bR_i$ where $R_b$ is an alkylene chain as defined above and $R_i$ is a heteroaryl radical as defined above. When specifically stated in the specification, the heteroaryl part of the heteroarylalkyl radical may be optionally substituted as defined above for an optionally substituted heteroaryl group. When specifically stated in the specification, the alkylene chain part of the heteroarylalkyl radical may be optionally substituted as defined above for an optionally substituted alkylene chain.

"Prodrug" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see, Bundgard, H., *Design of Prodrugs* (1985), pp. 7-9, 21-24 (Elsevier, Amsterdam)). A discussion of prodrugs is provided in Higuchi, T., et al., "Pro-drugs as Novel Delivery Systems," A.C.S. Symposium Series, Vol. 14, and in Bioreversible Carriers in Drug Design, Ed. Edward B. Roche, American Pharmaceutical Association and Pergamon Press, 1987, both of which are incorporated in full by reference herein.

The term "prodrug" is also meant to include any covalently bonded carriers, which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol or amide derivatives of amine functional groups in the compounds of the invention and the like.

The invention disclosed herein is also meant to encompass all pharmaceutically acceptable compounds of formula (I) being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These radiolabelled compounds could be useful to help determine or measure the effectiveness of the compounds, by characterizing, for example, the site or mode of action on the sodium channels, or binding affinity to pharmacologically important site of action on the sodium channels. Certain isotopically-labelled compounds of formula (I), for example, those incorporating a radioactive isotope, are useful in drug and/or substrate tissue distribution studies. The radioactive isotopes tritium, i.e. $^{3}H$, and carbon-14, i.e. $^{14}C$, are particularly useful for this purpose in view of their ease of incorporation and ready means of detection.

Substitution with heavier isotopes such as deuterium, i.e. $^{2}H$, may afford certain therapeutic advantages resulting from greater metabolic stability, for example, increased in vivo half-life or reduced dosage requirements, and hence may be preferred in some circumstances. In one embodiment of the invention, the compounds of formula (I) are enriched with deuterium. Such deuterated compounds can be achieved by methods known to one skilled in the art, such as exchanging protons with deuterium or by synthesizing the molecule with enriched starting materials.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of formula (I) can generally be prepared by conventional techniques known to those skilled in the art or by processes analogous to those described in the Examples and Preparations as set out below using an appropriate isotopically-labeled reagent in place of the non-labeled reagent previously employed.

The invention disclosed herein is also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the invention includes compounds produced by a process comprising contacting a compound of this invention with a mammal for a period of time sufficient to yield a metabolic product thereof. Such products are typically are identified by administering a radiolabelled compound of the invention in a detectable dose to an animal, such as rat, mouse, guinea pig, monkey, or to human, allowing sufficient time for metabolism to occur, and isolating its conversion products from the urine, blood or other biological samples.

"Stable compound" and "stable structure" are meant to indicate a compound that is sufficiently robust to survive isolation to a useful degree of purity from a reaction mixture, and formulation into an efficacious therapeutic agent.

"Mammal" includes humans and both domestic animals such as laboratory animals and household pets, (e.g., cats, dogs, swine, cattle, sheep, goats, horses, rabbits), and non-domestic animals such as wildlife and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution ("unsubstituted). When a functional group is described as "optionally substituted," and in turn, substitutents on the functional group are also "optionally substituted" and so on, for the purposes of this invention, such iterations are limited to five, preferably such iterations are limited to two.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

"Therapeutically effective amount" refers to that amount of a compound of the invention which, when administered to a mammal, preferably a human, is sufficient to effect treatment, as defined below, of a sodium channel-mediated disease or condition in the mammal, preferably a human. The amount of a compound of the invention which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or condition of interest, and includes:

(a) preventing the disease or condition from occurring in a mammal, in particular, when such mammal is predisposed to the condition but has not yet been diagnosed as having it;

(b) inhibiting the disease or condition, i.e., arresting its development;

(c) relieving (or ameliorating) the disease or condition, i.e., causing regression of the disease or condition; or (d) relieving (or ameliorating) the symptoms resulting from the disease or condition, e.g., relieving epilepsy without addressing the underlying disease or condition.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the invention, or their pharmaceutically acceptable salts may contain one or more asymmetric centres and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallisation. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes enantiomers, which refers to two stereoisomers whose molecules are nonsuperimposable mirror images of one another. See, for example, Smith, M. B. and J. March, *March's Advanced Organic Chemistry: Reactions, Mechanisms, and Structure*, 6th edition (Wiley, 2007), for a detailed description of the structure and properties of enantiomers and stereoisomers.

A "tautomer" refers to a proton shift from one atom of a molecule to another atom of the same molecule. The present invention includes tautomers of any said compounds.

The use of parentheses and brackets in substituent groups is used herein to conserve space. Accordingly, the use of parenthesis in a substituent group indicates that the group enclosed within the parentheses is attached directly to the atom preceding the parenthesis. The use of brackets in a substituent group indicates that the group enclosed within the brackets is also attached directly to the atom preceding the parenthesis.

"Enantiomers" refer to asymmetric molecules that can exist in two different isomeric forms which have different configurations in space. Other terms used to designate or refer to enantiomers include "stereoisomers" (because of the different arrangement or stereochemistry around the chiral center; although all enantiomers are stereoisomers, not all stereoisomers are enantiomers) or "optical isomers" (because of the optical activity of pure enantiomers, which is the ability of different pure enantiomers to rotate plane-polarized light in different directions).

The designations, "R" and "S", for the absolute configuration of an enantiomer of the invention may appear as a prefix or as a suffix in the name of the compound; they may or may not be separated from the enantiomer name by a hyphen; they may or may not be hyphenated; and they may or may not be surrounded by parentheses.

In the formulae depicted herein, a bond to a substituent and/or a bond that links a molecular fragment to the remainder of a compound may be shown as intersecting one or more bonds in a ring structure. This indicates that the bond may be attached to any one of the atoms that constitutes the ring structure, so long as a hydrogen atom could otherwise be present at that atom. Where no particular substituent(s) is identified for a particular position in a structure, then hydrogen(s) is present at that position. For example, in the following structure (D), the bond attaching the $R^{30}$ substituent can be on any of the carbons, including the carbon to which the $R^{31}$ is attached, provided that the valency allows for such an attachment:

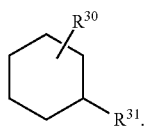

"Resolution" or "resolving" when used in reference to a racemic compound or a racemic mixture of a compound of the invention refers to the separation of the racemic compound or a racemic mixture into its two enantiomeric forms (i.e., (+) and (−); (R) and (S) forms).

The chemical naming protocol and structure diagrams used herein are a modified form of the I.U.P.A.C. nomenclature system, using ChemDraw Professional Version 18.0.0.231 software program, wherein the compounds of the invention are named herein, for example, as derivatives of a central core structure, e.g., the benzenesulfonamide structure. For complex chemical names employed herein, a substituent group is named before the group to which it attaches. For example, cyclopropylethyl comprises an ethyl backbone with cyclopropyl substituent. In chemical structure diagrams, all bonds are identified, except for some carbon atoms, which are assumed to be bonded to sufficient hydrogen atoms to complete the valency.

Accordingly, the compound of formula (I), as described above in the Summary of the Invention, wherein q and r are both 1, $R^1$ is hydrogen, $R^2$ is isothiazol-3-yl, $R^{3a}$ and $R^{3b}$ are each hydrogen, $R^4$ is fluoro, $R^6$ is fluoro and $R^7$ is (7-azabicyclo[2.2.1]heptan-7-yl)methyl, i.e., the compound of the following structure:

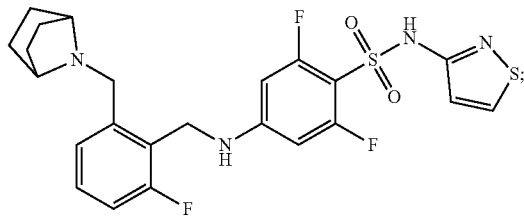 [SMILES: O=S(=O)(Nc1ccsn1)c1c(F)cc(NCc2c(F)cccc2CN2C3CCC2CC3)cc1F]

is named herein as 4-((2-((7-azabicyclo[2.2.1]heptan-7-yl)methyl)-6-fluorobenzyl)amino)-2,6-difluoro-N-(isothiazol-3-yl)benzenesulfonamide.

EMBODIMENTS OF THE INVENTION

One aspect of the invention are compounds of formula (I), as set forth above in the Summary of the Invention, as an individual stereoisomer, enantiomer or tautomer thereof or a mixture thereof; or a pharmaceutically acceptable salt, solvate or prodrug thereof.

One embodiment of the invention are compounds of formula (I) wherein $R^7$ is azabicyclo[2.2.1]heptanylalkyl.

Of this embodiment, a further embodiment are compounds of formula (I) wherein $R^2$ is isothiazolyl.

Of this further embodiment, preferred embodiments are selected from:
4-((2-((7-azabicyclo[2.2.1]heptan-7-yl)methyl)-6-fluorobenzyl)amino)-2,6-difluoro-N-(isothiazol-3-yl)benzenesulfonamide; and
4-((2-((7-azabicyclo[2.2.1]heptan-7-yl)methyl)-6-fluorobenzyl)amino)-2,3-difluoro-N-(isothiazol-3-yl)benzenesulfonamide 2,2,2-trifluoroacetate.

Of the embodiment wherein $R^7$ is azabicyclo[2.2.1]heptanylalkyl, another embodiment are compounds of formula (I) wherein $R^2$ is thiazolyl.

Of this embodiment, one further embodiment are compounds of formula (I) wherein r is 1.

Of this further embodiment, preferred embodiments are selected from:
4-((2-((7-azabicyclo[2.2.1]heptan-7-yl)methyl)-6-fluorobenzyl)amino)-2,3-difluoro-N-(thiazol-4-yl)benzenesulfonamide;
4-((2-((7-azabicyclo[2.2.1]heptan-7-yl)methyl)-6-fluorobenzyl)amino)-3-chloro-2-fluoro-N-(thiazol-4-yl)benzenesulfonamide 2,2,2-trifluoroacetate;
4-((2-((7-azabicyclo[2.2.1]heptan-7-yl)methyl)-6-fluorobenzyl)amino)-2-fluoro-3-methyl-N-(thiazol-4-yl)benzenesulfonamide 2,2,2-trifluoroacetate; and
4-((2-((7-azabicyclo[2.2.1]heptan-7-yl)methyl)-6-fluorobenzyl)amino)-2,6-difluoro-N-(thiazol-4-yl)benzenesulfonamide 2,2,2-trifluoroacetate.

Of the further embodiment wherein $R^2$ is thiazolyl, another further embodiment are compounds of formula (I) where r is 2.

Of this further embodiment, preferred embodiments are selected from:
4-((2-((7-azabicyclo[2.2.1]heptan-7-yl)methyl)-3,6-difluorobenzyl)amino)-2,6-difluoro-N-(thiazol-4-yl)benzenesulfonamide;
4-((2-((7-azabicyclo[2.2.1]heptan-7-yl)methyl)-6-fluoro-3-methoxybenzyl)amino)-2,6-difluoro-N-(thiazol-4-yl)benzenesulfonamide 2,2,2-trifluoroacetate;
4-((2-((7-azabicyclo[2.2.1]heptan-7-yl)methyl)-6-fluoro-3-methoxybenzyl)amino)-2,3-difluoro-N-(thiazol-4-yl)benzenesulfonamide 2,2,2-trifluoroacetate;
4-((2-(1-(7-azabicyclo[2.2.1]heptan-7-yl)ethyl)-3,6-difluorobenzyl)amino)-2,6-difluoro-N-(thiazol-4-yl)benzenesulfonamide 2,2,2-trifluoroacetate;
(S)-4-((2-(1-(7-azabicyclo[2.2.1]heptan-7-yl)ethyl)-3,6-difluorobenzyl)amino)-2,6-difluoro-N-(thiazol-4-yl)benzenesulfonamide; and
(R)-4-((2-(1-(7-azabicyclo[2.2.1]heptan-7-yl)ethyl)-3,6-difluorobenzyl)amino)-2,6-difluoro-N-(thiazol-4-yl)benzenesulfonamide.

Of the embodiment wherein $R^7$ is azabicyclo[2.2.1]heptanylalkyl, another embodiment are compounds of formula (I) wherein $R^2$ is isoxazolyl.

Of this embodiment, preferred embodiments are compounds of formula (I) selected from:
4-((2-((7-azabicyclo[2.2.1]heptan-7-yl)methyl)-6-fluorobenzyl)amino)-2,6-difluoro-N-(isoxazol-3-yl)-3-methylbenzenesulfonamide; and
4-((2-((7-azabicyclo[2.2.1]heptan-7-yl)methyl)-6-fluorobenzyl)amino)-2-fluoro-N-(isoxazol-3-yl)-3-methylbenzenesulfonamide 2,2,2-trifluoroacetate.

Another embodiment of the invention are compounds of formula (I) wherein $R^7$ is azabicyclo[2.2.1]heptanylalkyl.

Of this embodiment, a further embodiment are compounds of formula (I) where $R^7$ is ((methyl)(prop-2-yl)amino)alkyl, provided that r is 2 and at least one $R^6$ is alkoxy.

Of this further embodiment, a further embodiment are compounds of formula (I) wherein $R^2$ is isothiazolyl.

Of the further embodiment where $R^7$ is ((methyl)(prop-2-yl)amino)alkyl, r is 2 and at least one $R^6$ is alkoxy, another further embodiment are compounds of formula (I) wherein $R^2$ is thiazolyl.

Of this further embodiment, preferred compounds of formula (I) are selected from:

2,6-difluoro-4-((6-fluoro-2-((isopropyl(methyl)amino)methyl)-3-methoxybenzyl)amino)-N-(thiazol-4-yl)benzenesulfonamide;

2,6-difluoro-4-((6-fluoro-3-isopropoxy-2-((isopropyl(methyl)amino)methyl)benzyl)amino)-N-(thiazol-4-yl)benzenesulfonamide;

2,3-difluoro-4-((6-fluoro-2-((isopropyl(methyl)amino)methyl)-3-methoxybenzyl)amino)-N-(thiazol-4-yl)benzenesulfonamide;

5-chloro-2-fluoro-4-((6-fluoro-2-((isopropyl(methyl)amino)methyl)-3-methoxybenzyl)amino)-N-(thiazol-4-yl)benzenesulfonamide 2,2,2-trifluoroacetate; and 2-fluoro-4-((6-fluoro-2-((isopropyl(methyl)amino)methyl)-3-methoxybenzyl)amino)-5-methyl-N-(thiazol-4-yl)benzenesulfonamide 2,2,2-trifluoroacetate.

Of the further embodiment where $R^7$ is ((methyl)(prop-2-yl)amino)alkyl, r is 2 and at least one $R^6$ is alkoxy, another further embodiment are compounds of formula (I) wherein $R^2$ is isoxazoyl.

Another embodiment of the invention are compounds of formula (I) wherein one $R^4$ is in the ortho position relative to the —$S(O)_2$—N(H)—$R^2$ substituent.

Another embodiment of the invention are compounds of formula (I) wherein one $R^4$ is in the ortho position relative to —$C(R^{3a})(R^{3b})$—.

Another embodiment of the invention are compounds of formula (I) wherein one $R^6$ is in the ortho position relative to —$C(R^{3a})(R^{3b})$—.

Another embodiment of the invention are compounds of formula (I) wherein $R^5$ is fluoro.

Another embodiment of the invention are compounds of formula (I) wherein one $R^4$ is fluoro.

Another embodiment of the invention are compounds of formula (I) wherein one $R^4$ is chloro.

Another embodiment of the invention are compounds of formula (I) wherein one $R^4$ is methyl.

Another embodiment of the invention are compounds of formula (I) wherein one $R^4$ is fluoro and another $R^4$ is methyl.

Another embodiment of the invention are compounds of formula (I) wherein one $R^6$ is fluoro.

Another embodiment of the invention are compounds of formula (I) wherein one $R^6$ is fluoro and another $R^6$ is methoxy.

Another embodiment of the invention are compounds of formula (I) wherein one $R^6$ is fluoro and another $R^6$ is isopropoxy.

Another embodiment of the invention are compounds of formula (I) wherein one $R^6$ is fluoro and another $R^6$ is fluoro.

Another embodiment of the invention is a method of using the compounds of formula (I) as standards or controls in in vitro or in vivo assays in determining the efficacy of test compounds in modulating voltage-dependent sodium channels.

Another embodiment of the invention are compounds of formula (Ia), compounds of formula (Ib), compounds of formula (Ic), compounds of formula (Id), compounds of formula (Id), compounds of formula (Ie), compounds of formula (If), compounds of formula (Ig), compounds of formula (Ih), compounds of formula (Ii), compounds of formula (Ij) or compounds of formula (Ik), as individual stereoisomers, enantiomers or tautomers thereof or mixtures thereof; or pharmaceutically acceptable salts, solvates or prodrugs thereof, as described below in the Preparation of the Compounds of the Invention.

Another embodiment of the invention is a method of preparing a compound of formula (Ia), as an individual stereoisomer, enantiomer or tautomer thereof or a mixture thereof; or a pharmaceutically acceptable salt thereof, as described herein in Reaction Scheme 1.

Another embodiment of the invention is a method of preparing a compound of formula (Ib), as an individual stereoisomer, enantiomer or tautomer thereof or a mixture thereof; or a pharmaceutically acceptable salt thereof, as described herein in Reaction Scheme 2.

Another embodiment of the invention is a method of preparing a compound of formula (Ic), as an individual stereoisomer, enantiomer or tautomer thereof or a mixture thereof; or a pharmaceutically acceptable salt thereof, as described herein in Reaction Scheme 3.

Another embodiment of the invention is a method of preparing a compound of formula (If), as an individual stereoisomer, enantiomer or tautomer thereof or a mixture thereof; or a pharmaceutically acceptable salt thereof, as described herein in Reaction Scheme 3.

Another embodiment of the invention is a method of preparing a compound of formula (Ig), as an individual stereoisomer, enantiomer or tautomer thereof or a mixture thereof; or a pharmaceutically acceptable salt thereof, as described herein in Reaction Scheme 3.

Another embodiment of the invention is a method of preparing a compound of formula (Id), as an individual stereoisomer, enantiomer or tautomer thereof or a mixture thereof; or a pharmaceutically acceptable salt thereof, as described herein in Reaction Scheme 4.

Another embodiment of the invention is a method of preparing a compound of formula (Ie), as an individual stereoisomer, enantiomer or tautomer thereof or a mixture thereof; or a pharmaceutically acceptable salt thereof, as described herein in Reaction Scheme 5.

Another embodiment of the invention is a method of preparing a compound of formula (Ia), as an individual stereoisomer, enantiomer or tautomer thereof or a mixture thereof; or a pharmaceutically acceptable salt thereof, as described herein in Reaction Scheme 6.

Another embodiment of the invention is a method of preparing a compound of formula (Ih), as an individual stereoisomer, enantiomer or tautomer thereof or a mixture thereof; or a pharmaceutically acceptable salt thereof, as described herein in Reaction Scheme 7.

Another embodiment of the invention is a method of preparing a compound of formula (Ii), as an individual stereoisomer, enantiomer or tautomer thereof or a mixture thereof; or a pharmaceutically acceptable salt thereof, as described herein in Reaction Scheme 8.

Another embodiment of the invention is a method of preparing a compound of formula (Ij), as an individual stereoisomer, enantiomer or tautomer thereof or a mixture thereof; or a pharmaceutically acceptable salt thereof, as described herein in Reaction Scheme 9.

Another embodiment of the invention is a method of preparing a compound of formula (Ik), as an individual stereoisomer, enantiomer or tautomer thereof or a mixture thereof; or a pharmaceutically acceptable salt thereof, as described herein in Reaction Scheme 9.

It is understood that any embodiment of the compounds of the invention, as set forth above, and any specific substituent set forth herein for a particular $R^1$, $R^2$, $R^{3a}$, $R^{3b}$, $R^4$, $R^5$, $R^6$ and $R^7$ substituent in the compounds of the invention, as set forth above, may be independently combined with other embodiments and/or substituents of compounds of the invention to form embodiments of the inventions not specifically set forth above. In addition, in the event that a list of substituents is disclosed for any particular $R^1$, $R^2$, $R^3$, $R^4$, $R^5$, $R^6$ and $R^7$ substituent in a particular embodiment and/or claim, it is understood that one or more substituents may be deleted from the list and that the remaining list of substituents will be considered to be an embodiment of the invention.

Another aspect of the invention is a pharmaceutical composition comprising a pharmaceutically acceptable excipient and a compound of the invention, as described above, as a stereoisomer, enantiomer or tautomer thereof or a mixture thereof; or a pharmaceutically acceptable salt, solvate or prodrug thereof.

Another aspect of the invention is a method of treating a disease or a condition associated with $Na_V1.6$ activity in a mammal wherein the disease or condition is epilepsy and/or epileptic seizure disorder and wherein the method comprises administering to the mammal in need thereof a therapeutically effective amount of a compound of the invention, as described above, as a stereoisomer, enantiomer or tautomer thereof or a mixture thereof; or a pharmaceutically acceptable salt, solvate or prodrug thereof.

In one embodiment of this aspect, the epilepsy or epileptic seizure disorder is selected from photosensitive epilepsy, self-induced syncope, intractable epilepsy, Angelman syndrome, benign rolandic epilepsy, CDKL5 disorder, childhood and juvenile absence epilepsy, Dravet syndrome, frontal lobe epilepsy, Glut1 deficiency syndrome, hypothalamic hamartoma, infantile spasms/West's syndrome, juvenile myoclonic epilepsy, Landau-Kleffner syndrome, Lennox-Gastaut syndrome (LGS), epilepsy with myoclonic-absences, Ohtahara syndrome, Panayiotopoulos syndrome, PCDH19 epilepsy, progressive myoclonic epilepsies, Rasmussen's syndrome, ring chromosome 20 syndrome, reflex epilepsies, temporal lobe epilepsy, Lafora progressive myoclonus epilepsy, neurocutaneous syndromes, tuberous sclerosis complex, early infantile epileptic encephalopathy, early onset epileptic encephalopathy, generalized epilepsy with febrile seizures+, Rett syndrome, multiple sclerosis, Alzheimer's disease, autism, ataxia, hypotonia and paroxysmal dyskinesia.

In one embodiment of this embodiment, the epilepsy or epileptic seizure disorder is selected from Dravet syndrome, infantile spasms/West's syndrome, temporal lobe epilepsy, Lennox-Gastaut syndrome (LGS), generalized epilepsy with febrile seizures + and early infantile epileptic encephalopathy.

Another aspect of the invention is a method of decreasing ion flux through $Na_V1.6$ in a mammalian cell, wherein the method comprises contacting the cell with a compound of the invention, as described above, as a stereoisomer, enantiomer or tautomer thereof or a mixture thereof; or a pharmaceutically acceptable salt, solvate or prodrug thereof.

Another aspect of the invention is a method of selectively inhibiting a first voltage-gated sodium channel over a second voltage-gated sodium channel in a mammal, wherein the method comprises administering to the mammal a modulating amount of a compound of the invention, as described above, as a stereoisomer, enantiomer or tautomer thereof or a mixture thereof; or a pharmaceutically acceptable salt, solvate or prodrug thereof.

In one embodiment of this aspect, the first voltage-gated sodium channel is $Na_V1.6$.

In another embodiment of this aspect, the first voltage-gated sodium channel is $Na_V1.6$ and the second voltage-gated sodium channel is $Na_V1.5$.

In another embodiment of this aspect, the first voltage-gated sodium channel is $Na_V1.6$ and the second voltage-gated sodium channel is $Na_V1.1$.

Specific embodiments of the compounds of the invention are described in more detail below in the Preparation of the Compounds of the Invention and in the Examples.

Utility and Testing of the Compounds of the Invention

The compounds of the invention modulate, preferably inhibit, ion flux through a voltage-dependent sodium channel, preferably $Na_V1.6$, in a mammal, especially in a human. Any such modulation, whether it be partial or complete inhibition or prevention of ion flux, is sometimes referred to herein as "blocking" and corresponding compounds as "blockers" or "inhibitors". In general, the compounds of the invention modulate the activity of a voltage-gated sodium channel downwards by inhibiting the voltage-dependent activity of the sodium channel, and/or reduce or prevent sodium ion flux across a cell membrane by preventing sodium channel activity such as ion flux.

The compounds of the invention inhibit the ion flux through a voltage-dependent sodium channel, preferably $Na_V1.6$. The compounds of the invention are state or frequency dependent modifiers of the sodium channel, having a low affinity for the rested/closed state and a high affinity for the inactivated state. These compounds are likely to interact with overlapping sites located in the inner cavity of the sodium conducting pore of the channel similar to that described for other state-dependent sodium channel blockers (Cestèle, S., et al., op. cit.). These compounds may also be likely to interact with sites outside of the inner cavity and have allosteric effects on sodium ion conduction through the channel pore.

Any of these consequences may ultimately be responsible for the overall therapeutic benefit provided by these compounds.

Accordingly, the compounds of the invention are voltage-gated sodium channel inhibitors, preferably $Na_V1.6$ inhibitors, and are therefore useful for treating diseases and conditions, preferably epilepsy and/or epileptic seizure disorder, in mammals, preferably humans, and other organisms, including all those human diseases and conditions which are the result of aberrant voltage-dependent sodium channel biological activity, preferably aberrant $Na_V1.6$ activity, or which may be ameliorated by modulation of voltage-dependent sodium channel biological activity. In particular, the compounds of the invention, i.e., the compounds of formula (I), as set forth above in the Summary of the Invention, as individual stereoisomers, enantiomers or tautomers thereof or mixtures thereof; or as pharmaceutically acceptable salts, solvates or prodrugs thereof, are useful for treating diseases and conditions in mammals, preferably humans, which are the result of aberrant voltage-dependent $Na_V1.6$ biological activity or which may be ameliorated by the modulation, preferably the inhibition, of $Na_V1.6$ biological activity. Preferably the compounds of the invention selectively inhibit $Na_V1.6$ over $Na_V1.5$ and/or $Na_V1.1$.

As defined herein, a disease, disorder or condition associated with $Na_V1.6$ activity includes, but is not limited to, epilepsy and/or epileptic seizure disorder. Such epilepsy and/or epileptic seizure disorders include, but are not limited to, photosensitive epilepsy, self-induced syncope, intractable epilepsy, Angelman syndrome, benign rolandic epilepsy, CDKL5 disorder, childhood and juvenile absence epilepsy, Dravet syndrome, frontal lobe epilepsy, Glut1 deficiency syndrome, hypothalamic hamartoma, infantile spasms/West's syndrome, juvenile myoclonic epilepsy, Landau-Kleffner syndrome, Lennox-Gastaut syndrome (LGS), epilepsy with myoclonic-absences, Ohtahara syndrome, Panayiotopoulos syndrome, PCDH19 epilepsy, progressive myoclonic epilepsies, Rasmussen's syndrome, ring chromosome 20 syndrome, reflex epilepsies, temporal lobe epilepsy, Lafora progressive myoclonus epilepsy, neurocutaneous syndromes, tuberous sclerosis complex, early infantile epileptic encephalopathy, early onset epileptic encephalopathy, generalized epilepsy with febrile seizures+, Rett syndrome, multiple sclerosis, Alzheimer's disease, autism, ataxia, hypotonia and paroxysmal dyskinesia.

The present invention therefore relates to compounds, pharmaceutical compositions and methods of using the compounds and pharmaceutical compositions for the treatment of diseases or conditions associated by the activity of $Na_V1.6$ in a mammal, preferably a human, by administering to the mammal, preferably the human, in need of such treatment an effective amount of a compound of the invention or an pharmaceutical composition comprising a compound of the invention.

The general value of the compounds of the invention in inhibiting the $Na_V1.6$ ion flux can be determined using the assays described below in the Biological Assays section. Alternatively, the general value of the compounds in treating conditions and diseases in humans may be established in industry standard animal models for demonstrating the efficacy of compounds in treating epilepsy and/or epileptic seizure disorder. Animal models of human epileptic conditions have been developed that result in reproducible sensory deficits over a sustained period of time that can be evaluated by sensory testing.

For example, many rodent models have been developed to assess the propensity for seizures or epileptiform activity (Klein, B. R. et al., (2016), "Models Currently in Active Use. In: Epilepsy Therapy Screening Program", Vol. 2016, National Institute of Neurological Disorders and Stroke). These include acute chemical or electrical insults that induce seizures, as well as chronic chemical or genetic insults that create seizure prone animals. These models can be used to determine the relative ability of a compound to promote or prevent seizure activity. The maximal electroshock seizure (MES) assay and the 6 hertz psychomotor seizure test (6 Hz) are two examples of acute insult seizure assays used to evaluate anticonvulsive interventions (Suzuki, F. et al., Neuroscience (1995), Vo. 64, pp. 665-674; Barton, M. E. et al., Epilepsy Research (2001), Vol. 47, pp. 217-227). Both assays involve an electrical insult applied with electrodes placed on the corneas or ears in order to provoke an acute seizure. Acute seizures may also be induced chemically, for instance by administration of the proconvulsant ether compound flurothyl (Makinson, C. D. et al., Exp. Neurol. (2016), Vol. 275, Pt 1, pp. 46-58).

Genetic epilepsies have been linked to many distinct genes, including multiple voltage gated sodium channel genes. Genetically modified mice can be created that harbor mutations identified in human patients. In some cases these genetic modifications result in animals that behave much like the human patients in whom the genetic variations were initially identified. Mutant mice can be used to test anticonvulsant interventions. Such experiments can involve prevention of spontaneous seizures, or may make use of similar seizure provoking stimuli as those employed in wild type mice. Animal models of early infantile epileptic encephalopathy 6 (EIEE6), also known as severe myoclonic epilepsy of infancy or Dravet syndrome, have been created by mutating the SCN1A gene that encodes the $Na_V1.1$ voltage gated sodium channel (Yu, F. H. et al., Nat. Neurosci. (2006), Vol. 9, pp. 1142-1149). Models of EIEE13 have likewise been created by mutating the SCN6A gene that encodes the $Na_V1.6$ voltage gated sodium channel (Wagnon, J. L. et al., Human Molecular Genetics (2014)). Both of these mouse strains provide the opportunity to evaluate potential therapeutic interventions that might prove useful in clinical patient populations (Martin, M. S. et al., J. Biol. Chem. (2010), Vol. 285, pp. 9823-9834; and Martin, M. S. et al., Human Molecular Genetics (2007), Vol. 16, pp. 2892-2899).

The present invention readily affords many different means for identification of $Na_V1.6$ inhibitory agents that are useful as therapeutic agents. Identification of $Na_V1.6$ inhibitors can be assessed using a variety of in vitro and in vivo assays, e.g., measuring current, measuring membrane potential, measuring ion flux, (e.g., sodium or guanidinium), measuring sodium concentration, measuring second messengers and transcription levels, and using e.g., voltage-sensitive dyes, radioactive tracers, and patch-clamp electrophysiology.

One such protocol involves the screening of chemical agents for ability to modulate the activity of a sodium channel thereby identifying it as a modulating agent.

A typical assay described in Bean et al., J. General Physiology (1983), 83:613-642, and Leuwer, M., et al., Br. J. Pharmacol (2004), 141(1):47-54, uses patch-clamp techniques to study the behaviour of channels. Such techniques are known to those skilled in the art, and may be developed, using current technologies, into low or medium throughput assays for evaluating compounds for their ability to modulate sodium channel behaviour.

Throughput of test compounds is an important consideration in the choice of screening assay to be used. In some strategies, where hundreds of thousands of compounds are to be tested, it is not desirable to use low throughput means. In other cases, however, low throughput is satisfactory to identify important differences between a limited number of compounds. Often it will be necessary to combine assay types to identify specific sodium channel modulating compounds.

Electrophysiological assays using patch clamp techniques is accepted as a gold standard for detailed characterization of sodium channel compound interactions, and as described in Bean et al., op. cit. and Leuwer, M., et al., op. cit. There is a manual low-throughput screening (LTS) method which can compare 2-10 compounds per day; a recently developed system for automated medium-throughput screening (MTS) at 20-50 patches (i.e. compounds) per day; and a technology from Molecular Devices Corporation (Sunnyvale, Calif.) which permits automated high-throughput screening (HTS) at 1000-3000 patches (i.e. compounds) per day.

One automated patch-clamp system utilizes planar electrode technology to accelerate the rate of drug discovery. Planar electrodes are capable of achieving high-resistance, cells-attached seals followed by stable, low-noise whole-cell recordings that are comparable to conventional recordings. A suitable instrument is the PatchXpress 7000A (Axon Instruments Inc, Union City, Calif.). A variety of cell lines and culture techniques, which include adherent cells as well as cells growing spontaneously in suspension are ranked for seal success rate and stability. Immortalized cells (e.g. HEK and CHO) stably expressing high levels of the relevant sodium ion channel can be adapted into high-density suspension cultures.

Other assays can be selected which allow the investigator to identify compounds which block specific states of the channel, such as the open state, closed state or the resting state, or which block transition from open to closed, closed to resting or resting to open. Those skilled in the art are generally familiar with such assays.

Binding assays are also available. Designs include traditional radioactive filter based binding assays or the confocal based fluorescent system available from Evotec OAI group of companies (Hamburg, Germany), both of which are HTS.

Radioactive flux assays can also be used. In this assay, channels are stimulated to open with veratridine or aconitine and held in a stabilized open state with a toxin, and channel blockers are identified by their ability to prevent ion influx. The assay can use radioactive $^{22}$[Na] and $^{14}$[C] guanidinium ions as tracers. FlashPlate & Cytostar-T plates in living cells avoids separation steps and are suitable for HTS. Scintillation plate technology has also advanced this method to HTS suitability. Because of the functional aspects of the assay, the information content is reasonably good.

Yet another format measures the redistribution of membrane potential using the FLIPR system membrane potential kit (HTS) available from Molecular Dynamics (a division of Amersham Biosciences, Piscataway, N.J.). This method is limited to slow membrane potential changes. Some problems may result from the fluorescent background of compounds. Test compounds may also directly influence the fluidity of the cell membrane and lead to an increase in intracellular dye concentrations. Still, because of the functional aspects of the assay, the information content is reasonably good.

Sodium dyes can be used to measure the rate or amount of sodium ion influx through a channel. This type of assay provides a very high information content regarding potential channel blockers. The assay is functional and would measure Na+ influx directly. CoroNa Red, SBFI and/or sodium green (Molecular Probes, Inc. Eugene Oreg.) can be used to measure Na influx; all are Na responsive dyes. They can be used in combination with the FLIPR instrument. The use of these dyes in a screen has not been previously described in the literature. Calcium dyes may also have potential in this format.

In another assay, FRET based voltage sensors are used to measure the ability of a test compound to directly block Na influx. Commercially available HTS systems include the VIPR™ II FRET system (Aurora Biosciences Corporation, San Diego, Calif., a division of Vertex Pharmaceuticals, Inc.) which may be used in conjunction with FRET dyes, also available from Aurora Biosciences. This assay measures sub-second responses to voltage changes. There is no requirement for a modifier of channel function. The assay measures depolarization and hyperpolarizations, and provides ratiometric outputs for quantification. A somewhat less expensive MTS version of this assay employs the FLEXstation™ (Molecular Devices Corporation) in conjunction with FRET dyes from Aurora Biosciences. Other methods of testing the compounds disclosed herein are also readily known and available to those skilled in the art.

These results provide the basis for analysis of the structure-activity relationship (SAR) between test compounds and the sodium channel. Certain substituents on the core structure of the test compound tend to provide more potent inhibitory compounds. SAR analysis is one of the tools those skilled in the art may now employ to identify preferred embodiments of the compounds of the invention for use as therapeutic agents.

Modulating agents so identified are then tested in a variety of in vivo models so as to determine if they are useful in treating the disease or condition associated with the activity of the sodium channel of interest, preferably $Na_V1.6$, with minimal adverse events. The assays described below in the Biological Assays Section are useful in assessing the biological activity of the instant compounds.

Typically, the efficacy of a compound of the invention is expressed by its $IC_{50}$ value ("Inhibitory Concentration—50%"), which is the measure of the amount of compound required to achieve 50% inhibition of the activity of the target sodium channel over a specific time period.

In an alternative use of the invention, the compounds of the invention can be used in in vitro or in vivo studies as exemplary agents for comparative purposes to find other compounds also useful in treatment of, or protection from, the various diseases disclosed herein.

Another aspect of the invention relates to inhibiting $Na_V1.6$ activity in a biological sample or a mammal, preferably a human, which method comprises administering to the mammal, preferably a human, or contacting said biological sample with a compound of formula (I) or a pharmaceutical composition comprising a compound of formula (I). The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of $Na_V1.6$ activity in a biological sample is useful for a variety of purposes that are known to one of skill in the art. Examples of such purposes include, but are not limited to, the study of sodium ion channels in biological and pathological phenomena; and the comparative evaluation of new sodium ion channel inhibitors.

The compounds of the invention, as set forth above in the Summary of the Invention, as stereoisomers, enantiomers, tautomers thereof or mixtures thereof, or pharmaceutically acceptable salts, solvates or prodrugs thereof, and/or the pharmaceutical compositions described herein which comprise a pharmaceutically acceptable excipient and one or more compounds of the invention, as set forth above in the Summary of the Invention, as a stereoisomer, enantiomer or tautomer thereof or mixtures thereof, or a pharmaceutically acceptable salt, solvate or prodrug thereof, can be used in the preparation of a medicament for the treatment of diseases or conditions associated with voltage-gated sodium channel activity, preferably $Na_V1.6$ activity, in a mammal.

Pharmaceutical Compositions of the Invention and Administration

The present invention also relates to pharmaceutical composition containing the compounds of the invention disclosed herein. In one embodiment, the present invention relates to a composition comprising compounds of the invention in a pharmaceutically acceptable carrier, excipient or diluent and in an amount effective to modulate, preferably inhibit, ion flux through a voltage-dependent sodium channel to treat sodium channel mediated diseases, such as epilepsy and/or epileptic seizure disorder, when administered to an animal, preferably a mammal, most preferably a human patient.

Administration of the compounds of the invention, or their pharmaceutically acceptable salts, in pure form or in an appropriate pharmaceutical composition, can be carried out via any of the accepted modes of administration of agents for serving similar utilities. The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, rectal, vaginal, and intranasal. The term "parenteral" as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see *The Science and Practice of Pharmacy,* 20th Edition (Philadelphia College of Pharmacy and Science, 2000). The composition to be administered will, in any event, contain a therapeutically effective amount of a compound of the invention, or a pharmaceutically acceptable salt thereof, for treatment of a disease or condition of interest in accordance with the teachings of this invention.

The pharmaceutical compositions useful herein also contain a pharmaceutically acceptable carrier, including any suitable diluent or excipient, which includes any pharmaceutical agent that does not itself induce the production of antibodies harmful to the individual receiving the composition, and which may be administered without undue toxicity. Pharmaceutically acceptable carriers include, but are not limited to, liquids, such as water, saline, glycerol and ethanol, and the like. A thorough discussion of pharmaceutically acceptable carriers, diluents, and other excipients is presented in *Remington's Pharmaceutical Sciences* (Mack Pub. Co., N.J., current edition).

A pharmaceutical composition of the invention may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, for example, inhalatory administration.

When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of the invention intended for either parenteral or oral administration should contain an amount of a compound of the invention such that a suitable dosage will be obtained. Typically, this amount is at least 0.01% of a compound of the invention in the composition. When intended for oral administration, this amount may be varied to be between 0.1 and about 70% of the weight of the composition. Preferred oral pharmaceutical compositions contain between about 4% and about 50% of the compound of the invention. Preferred pharmaceutical compositions and preparations according to the present invention are prepared so that a parenteral dosage unit contains between 0.01 to 10% by weight of the compound prior to dilution of the invention.

The pharmaceutical composition of the invention may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the compound of the invention from about 0.1 to about 10% w/v (weight per unit volume).

The pharmaceutical composition of the invention may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of the invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the invention in solid or liquid form may include an agent that binds to the compound of the invention and thereby assists in the delivery of the compound. Suitable agents that may act in this capacity include a monoclonal or polyclonal antibody, a protein or a liposome.

The pharmaceutical composition of the invention may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols.

The pharmaceutical compositions of the invention may be prepared by methodology well known in the pharmaceutical art. For example, a pharmaceutical composition intended to be administered by injection can be prepared by combining a compound of the invention with sterile, distilled water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

The compounds of the invention, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy. Generally, a therapeutically effective daily dose is (for a 70 Kg mammal) from about 0.001 mg/Kg (i.e., 0.07 mg) to about 100 mg/Kg (i.e., 7.0 g); preferably a therapeutically effective dose is (for a 70 Kg mammal) from about 0.01 mg/Kg (i.e., 0.7 mg) to about 50 mg/Kg (i.e., 3.5 g); more preferably a therapeutically effective dose is (for a 70 Kg mammal) from about 1 mg/kg (i.e., 70 mg) to about 25 mg/Kg (i.e., 1.75 g).

The ranges of effective doses provided herein are not intended to be limiting and represent preferred dose ranges. However, the most preferred dosage will be tailored to the individual subject, as is understood and determinable by one skilled in the relevant arts (see, e.g., Berkow et al., eds., *The Merck Manual*, 19$^{th}$ edition, Merck and Co., Rahway, N.J., 2011; Brunton et al. eds., *Goodman and Cilman's The Pharmacological Basis of Therapeutics*, 12$^{th}$ edition, McGraw-Hill 2011; Avery's Drug Treatment: Principles and Practice of Clinical Pharmacology and Therapeutics, 3rd edition, ADIS Press, LTD., Williams and Wilkins, Baltimore, Md. (1987), Ebadi, *Pharmacology*, Little, Brown and Co., Boston, (1985); Osolci al., eds., *Remington's Pharmaceutical Sciences*, current edition, Mack Publishing Co., Easton, Pa.; Katzung, *Basic and Clinical Pharmacology*, Appleton and Lange, Norwalk, Conn. (1992)).

The total dose required for each treatment can be administered by multiple doses or in a single dose over the course of the day, if desired. Generally, treatment is initiated with smaller dosages, which are less than the optimum dose of the compound. Thereafter, the dosage is increased by small increments until the optimum effect under the circumstances is reached. The diagnostic pharmaceutical compound or composition can be administered alone or in conjunction with other diagnostics and/or pharmaceuticals directed to the pathology, or directed to other symptoms of the pathology. The recipients of administration of compounds and/or compositions of the invention can be any vertebrate animal, such as mammals. Among mammals, the preferred recipients are mammals of the Orders Primate (including humans, apes and monkeys), Arteriodactyla (including horses, goats, cows, sheep, pigs), Rodenta (including mice, rats and hamsters), Lagamorpha (including rabbits) and Carnivora (including cats, and dogs). Among birds, the preferred recipients are turkeys, chickens and other members of the same order. The most preferred recipients are humans.

For topical applications, it is preferred to administer an effective amount of a pharmaceutical composition according to the invention to target area, e.g., skin surfaces, mucous membranes, and the like, which are adjacent to peripheral neurons which are to be treated. This amount will generally range from about 0.0001 mg to about 1 g of a compound of the invention per application, depending upon the area to be treated, whether the use is diagnostic, prophylactic or therapeutic, the severity of the symptoms, and the nature of the topical vehicle employed. A preferred topical preparation is an ointment, wherein about 0.001 to about 50 mg of active ingredient is used per cc of ointment base. The pharmaceutical composition can be formulated as transdermal compositions or transdermal delivery devices ("patches"). Such compositions include, for example, a backing, active compound reservoir, a control membrane, liner and contact adhesive. Such transdermal patches may be used to provide continuous pulsatile, or on demand delivery of the compounds of the present invention as desired.

The compositions of the invention can be formulated so as to provide quick, sustained or delayed release of the active ingredient after administration to the patient by employing procedures known in the art. Controlled release drug delivery systems are well-known in the art and include osmotic pump systems and dissolutional systems containing polymer-coated reservoirs or drug-polymer matrix formulations.

The compositions of the invention can also be delivered through intra-nasal drug delivery systems for local, systemic, and nose-to-brain medical therapies. Controlled Particle Dispersion (CPD)™ technology, traditional nasal spray bottles, inhalers or nebulizers are known by those skilled in the art to provide effective local and systemic delivery of drugs by targeting the olfactory region and paranasal sinuses.

The invention also relates to an intravaginal shell or core drug delivery device suitable for administration to the human or animal female. The device may be comprised of the active pharmaceutical ingredient in a polymer matrix, surrounded by a sheath, and capable of releasing the compound in a substantially zero order pattern on a daily basis similar to devices used to apply testosterone as described in PCT Published Patent Application No. WO 98/50016.

Current methods for ocular delivery include topical administration (eye drops), subconjunctival injections, periocular injections, intravitreal injections, surgical implants and iontophoresis (uses a small electrical current to transport ionized drugs into and through body tissues). Those skilled in the art would combine the best suited excipients with the compound for safe and effective intra-ocular administration.

The most suitable route will depend on the nature and severity of the condition being treated. Those skilled in the art are also familiar with determining administration methods (e.g., oral, intravenous, inhalation, sub-cutaneous, rectal etc.), dosage forms, suitable pharmaceutical excipients and other matters relevant to the delivery of the compounds to a subject in need thereof.

Combination Therapy

The compounds of the invention may be usefully combined with one or more other compounds of the invention or one or more other therapeutic agent or as any combination thereof, in the treatment of diseases and conditions associated with voltage-gated sodium channel activity. For example, a compound of the invention may be administered simultaneously, sequentially or separately in combination with other therapeutic agents, including, but not limited to:

- opiates analgesics, e.g., morphine, heroin, cocaine, oxymorphine, levorphanol, levallorphan, oxycodone, codeine, dihydrocodeine, propoxyphene, nalmefene, fentanyl, hydrocodone, hydromorphone, meripidine, methadone, nalorphine, naloxone, naltrexone, buprenorphine, butorphanol, nalbuphine and pentazocine;
- non-opiate analgesics, e.g., acetaminophen, salicylates (e.g., aspirin);
- nonsteroidal anti-inflammatory drugs (NSAIDs), e.g., ibuprofen, naproxen, fenoprofen, ketoprofen, celecoxib, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin and zomepirac;
- anticonvulsants, e.g., carbamazepine, oxcarbazepine, lamotrigine, valproate, topiramate, gabapentin and pregabalin;
- antidepressants such as tricyclic antidepressants, e.g., amitriptyline, clomipramine, desipramine, imipramine and nortriptyline;
- COX-2 selective inhibitors, e.g., celecoxib, rofecoxib, parecoxib, valdecoxib, deracoxib, etoricoxib, and lumiracoxib;
- alpha-adrenergics, e.g., doxazosin, tamsulosin, clonidine, guanfacine, dexmetatomidine, modafinil, and 4-amino-6,7-dimethoxy-2-(5-methane sulfonamido-1,2,3,4-tetrahydroisoquinol-2-yl)-5-(2-pyridyl) quinazoline;
- barbiturate sedatives, e.g., amobarbital, aprobarbital, butabarbital, butabital, mephobarbital, metharbital, methohexital, pentobarbital, phenobartital, secobarbital, talbutal, theamylal and thiopental;
- tachykinin (NK) antagonist, particularly an NK-3, NK-2 or NK-1 antagonist, e.g., (αR, 9R)-7-[3,5-bis(trifluoromethyl)benzyl)]-8,9,10,11-tetrahydro-9-methyl-5-(4-methylphenyl)-7H-[1,4]diazocino[2,1-g][1,7]-naphthyridine-6-13-dione (TAK-637), 5-[[2R,3S)-2-[(1R)-1-[3,5-bis(trifluoromethylphenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy5-(trifluoromethoxy)phenyl]-methylamino]-2-phenylpiperidine (2S,3S);
- coal-tar analgesics, in particular paracetamol;
- serotonin reuptake inhibitors, e.g., paroxetine, sertraline, norfluoxetine (fluoxetine desmethyl metabolite), metabolite demethylsertraline, '3 fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine, trazodone and fluoxetine;
- noradrenaline (norepinephrine) reuptake inhibitors, e.g., maprotiline, lofepramine, mirtazepine, oxaprotiline, fezolamine, tomoxetine, mianserin, buproprion, buproprion metabolite hydroxybuproprion, nomifensine and viloxazine (Vivalan®)), especially a selective noradrenaline reuptake inhibitor such as reboxetine, in particular (S,S)-reboxetine, and venlafaxine duloxetine neuroleptics sedative/anxiolytics;
- dual serotonin-noradrenaline reuptake inhibitors, such as venlafaxine, venlafaxine metabolite O-desmethylvenlafaxine, clomipramine, clomipramine metabolite desmethylclomipramine, duloxetine, milnacipran and imipramine;
- acetylcholinesterase inhibitors such as donepezil;
- 5-HT$_3$ antagonists such as ondansetron;
- metabotropic glutamate receptor (mGluR) antagonists;
- local anaesthetic such as mexiletine and lidocaine;
- corticosteroid such as dexamethasone;
- antiarrhythimics, e.g., mexiletine and phenytoin;
- muscarinic antagonists, e.g., tolterodine, propiverine, tropsium chloride, darifenacin, solifenacin, temiverine and ipratropium;
- cannabinoids;
- vanilloid receptor agonists (e.g., resinferatoxin) or antagonists (e.g., capsazepine);
- sedatives, e.g., glutethimide, meprobamate, methaqualone, and dichloralphenazone;
- anxiolytics such as benzodiazepines,
- antidepressants such as mirtazapine,
- topical agents (e.g., lidocaine, capsacin and resiniferotoxin);
- muscle relaxants such as benzodiazepines, baclofen, carisoprodol, chlorzoxazone, cyclobenzaprine, methocarbamol and orphrenadine;
- anti-histamines or H1 antagonists;
- NMDA receptor antagonists;
- 5-HT receptor agonists/antagonists;
- PDEV inhibitors;
- Tramadol®;
- cholinergic (nicotinic) analgesics;
- alpha-2-delta ligands;
- prostaglandin E2 subtype antagonists;
- leukotriene B4 antagonists;
- 5-lipoxygenase inhibitors; and
- 5-HT$_3$ antagonists.

As used herein "combination" refers to any mixture or permutation of one or more compounds of the invention and one or more other compounds of the invention or one or more additional therapeutic agent. Unless the context makes clear otherwise, "combination" may include simultaneous or sequentially delivery of a compound of the invention with one or more therapeutic agents. Unless the context makes clear otherwise, "combination" may include dosage forms of a compound of the invention with another therapeutic agent. Unless the context makes clear otherwise, "combination" may include routes of administration of a compound of the invention with another therapeutic agent. Unless the context makes clear otherwise, "combination" may include formulations of a compound of the invention with another therapeutic agent. Dosage forms, routes of administration and pharmaceutical compositions include, but are not limited to, those described herein.

Kits-of-Parts

The present invention also provides kits that contain a pharmaceutical composition which includes one or more compounds of the invention. The kit also includes instructions for the use of the pharmaceutical composition for inhibiting the activity of voltage-gated sodium channels, preferably Na$_v$1.6, for the treatment of epilepsy, as well as other utilities as disclosed herein. Preferably, a commercial package will contain one or more unit doses of the pharmaceutical composition. For example, such a unit dose may be an amount sufficient for the preparation of an intravenous injection. It will be evident to those of ordinary skill in the art that compounds which are light and/or air sensitive may require special packaging and/or formulation. For example, packaging may be used which is opaque to light, and/or sealed from contact with ambient air, and/or formulated with suitable coatings or excipients.

Preparation of the Compounds of the Invention

The following Reaction Schemes illustrate methods to make compounds of formula (I), as individual stereoisomers, enantiomers or tautomers thereof or mixtures thereof; or as pharmaceutically acceptable salts, solvates or prodrugs thereof, as described above in the Summary of the Invention.

It is understood that one skilled in the art would be able to make in a similar manner as described below other compounds of the invention not specifically illustrated below by using the appropriate starting components and modifying the parameters of the synthesis as needed. It is also understood that simple functional group transformations (see, e.g., Larock, R. C. *Comprehensive Organic Transformations*, 2$^{nd}$ edition (Wiley, 1999) can be effected by methods known to one skilled in the art. In general, starting components may be obtained from sources such as Sigma Aldrich, Combi-Blocks, Oakwood Chemicals, Inc., Maybridge, Matrix Scientific, TCI, and Fluorochem USA, etc. or synthesized according to sources known to those skilled in the art (see, e.g., Smith, M. B. and J. March, *March's Advanced Organic Chemistry: Reactions, Mechanisms, and Structure*, 6th edition (Wiley, 2007)) or prepared as described herein.

It is also understood that in the following description, combinations of substituents and/or variables of the depicted formulae are permissible only if such contributions result in stable compounds.

It will also be appreciated by those skilled in the art that in the process described below the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (e.g., t-butyldimethylsilyl, t-butyldiphenylsilyl or trimethylsilyl), tetrahydropyranyl, benzyl, and the like. Suitable protecting groups for amino include t-butoxycarbonyl, benzyloxycarbonyl, tri methylsilylethoxymethyl and the like. Suitable protecting groups for mercapto include —C(O)—R" (where R" is alkyl, aryl or aralkyl), p-methoxybenzyl, trityl and the like. Suitable protecting groups for carboxylic acid include alkyl, aryl or arylalkyl esters.

Protecting groups may be added or removed in accordance with standard techniques, which are known to one skilled in the art and as described herein.

The use of protecting groups is described in detail in Greene, T. W. and P. G. M. Wuts, *Greene's Protective Groups in Organic Synthesis* (current edition), Wiley. The protecting group may also be a polymer resin such as a Wang resin or a 2-chlorotrityl-chloride resin.

It will also be appreciated by those skilled in the art, although such protected derivatives of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention.

The compounds of formula (I) may contain at least one asymmetric carbon atom and thus can exist as racemates, enantiomers and/or diastereoisomers. Specific enantiomers or diastereoisomers may be prepared by utilizing the appropriate chiral starting material. Alternatively, diastereoisomeric mixtures or racemic mixtures of compounds of formula (I) may be resolved into their respective enantiomers or diastereoisomers. Methods for resolution of diastereoisomeric mixtures or racemic mixtures of the compounds of formula (I), as described herein, or intermediates prepared herein, are well known in the art (e.g., E. L. Eliel and S. H. Wilen, in *Stereochemistry of Organic Compounds*; John Wiley & Sons: New York, 1994; Chapter 7, and references cited therein). Suitable processes such as crystallization (e.g., preferential crystallization, preferential crystallization in the presence of additives), asymmetric transformation of racemates, chemical separation (e.g., formation and separation of diastereomers such as diastereomeric salt mixtures or the use of other resolving agents; separation via complexes and inclusion compounds), kinetic resolution (e.g., with titanium tartrate catalyst), enzymatic resolution (e.g., lipase mediated) and chromatographic separation (e.g., HPLC with chiral stationary phase and/or with simulated moving bed technology, or supercritical fluid chromatography and related techniques) are some of the examples that may be applied (see e.g., T. J. Ward, *Analytical Chemistry*, 2002, 2863-2872).

Preparation of Compounds of Formula (I)

Compounds of formula (Ia) are compounds of formula (I) as described above in the Summary of the Invention wherein q is 1, $R^{3a}$ and $R^{3b}$ are each hydrogen, and $R^7$ is azabicyclo[2.2.1]heptanylmethyl, and r, $R^1$, $R^2$, $R^5$ and $R^6$ are each as defined in the Summary of the Invention and can be prepared by the method disclosed below in Reaction Scheme 1 wherein n is 1 to 6, each X is independently fluoro, chloro or bromo, $R^{4a}$ is bromo, $R^{4b}$ is fluoro, $R^8$ is alkyl and DPPA is diphenyl phosphoryl azide:

REACTION SCHEME 1

1.

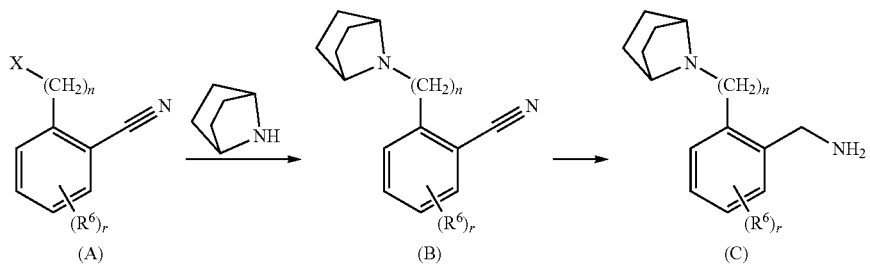

(A)  (B)  (C)

2.

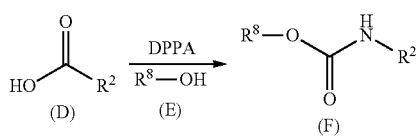

3.

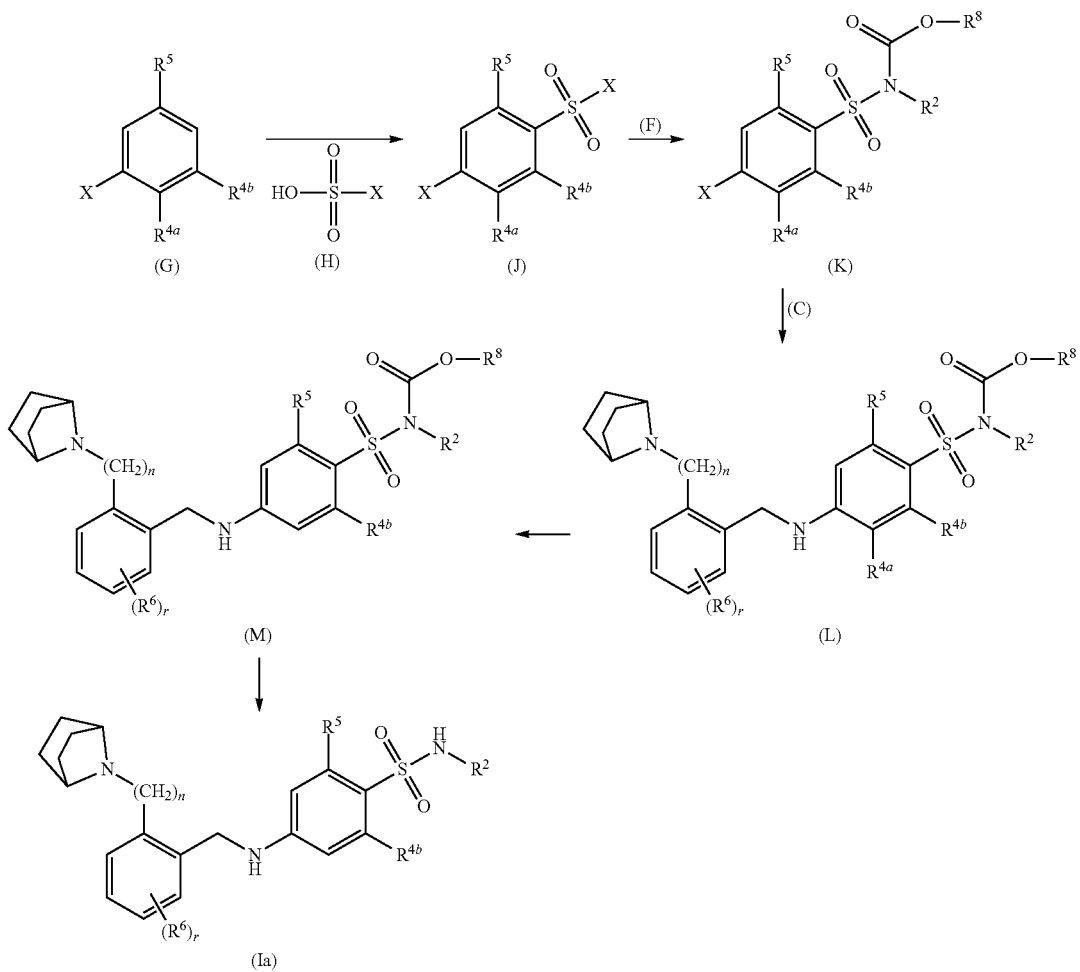

Compounds of formula (A), (B), (D), (E), (G) and (H) are commercially available or can be prepared according to methods known to one skilled in the art or by methods disclosed herein. In general, the compounds of formula (Ia) are prepared as described above in Reaction Scheme 1 as follows:

A compound of formula (A) is first treated with azabicyclo[2.2.1]heptane under standard reaction conditions, such as, but not limited to, the use of a polar aprotic solvent, such as, but not limited to, dimethyl sulfoxide, in the presence of a base, such as, but not limited to, potassium carbonate, at a temperature of between about 0° C. and 80° C., for about 1 to 48 hours to afford a compound of formula (B).

The compound of formula (B) is then treated under standard catalytic hydrogenation conditions, such as the use of Raney-Ni in the presence of ammonium hydroxide, to afford the compound of formula (C).

A compound of formula (D) is treated with an appropriate azide, such as diphenyl phosphoryl azide and a compound of formula (E) under standard Schmidt rearrangement conditions to afford a compound of formula (F).

A compound of formula (G) is treated with an excess amount of compound of formula (H) under standard arene sulfonylation conditions to afford a compound of formula (J). The compound of formula (F) is then treated with a compound of formula (J) under standard carbamate sulfonylation conditions to afford a compound of formula (K). The compound of formula (K) is then treated with a compound of formula (C) under standard nucleophilic aromatic substitution conditions, such as, but not limited to, the use of a polar aprotic solvent, such as, but not limited to, dimethyl sulfoxide, in the presence of a base, such as N,N-diisopropylethylamine, at a temperature of between about 0° C. and 80° C., for about 1 to 48 hours to afford a compound of formula (L).

The compound of formula (L) is then treated under standard arene protodehalogenation conditions to afford a compound of formula (M), which is then treated under standard nitrogen deprotection conditions to afford a compound of formula (Ia).

Compounds of formula (Ib) are compounds of formula (I) as described above in the Summary of the Invention wherein q is 1, r is 2, $R^1$ is hydrogen, $R^{3a}$ and $R^{3b}$ are each hydrogen, $R^4$ is halo, one $R^6$ is halo, one $R^6$ is alkoxy (—$OR^8$) and $R^7$ is ((methyl)(prop-2-yl)amino)methyl, and $R^2$ and $R^5$ are each as defined in the Summary of the Invention and can be prepared by the method disclosed below in Reaction Scheme 2 wherein each X is independently fluoro, chloro or bromo, $R^{6a}$ is halo and $R^8$ is alkyl:

Compounds of formula (F) are prepared in a similar manner as described above in Reaction Scheme 1. Compounds of formula (Ja) are prepared in a similar manner as described above in Reaction Scheme 1 for compounds of formula (J). Compound of formula (N) is commercially available or can be prepared according to methods known to one skilled in the art or by methods disclosed herein. In general, the compounds of formula (Ib) are prepared as described above in Reaction Scheme 2 as follows:

A compound of formula (Ja) is treated with a compound of formula (F) to afford a compound of formula (Ka) in a similar manner as described above in Reaction Scheme 1 for

REACTION SCHEME 2

1.

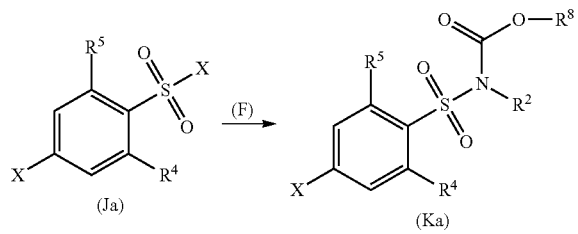

2.

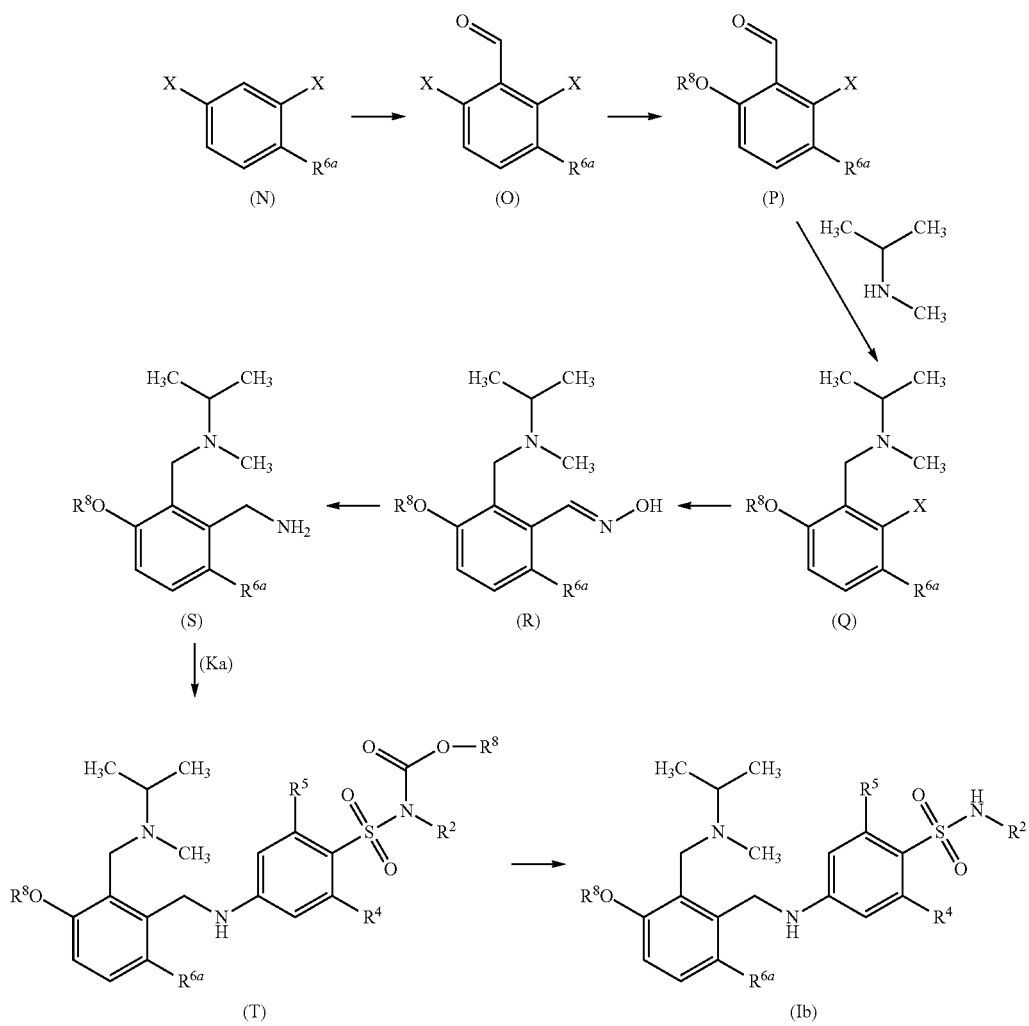

the preparation of compound of formula (K) from a compound of formula (J) and a compound of formula (F).

A compound of formula (N) is treated under standard arene formylation conditions to form the aldehyde compound of formula (O), which is then treated under standard nucleophilic aromatic substitution conditions to afford a compound of formula (P).

The compound of formula (P) is then treated under standard reductive amination conditions to afford a compound of formula (Q).

The compound of formula (Q) is then treated under standard metal-halogen exchange/formylation/oxime formation conditions to afford a compound of formula (R).

The compound of formula (R) is then treated under standard oxime reduction conditions to afford a compound of formula (S), which is then treated with a compound of formula (Ka) under standard nucleophilic aromatic substitution reaction conditions, such as, but not limited to, the use of a polar aprotic solvent, such as, but not limited to, dimethyl sulfoxide, in the presence of a base, such as N,N-diisopropylethylamine, at a temperature of between about 0° C. and 80° C., for about 1 to 48 hours to afford a compound of formula (T).

The compound of formula (T) is then treated under standard nitrogen-deprotection conditions to afford a compound of formula (Ib).

Alternatively, a compound of formula (P) where $R^8$ is methyl is treated under standard demethylation conditions, such as, but not limited to, treatment with boron tribromide, to afford the corresponding hydroxy compound, which is then treated with an alkyl halide under standard Williamson ether synthesis conditions to afford the corresponding alkoxy compound, which is then treated under the same conditions as described above from the preparation of a compound of formula (Q) to afford a compound of formula (Ib).

Compounds of formula (Ic), formula (If) and formula (Ig) are compounds of formula (I), as described above in the Summary of the Invention wherein q is 1, $R^{3a}$ and $R^{3b}$ are each hydrogen, and $R^7$ is azabicyclo[2.2.1]heptanylmethyl, and r, $R^1$, $R^2$, $R^5$ and $R^6$ are each as defined in the Summary of the Invention and can be prepared by the method disclosed below in Reaction Scheme 3 wherein n is 1 to 6, each X is independently fluoro, chloro or bromo, $R^{4d}$ is alkyl, $R^{4c}$ is chloro or fluoro and $R^8$ is alkyl:

REACTION SCHEME 3

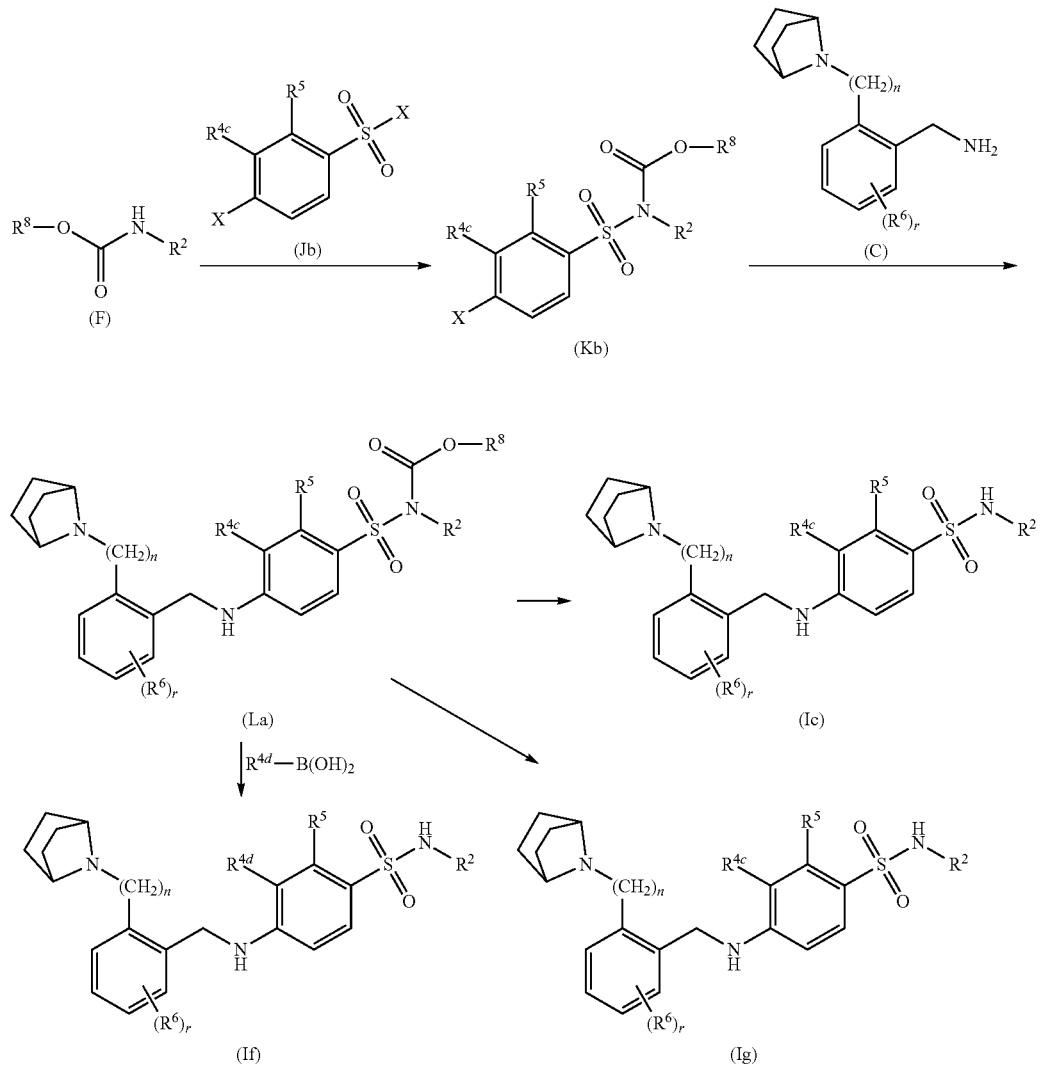

Compounds of formula (F), (Jb) and (C) can be prepared by methods disclosed herein. In general, the compounds of formula (Ia) are prepared as described above in Reaction Scheme 3 as follows:

A compound of formula (F) is treated with a compound of formula (Ja) under standard carbamate sulfonylation conditions to afford a compound of formula (Kb). The compound of formula (Kb) is then treated with a compound of formula (C) under standard nucleophilic aromatic substitution conditions, such as, but not limited to, the use of a polar aprotic solvent, such as, but not limited to, dimethyl sulfoxide, in the presence of a base, such as N,N-diisopropylethylamine, at a temperature of between about 0° C. and 80° C., for about 1 to 48 hours to afford a compound of formula (La), which is then treated under standard nitrogen deprotection conditions to afford a compound of formula (Ic).

Alternatively, compounds of formula (La) are reacted with a boronic acid derivative, such as, but not limited to, $R^{4d}$—B(OH)$_2$, under standard Suzuki-Miyaura cross coupling conditions, such as, but not limited to, the use of a solvent such as, but not limited to, 1,4-dioxane, in the presence of a base, such as, but not limited to, potassium phosphate tribasic, and in the presence of a palladium catalyst composed of, for example, but not limited to, tetrakis(triphenylphosphine)palladium(0) or palladium(II) acetate and tricyclohexylphosphine tetrafluoroborate, at a temperature of between about ambient temperature and 150° C., for about 30 minutes to 16 hours to form a product, which is then deprotected under standard nitrogen deprotection conditions to afford a compound of formula (If).

Optionally, compounds of formula (La) are treated under standard nitrogen deprotection conditions to afford a compound of formula (Ig).

Compounds of formula (Id) are compounds of formula (I) as described above in the Summary of the Invention wherein q is 2, $R^{3a}$ and $R^{3b}$ are each hydrogen, $R^7$ is azabicyclo[2.2.1]heptanylmethyl, and r, $R^1$, $R^2$, $R^5$ and $R^6$ are each as defined in the Summary of the Invention and can be prepared by the method disclosed below in Reaction Scheme 3 wherein n is 1 to 6, each X is fluoro, chloro or bromo, $R^{4d}$ is alkyl, $R^{4b}$ is fluoro and $Pg^1$ is a nitrogen-protecting group, such as 4-methoxybenzyl or 2-(trimethylsilyl)ethoxy:

REACTION SCHEME 4

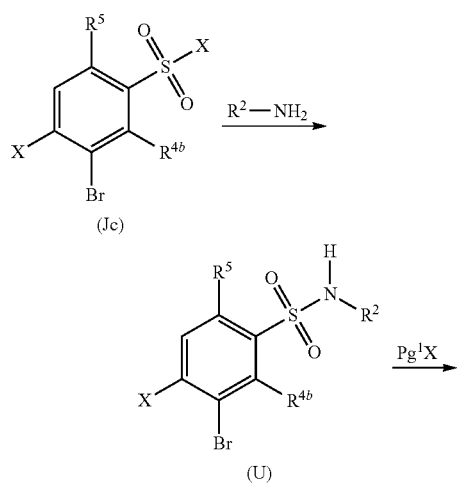

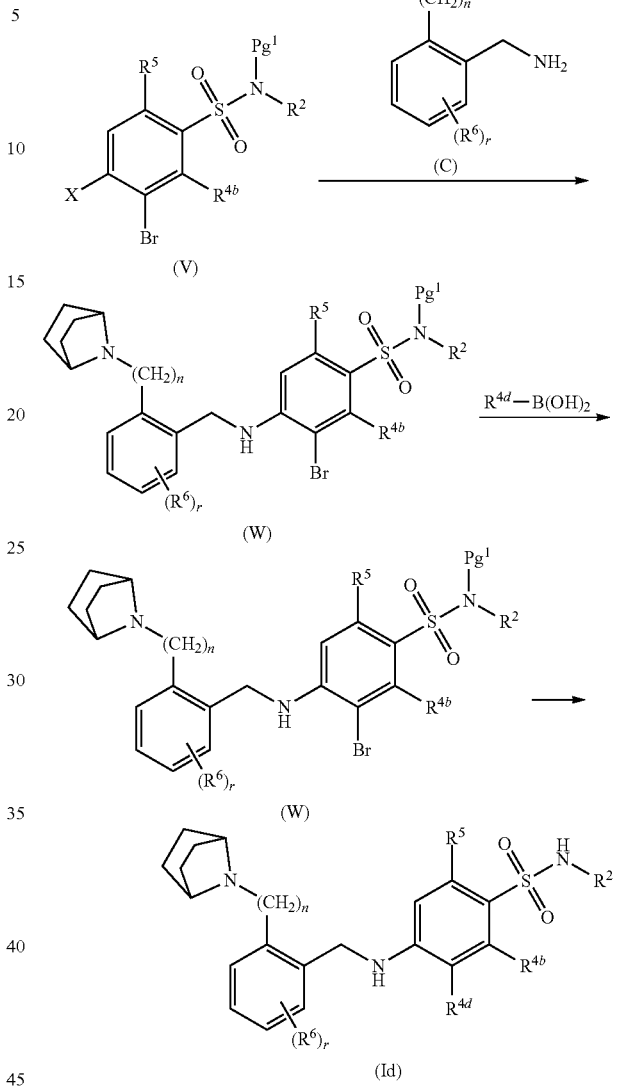

Compounds of formula (Jc) are prepared in a similar manner as described above in Reaction Scheme 1 for compounds of formula (J). Compounds of formula (C) are prepared in the manner described above in Reaction Scheme 1 for compounds of formula (C). In general, compounds of formula (Id) are prepared as described above in Reaction Scheme 4 as follows:

A compound of formula $R^2$—NH$_2$, which is commercially available or which can be prepared by methods known to one skilled in the art, is treated with a compound of formula (Jc) under standard sulfonamide formation conditions to afford a compound of formula (U).

The compound of formula (U) is the protected under standard nitrogen protection conditions to afford a compound of formula (V).

The compound of formula (V) is then treated with a compound of formula (C) under standard nucleophilic aromatic substitution conditions, such as, but not limited to, the use of a polar aprotic solvent, such as, but not limited to, dimethyl sulfoxide, in the presence of a base, such as N,N-diisopropylethylamine, at a temperature of between about 0° C. and 80° C., for about 1 to 48 hours to afford a compound of formula (W).

The compound of formula (W) is then reacted with a boronic acid derivative such as, but not limited to, $R^{4d}$—B(OH)$_2$, under standard Suzuki-Miyaura cross coupling conditions, such as, but not limited to, the use of a solvent, such as, but not limited to, 1,4-dioxane, in the presence of a base, such as, but not limited to, potassium phosphate tribasic, and in the presence of a palladium catalyst composed of, for example, but not limited to, tetrakis(triphenylphosphine)palladium(0) or palladium(II) acetate and tricyclohexylphosphine tetrafluoroborate, at a temperature of between about ambient temperature and 150° C., for about 30 minutes to 16 hours to generate a compound of formula (X), which is deprotected under standard nitrogen deprotection conditions to afford a compound of formula (Id).

Compounds of formula (Ie) are compounds of formula (I) as described above in the Summary of the Invention wherein q is 1, $R^{3a}$ and $R^{3b}$ are each hydrogen, one $R^4$ is alkyl and the other $R^4$ is halo, $R^7$ is azabicyclo[2.2.1]heptanylmethyl, and r, $R^1$, $R^2$, $R^5$ and $R^6$ are each as defined in the Summary of the Invention and can be prepared by the method disclosed below in Reaction Scheme 5 wherein n is 1 to 6, X is fluoro, chloro or bromo, $R^{4a}$ is bromo, $R^{4d}$ is alkyl, and $R^8$ is alkyl:

REACTION SCHEME 5

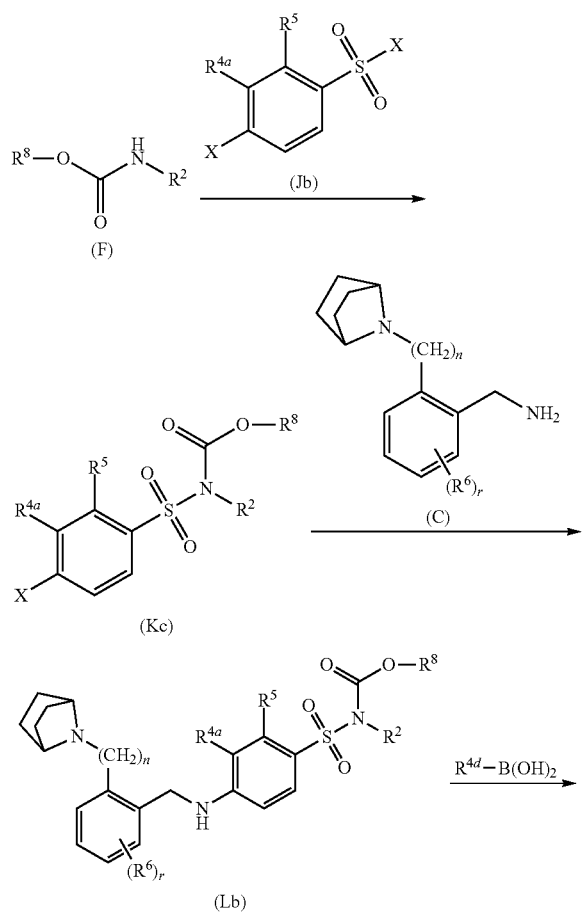

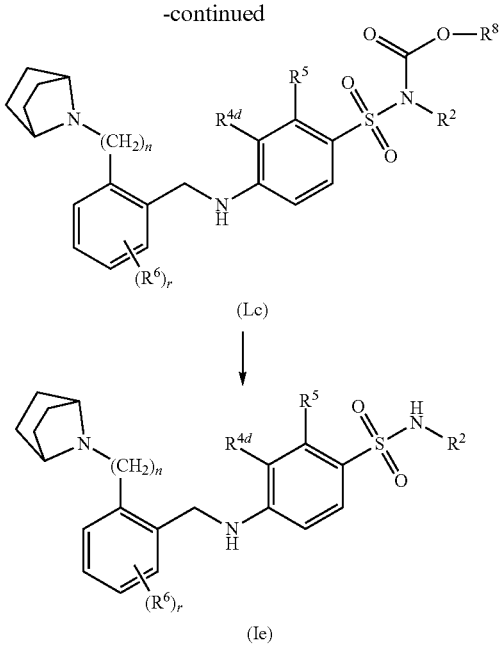

Compounds of formula (F) are prepared as described above in Reaction Scheme 1. Compounds of formula (Jb) are prepared in a similar manner as described herein for compounds of formula (J). Compounds of formula (C) as described above in Reaction Scheme 1. In general, compounds of formula (Ie) are prepared as described above in Reaction Scheme 5 as follows:

A compound of formula (F) is first treated under standard carbamate sulfonylation conditions to afford a compound of formula (Kc), which is then treated with a compound of formula (C) under standard nucleophilic aromatic substitution conditions, such as, but not limited to, the presence of a base, such, but not limited to, dimethyl sulfoxide, in the presence of a base, such as N,N-diisopropylethylamine, at ambient temperature for about 1 to 20 hours to afford a compound of formula (Lb). The compound of formula (Lb) is then reacted with a boronic acid derivative such as, but not limited to, $R^{4d}$—B(OH)$_2$, under standard Suzuki-Miyaura cross coupling conditions, such as, but not limited to, the use of a solvent, such as, but not limited to, 1,4-dioxane, in the presence of a base, such as, but not limited to, potassium phosphate tribasic, and in the presence of a palladium catalyst composed of, for example, but not limited to, tetrakis(triphenylphosphine)palladium(0) or palladium(II) acetate and tricyclohexylphosphine tetrafluoroborate, at a temperature of between about ambient temperature and 150° C., for about 30 minutes to 16 hours to generate a compound of formula (Lc), which is deprotected under standard nitrogen deprotection conditions to afford a compound of formula (Ie).

Compounds of formula (Ia) as described above in Reaction Scheme 1 are also prepared by the method disclosed below in Reaction Scheme 6 wherein q is 1, $R^{3a}$ and $R^{3b}$ are each hydrogen, and $R^7$ is azabicyclo[2.2.1]heptanylmethyl, and r, $R^1$, $R^2$, $R^5$ and $R^6$ are each as defined in the Summary of the Invention and wherein n is 1 to 6, X is fluoro, chloro or bromo, $R^{4b}$ is fluoro and $Pg^1$ is a nitrogen-protecting group, such as 4-methoxybenzyl or 2-(tri methylsilyl)ethoxy:

REACTION SCHEME 6

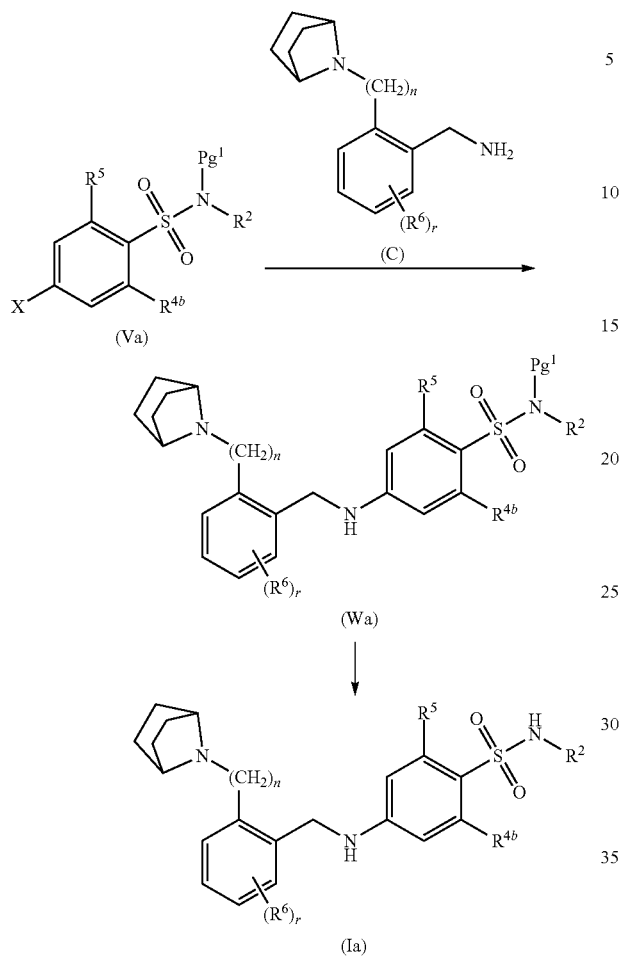

Compounds of formula (Va) can be prepared by the methods disclosed herein for compounds of formula (V) or by the methods disclosed in PCT Published Patent Application No. WO 2018/106284. Compounds of formula (C) are prepared by the methods disclosed herein. In general, compounds of formula (Ia) are prepared as described above in Reaction Scheme 6 as follows:

A compound of formula (Va) is first treated with a compound of formula (C) under standard nucleophilic aromatic substitution conditions, such as, but not limited to, the use of a polar aprotic solvent, such as, but not limited to, dimethyl sulfoxide, in the presence of a base, such as potassium carbonate, to afford a compound of formula (Wa), which is then deprotected under standard nitrogen deprotection conditions to afford a compound of formula (Ia).

Compounds of formula (Ih) are compounds of formula (I) as described above in the Summary of the Invention wherein q is 1, $R^{3a}$ and $R^{3b}$ are each hydrogen, and $R^7$ is azabicyclo[2.2.1]heptanylmethyl and r, $R^1$, $R^2$, $R^5$ and $R^6$ are each as defined in the Summary of the Invention and are prepared as described below in Reaction Scheme 7 wherein m is 0 to 5, each X is independently fluoro, chloro or bromo, $R^{4b}$ is fluoro and $R^9$ is hydrogen or methyl, and $Pg^1$ is a nitrogen-protecting group, such as 4-methoxybenzyl or 2-(trimethylsilyl)ethoxy:

REACTION SCHEME 7

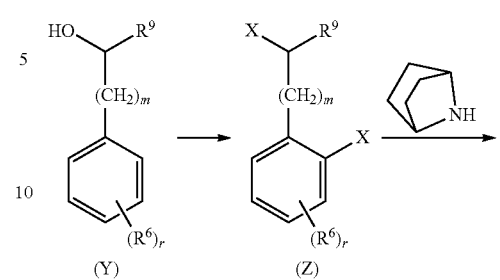

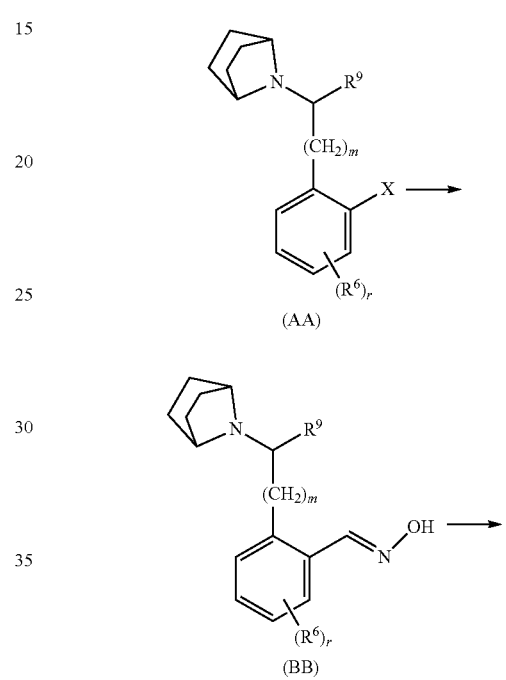

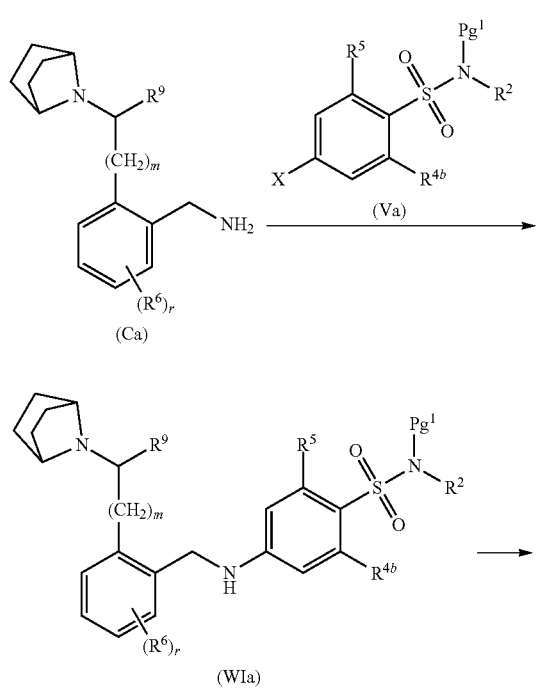

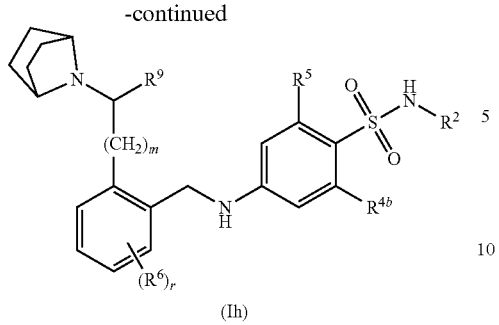

(Ih)

Compounds of formula (Y) are commercially available or can be prepared by methods known to one skilled in the art. Compounds of formulae (C) and (Va) are prepared by methods described herein or by methods known to one skilled in the art. In general, compounds of formula (Ih) are prepared as described above in Reaction Scheme 7 as follows:

A compound of formula (Y) is first treated with a brominating agent under standard Appel reaction conditions to afford a compound of formula (Z), which is then treated with azabicyclo[2.2.1]heptane under standard reaction conditions, such as, but not limited to, the use of a polar aprotic solvent, such as, but not limited to, dimethyl sulfoxide, in the presence of a base, such as, but not limited to, potassium carbonate, at a temperature of between about 0° C. and 80° C., for about 1 to 48 hours to afford a compound of formula (AA). The compound of formula (AA) is then treated under standard metal-halogen exchange/formylation/oxime formation conditions to afford a compound of formula (BB), which is then treated under standard oxime reduction conditions to afford a compound of formula (Ca). The compound of formula (Ca) is then treated with a compound of formula (Va) under standard nucleophilic aromatic substitution conditions, such as, but not limited to, the use of a polar aprotic solvent, such as, but not limited to, dimethyl sulfoxide, in the presence of a base, such as N,N-diisopropylethylamine, at a temperature of between about 0° C. and 80° C., for about 1 to 48 hours to afford a compound of formula (Wb), which is then treated under standard nitrogen deprotection conditions to afford a compound of formula (Ih).

Compounds of formula (Ih) where $R^8$ is methyl are further treated under standard chiral resolution conditions, preferably by preparative supercritical fluid chromatography, to afford the individual enantiomers.

Compounds of formula (Ii) are compounds of formula (I) as described above in the Summary of the Invention wherein q is 1, r is 2, $R^{3a}$ and $R^{3b}$ are each hydrogen, and $R^7$ is ((methyl)(prop-2-yl)amino)methyl, and $R^1$, $R^2$, and $R^5$ are each as defined in the Summary of the Invention, and are prepared as described below in Reaction Scheme 8 wherein X is independently fluoro, chloro or bromo, $R^{4c}$ is chloro or bromo, $R^{6a}$ is halo and $R^8$ is alkyl:

REACTION SCHEME 8

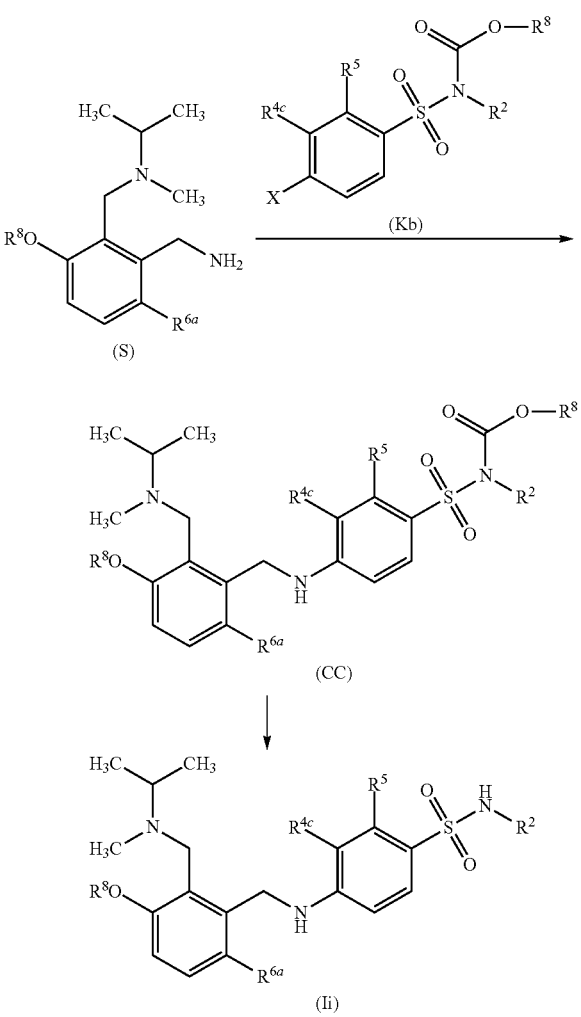

Compounds of formulae (S) and (Kb) are prepared as disclosed herein. In general, compounds of formula (Ii) are prepared as described above in Reaction Scheme 8 as follows:

A compound of formula (S) is first treated with a compound of formula (Kb) under standard nucleophilic aromatic substitution reaction conditions, such as, but not limited to, the use of a polar aprotic solvent, such as, but not limited to, dimethyl sulfoxide, in the presence of a base, such as N,N-diisopropylethylamine, at a temperature of between about 0° C. and 80° C., for about 1 to 48 hours to afford a compound of formula (CC), which is then treated under standard nitrogen-deprotection conditions to afford a compound of formula (Ii).

Compounds of formula (Ij) and formula (Ik) are compounds of formula (I) as described above in the Summary of the Invention wherein q is 1, r is 2, $R^{3a}$ and $R^{3b}$ are each hydrogen, and $R^7$ is ((methyl)(prop-2-yl)amino)methyl, and $R^1$, $R^2$, and $R^5$ are each as defined in the Summary of the Invention, and are prepared as described below in Reaction Scheme 8 wherein X is independently fluoro, chloro or bromo, $R^{4c}$ is chloro or bromo, $R^{4d}$ is alkyl, $R^{6a}$ is halo and $R^8$ is alkyl:

REACTION SCHEME 9

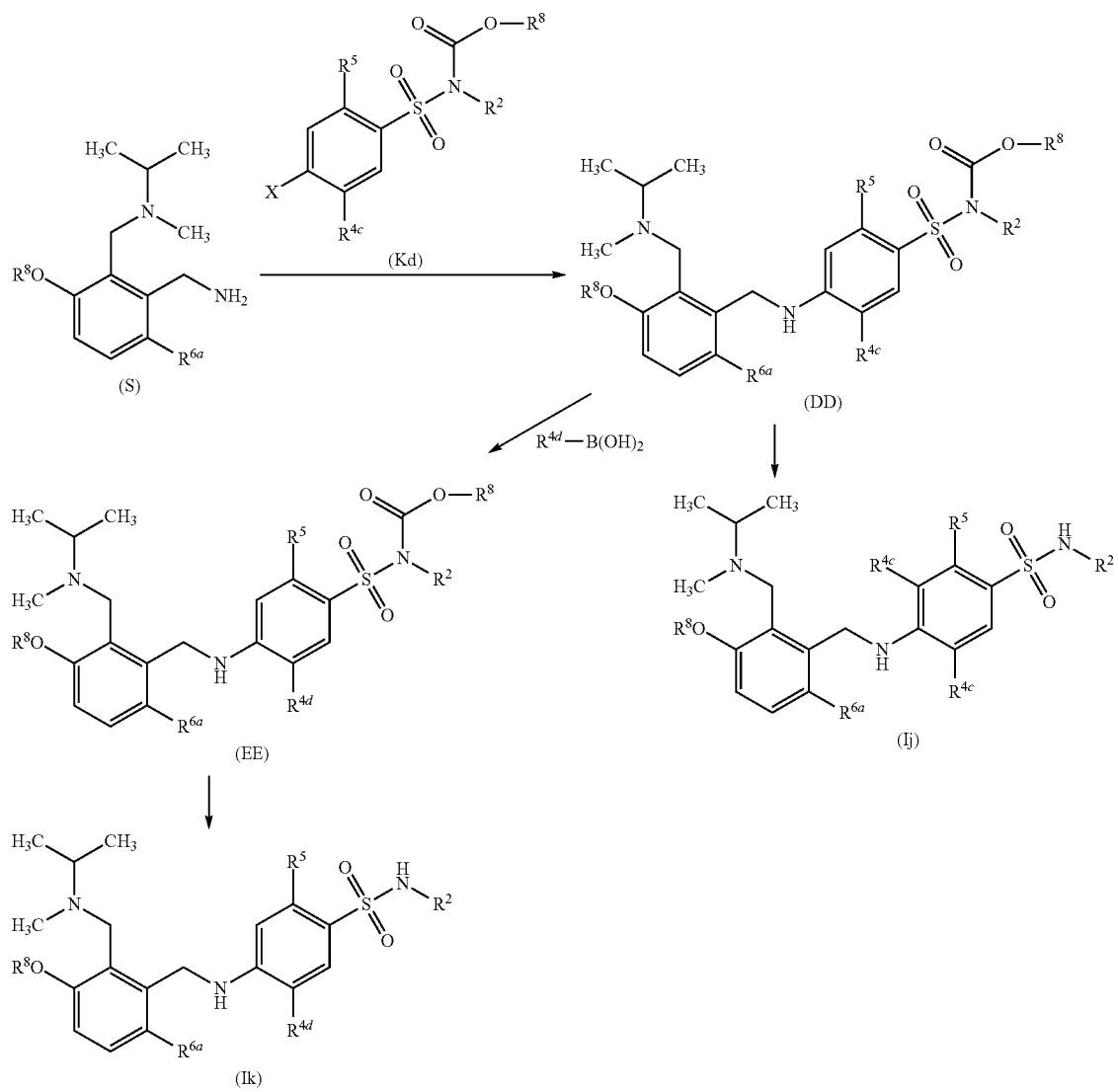

Compounds of formulae (S) and (Kd) are prepared by methods similar to those described herein. In general, compounds of formula (Ij) are prepared as described above in Reaction Scheme 9 as follows:

A compound of formula (S) is first treated with a compound of formula (Kd) under standard nucleophilic aromatic substitution reaction conditions, such as, but not limited to, the use of a polar aprotic solvent, such as, but not limited to, dimethyl sulfoxide, in the presence of a base, such as N,N-diisopropylethylamine, at a temperature of between about 0° C. and 80° C., for about 1 to 48 hours to afford a compound of formula (DD), which is then treated under standard nitrogen-deprotection conditions to afford a compound of formula (Ij).

Alternatively, a compound of formula (DD) is reacted with a boronic acid derivative, such as, but not limited to, $R^{4d}$—B(OH)$_2$, under standard Suzuki-Miyaura cross coupling conditions, such as, but not limited to, the use of a solvent such as, but not limited to, 1,4-dioxane, in the presence of a base, such as, but not limited to, potassium phosphate tribasic, and in the presence of a palladium catalyst composed of, for example, but not limited to, tetrakis(triphenylphosphine)palladium(0) or palladium(II) acetate and tricyclohexylphosphine tetrafluoroborate, at a temperature of between about ambient temperature and 150° C., for about 30 minutes to 16 hours to afford a compound of formula (EE), which is then deprotected under standard nitrogen deprotection conditions to afford a compound of formula (Ik).

All of the compounds described below as being prepared which may exist in free base or acid form may be converted to their pharmaceutically acceptable salts by treatment with the appropriate inorganic or organic base or acid. Salts of the compounds prepared below may be converted to their free base or acid form by standard techniques. Furthermore, all compounds of the invention which contain an acid or an ester group can be converted to the corresponding ester or acid, respectively, by methods known to one skilled in the art or by methods described herein.

The following Examples, which are directed to the synthesis of the compounds of the invention, and the following Biological Examples are provided as a guide to assist in the practice of the invention, and are not intended as a limitation on the scope of the invention.

In the Examples below, unless otherwise indicated all temperatures are set forth in degrees Celsius. Commercially available reagents were purchased from suppliers such as Aldrich Chemical Company, Combi-Blocks, TCI or Oakwood Chemicals and were used without further purification unless otherwise indicated. The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried. Yields were not optimized. Melting points were determined on a Büchi hot-stage apparatus and are uncorrected. $^1$H NMR, $^{19}$F and $^{13}$C NMR data were obtained in deuterated CDCl$_3$, DMSO-d$_6$, CD$_3$OD, CD$_3$CN, or acetone-d$_6$ solvent solutions with chemical shifts (δ) reported in parts-per-million (ppm) relative to trimethylsilane (TMS) or the residual non-deuterated solvent peaks as the reference standard. Data are reported as follows, if applicable: chemical shift, multiplicity, coupling constant in Hz, and number of protons, fluorine or carbon atoms. When peak multiplicities are reported, the following abbreviates are used: s (singlet), d (doublet), t (triplet), q (quartet), m (multiplet, br (broadened), dd (doublet of doublets), dt (doublet of triplets). Coupling constants, when given, are reported in Hz (Hertz).

Example 1

Synthesis of 4-((2-((7-azabicyclo[2.2.1]heptan-7-yl)methyl)-6-fluorobenzyl)amino)-2,6-difluoro-N-(isothiazol-3-yl)benzenesulfonamide

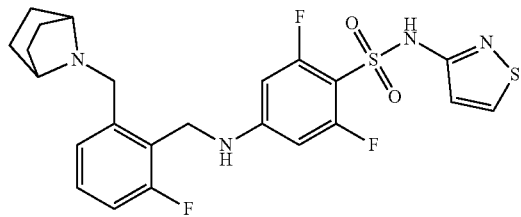 [SMILES: O=S(=O)(Nc1ccsn1)c1c(F)cc(NCc2c(F)cccc2CN2C3CCC2CC3)cc1F]

Step 1. Preparation of 2-((7-azabicyclo[2.2.1]heptan-7-yl)methyl)-6-fluorobenzonitrile

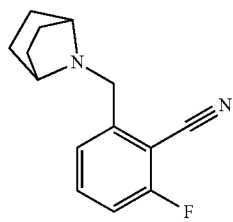 [SMILES: N#Cc1c(F)cccc1CN1C2CCC1CC2]

To a solution of 2-(bromomethyl)-6-fluorobenzonitrile (6.95 g, 32.5 mmol) and 7-azabicyclo[2.2.1]heptane hydrochloride (4.35 g, 32.5 mmol) in anhydrous dimethyl sulfoxide (60 mL) was added potassium carbonate (9.0 g, 65.2 mmol). The resulting suspension was stirred at ambient temperature for 12 h. The mixture was then diluted with ethyl acetate (400 mL) and water (100 mL). The aqueous layer was separated and extracted with ethyl acetate (2×100 mL). The combined organic layers were washed with brine (3×100 mL), dried over anhydrous sodium sulfate, filtered and the filtrate concentrated in vacuo. The residue was purified by column chromatography, eluting with a gradient of 0 to 5% methanol in dichloromethane, to yield the title compound as a yellow oil (6.40 g, 86% yield): MS (ES+) m/z 231.2 (M+1).

Step 2. Preparation of (2-((7-azabicyclo[2.2.1]heptan-7-yl)methyl)-6-fluorophenyl)methanamine

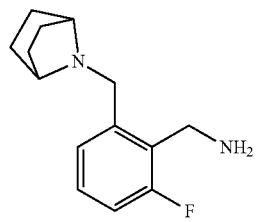 [SMILES: NCc1c(F)cccc1CN1C2CCC1CC2]

To a suspension of 2-((7-azabicyclo[2.2.1]heptan-7-yl)methyl)-6-fluorobenzonitrile (6.40 g, 189 mmol) and Raney-Ni (3 mL of a ~50% w/w aqueous slurry) in methanol (210 mL) was added 30% aqueous ammonium hydroxide (7.5 mL). The suspension was degassed under vacuum and purged with hydrogen several times. The reaction mixture was then stirred under hydrogen atmosphere (1 atm) at ambient temperature for 12 h. The reaction mixture was filtered through celite and the filtrate was concentrated in vacuo. The residue was dissolved in dichloromethane (250 mL) and the solution was dried over anhydrous sodium sulfate. Filtration and concentration of the filtrate in vacuo provided a residue which was further dried by azeotropic distillation with toluene (2×50 mL), to afford the title compound as a brown syrup (6.70 g, quantitative yield) which was used without further purification: $^1$H NMR (300 MHz, CDCl$_3$) δ 7.09 (q, J=7.2 Hz, 1H), 6.95 (t, J=8.6 Hz, 2H), 3.87 (s, 2H), 3.53 (s, 2H), 3.17 (t, J=2.0 Hz, 2H), 2.09 (s, 2H), 1.72 (dd, J=0.7, 0.4 Hz, 4H), 1.28-1.25 (m, 4H); MS (ES+) m/z 235.2 (M+1).

Step 3. Preparation of Tert-Butyl Isothiazol-4-Ylcarbamate

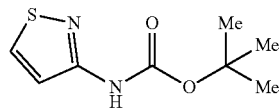 [SMILES: CC(C)(C)OC(=O)Nc1ccsn1]

To a stirred suspension of isothiazole-3-carboxylic acid (10.02 g, 77.6 mmol) in anhydrous tert-butanol (80 mL) and anhydrous toluene (120 mL) was slowly added triethylamine (13.0 mL, 93.12 mmol). The mixture was stirred at ambient temperature for 5 minutes and then diphenyl phosphoryl azide (18.42 mL, 85.36 mmol) was added dropwise to it. The reaction mixture was stirred at ambient temperature for 1 h, gradually warmed to 85° C. over 1 h, and then heated at 85° C. with stirring for 7 h. After cooling to ambient temperature, the reaction mixture was diluted with ethyl acetate (150 mL) and saturated aqueous sodium bicarbonate (150 mL). The layers were separated and the aqueous layer was extracted with ethyl acetate (2×100 mL). The combined organic layers were washed with water (150 mL), brine (150 mL), dried over magnesium sulfate, and filtered. Concentration of the filtrate in vacuo provided a residue, which was purified by column chromatography, eluting with a gradient of 0 to 10% of ethyl acetate in heptane. Further purification by column chromatography, eluting with a gradient of 0 to 10% of ethyl acetate in dichloromethane, afforded the title compound as a colorless solid (10.33 g, 66% yield): $^1$H NMR (400 MHz, CDCl$_3$) δ 8.56 (dd, J=4.9, 0.6 Hz, 1H), 8.11 (s, 1H), 7.66 (d, J=4.9 Hz, 1H), 1.53 (s, 9H); MS (ES+) m/z 201.1 (M+1).

Step 4. Preparation of
3-bromo-2,4,6-trifluorobenzenesulfonyl Chloride

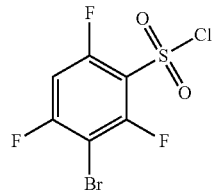 [SMILES: O=S(=O)(Cl)c1c(F)cc(F)c(Br)c1F]

To 2-bromo-1,3,5-trifluorobenzene (50.0 g, 236.0 mmol) was added chlorosulfonic acid (250 mL) and the reaction mixture was heated to 80° C. for 12 h.

After cooling to ambient temperature, the reaction mixture was poured onto ice-water and extracted with ethyl acetate (2×500 mL). The combined organic phase was dried over anhydrous sodium sulfate, filtered and the filtrate concentrated in vacuo. Purification of the residue by column chromatography, eluting with petroleum ether, provided the title compound as a yellow oil, which solidified upon standing (51.0 g, 70% yield): $^1$H NMR (400 MHz, CDCl$_3$) δ 7.03 (ddd, J=9.8, 7.8, 2.2 Hz, 1H).

Step 5. Preparation of tert-butyl ((3-bromo-2,4,6-trifluorophenyl)sulfonyl)(isothiazol-3-yl)carbamate

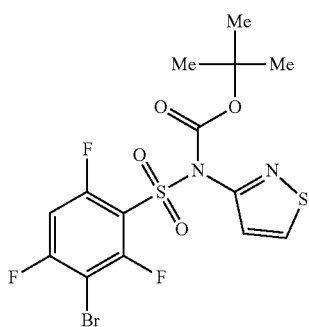 [SMILES: CC(C)(C)OC(=O)N(c1ccsn1)S(=O)(=O)c1c(F)cc(F)c(Br)c1F]

To a solution of tert-butyl isothiazol-3-ylcarbamate (6.03 g, 30.11 mmol) in anhydrous tetrahydrofuran (150 mL) was added a 1 M solution of lithium bis(trimethylsilyl)amide in tetrahydrofuran (33 mL, 33.0 mmol) at −78° C. The reaction mixture was stirred for 10 minutes at −78° C., and then allowed to warm to ambient temperature and stirred for 1 h.

After cooling the reaction mixture to −78° C., a cold (−78° C.) solution of 3-bromo-2,4,6-trifluorobenzenesulfonyl chloride (9.32 g, 30.11 mmol) in anhydrous tetrahydrofuran (150 mL) was added to it by cannula. The reaction mixture was allowed to warm to ambient temperature and stirred for 16 h. The reaction mixture was quenched by addition of saturated ammonium chloride solution (80 mL), and the aqueous layer was extracted with ethyl acetate (3×80 mL). The combined organic layers were washed with brine (100 mL), dried over magnesium sulfate, and filtered. Concentration of the filtrate in vacuo and purification of the residue by column chromatography, eluting with a gradient of 0 to 10% of ethyl acetate in heptane, provided the title compound as a colorless solid (8.35 g, 59% yield): $^1$H NMR (300 MHz, CDCl$_3$) δ 8.74 (d, J=4.7 Hz, 1H), 7.31 (d, J=4.6 Hz, 1H), 6.97 (ddd, J=9.9, 7.9, 2.1 Hz, 1H), 1.39 (s, 9H); MS (ES+) m/z 472.8 (M+1), 474.8 (M+1).

Step 6. Preparation of tert-butyl ((4-((2-((7-azabicyclo[2.2.1]heptan-7-yl)methyl)-6-fluorobenzyl) amino)-3-bromo-2,6-difluorophenyl)sulfonyl)(isothiazol-3-yl)carbamate

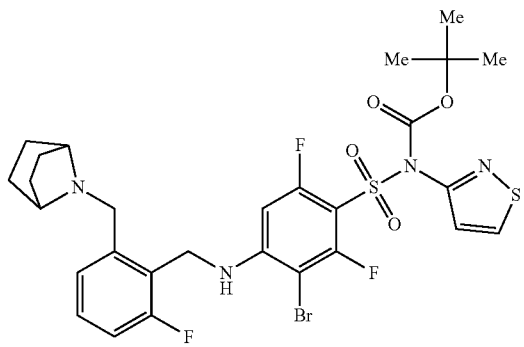 [SMILES: CC(C)(C)OC(=O)N(c1ccsn1)S(=O)(=O)c1c(F)cc(NCc2c(F)cccc2CN2C3CCC2CC3)c(Br)c1F]

To a mixture of tert-butyl ((3-bromo-2,4,6-trifluorophenyl)sulfonyl)-(isothiazol-3-yl)carbamate (10.9 g, 23.03 mmol) and (2-((7-azabicyclo[2.2.1]heptan-7-yl)methyl)-6-fluorophenyl)methanamine (5.40 g, 23.03 mmol) in anhydrous dimethyl sulfoxide (95 mL) was added N,N-diisopropylethylamine (12.00 mL, 69.09 mmol) dropwise and the reaction mixture was stirred at ambient temperature for 3 h. The reaction mixture was diluted with saturated aqueous ammonium chloride solution (80 mL), and extracted with ethyl acetate (3×100 mL). The combined organic layers were washed with brine (250 mL), dried over anhydrous magnesium sulfate, and filtered. Concentration of the filtrate in vacuo provided a residue, which was dissolved in a minimum amount of dichloromethane. To it was then added dropwise heptane until the solution became cloudy and the resulting mixture was triturated using an ultrasonication bath. The precipitate was filtered off, washed with heptane (25 mL), and dried to afford the title compound (10.4 g, 66% yield) as a colorless solid: $^1$H NMR (300 MHz, CDCl$_3$) δ 8.70 (d, J=4.6 Hz, 1H), 7.31-7.29 (m, 1H), 7.28-7.21 (m, 1H), 7.08-6.98 (m, 2H), 6.54 (dd, J=13.4, 1.7 Hz, 1H), 6.35-6.28 (m, 1H), 4.68-4.59 (m, 2H), 3.59 (s, 2H), 3.28-3.18 (m, 2H), 1.82 (br s, 4H), 1.44-1.17 (m, 13H); MS (ES+) m/z 687.2 (M+1), 689.2 (M+1).

Step 7. Preparation of tert-butyl ((4-((2-((7-azabicyclo[2.2.1]heptan-7-yl)methyl)-6-fluorobenzyl)amino)-2,6-difluorophenyl)sulfonyl)(isothiazol-3-yl)carbamate

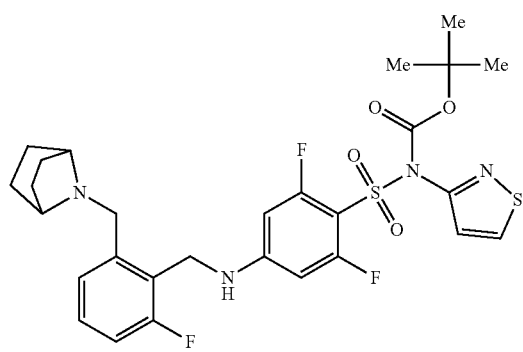 [SMILES: CC(C)(C)OC(=O)N(c1ccsn1)S(=O)(=O)c1c(F)cc(NCc2c(F)cccc2CN2C3CCC2CC3)cc1F]

To a mixture of tert-butyl ((4-((2-((7-azabicyclo[2.2.1]heptan-7-yl)methyl)-6-fluorobenzyl)amino)-3-bromo-2,6-difluorophenyl)sulfonyl)(isothiazol-3-yl)carbamate (19.22 g, 27.95 mmol) and triethylamine (39.0 mL, 279.5 mmol) in anhydrous 1,4-dioxane (280 mL) was added formic acid (5.27 mL, 139.8 mmol) and the mixture was sparged with argon for 20 minutes. To the mixture was added tetrakis(triphenylphosphine)palladium(0) (3.23 g, 2.80 mmol) and the reaction mixture was heated to 105° C. for 18 h. After cooling to ambient temperature, the mixture was concentrated in vacuo. The residue was diluted with ethyl acetate (250 mL) and saturated aqueous sodium bicarbonate solution (150 mL). The layers were separated and the aqueous layer was extracted with ethyl acetate (2×100 mL). The combined organic layers were filtered through a pad of celite. The filtrate was washed with brine (150 mL) and dried over magnesium sulfate. Filtration and concentration of the filtrate in vacuo provided a residue, which was triturated in ethanol (150 mL). The obtained solid was filtered off and purified by column chromatography, eluting with a gradient of 0 to 20% of methanol in dichloromethane, to afford the title compound as colorless solid (8.81 g, 52% yield): MS (ES+) m/z 609.2 (M+1).

Step 8. Preparation of 4-((2-((7-azabicyclo[2.2.1]heptan-7-yl)methyl)-6-fluorobenzyl)amino)-2,6-difluoro-N-(isothiazol-3-yl)benzenesulfonamide

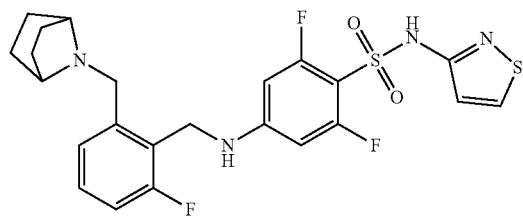 [SMILES: O=S(=O)(Nc1ccsn1)c1c(F)cc(NCc2c(F)cccc2CN2C3CCC2CC3)cc1F]

To tert-butyl ((4-((2-((7-azabicyclo[2.2.1]heptan-7-yl)methyl)-6-fluorobenzyl)amino)-2,6-difluorophenyl)sulfonyl)(isothiazol-3-yl)carbamate (8.81 g, 14.47 mmol) was added ethanol (360 mL) and water (180 mL) and the reaction mixture was heated to reflux for 5 h. After cooling to ambient temperature, the reaction mixture was concentrated in vacuo. The residue was dissolved in hot ethanol and the obtained solution was concentrated in vacuo. The residue was triturated with ethanol to provide the title compound as colorless solid (7.098 g, 96% yield): $^1$H NMR (300 MHz, DMSO-$d_6$) δ 11.61 (s, 1H), 8.90 (d, J=4.7 Hz, 1H), 7.41-7.29 (m, 2H), 7.24-7.21 (m, 1H), 7.18-7.10 (m, 1H), 6.91 (d, J=4.8 Hz, 1H), 6.40-6.31 (m, 2H), 4.47-4.31 (m, 2H), 3.53 (s, 2H), 3.11 (s, 2H), 1.75-1.52 (m, 4H), 1.32-1.12 (m, 4H); $^{13}$C NMR (151 MHz, DMSO) δ 160.9, 160.6, 157.2, 153.5, 150.6, 141.7, 129.3, 125.7, 123.3, 114.2, 114.1, 102.7, 94.8, 58.8, 48.6, 36.9, 27.9; $^{19}$F NMR (565 MHz, DMSO) δ –108.5, –117.7; MS (ES+) m/z 509.0 (M+1).

Example 2

Synthesis of 2,6-difluoro-4-((6-fluoro-2-((isopropyl(methyl)amino)methyl)-3-methoxybenzyl)amino)-N-(thiazol-4-yl)benzenesulfonamide

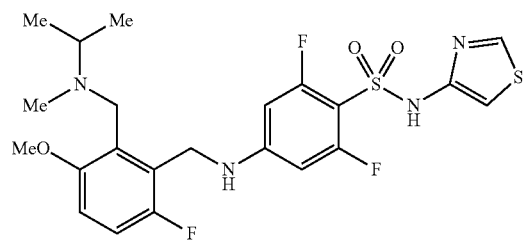 [SMILES: COc1ccc(F)c(CNc2cc(F)c(S(=O)(=O)Nc3cscn3)c(F)c2)c1CN(C)C(C)C]

Step 1. Preparation of Tert-Butyl Thiazol-4-ylcarbamate

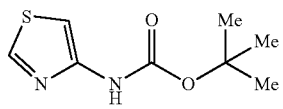 [SMILES: CC(C)(C)OC(=O)Nc1cscn1]

To a solution of thiazole-4-carboxylic acid (150.0 g, 1.16 mol) in anhydrous tert-butanol (1000 mL) was slowly added triethylamine (156.7 g, 1.55 mol) and diphenyl phosphoryl azide (383.6 g, 1.39 mol). The reaction mixture was stirred at ambient temperature for 0.5 h and then heated to 90° C. for 3 h. After cooling to ambient temperature, the reaction mixture was concentrated under reduced pressure. The obtained residue was diluted with petroleum ether (1000 mL) and water (1000 mL), and the mixture was stirred at ambient temperature for 12 h. The mixture was filtered and the filter cake was extracted with ethyl acetate (3×1000 mL). The combined organic phase was washed with brine (3×1000 mL), dried over anhydrous sodium sulfate, and filtered. Concentration of the filtrate provided a residue which was triturated with methanol (200 mL) to give the title compound as a yellowish solid (100.0 g, 43% yield): $^1$H NMR (400 MHz, CDCl$_3$) δ 89.92 (br s, 1H), 8.65 (d, J=2.4 Hz, 1H), 7.35 (br s, 1H), 1.57 (s, 9H); MS (ES+) m/z 223.0 (M+23).

Step 2. Preparation of tert-butyl thiazol-4-yl((2,4,6-trifluorophenyl)sulfonyl)carbamate

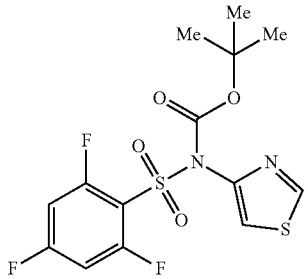 [SMILES: CC(C)(C)OC(=O)N(c1cscn1)S(=O)(=O)c1c(F)cc(F)cc1F]

To a solution of tert-butyl thiazol-4-ylcarbamate (140.0 g, 699.1 mmol) in anhydrous tetrahydrofuran (700 mL) was added a 1 M solution of lithium bis(trimethylsilyl)amide in tetrahydrofuran (758.9 mL, 758.9 mmol) at −78° C. The reaction mixture was allowed to warm to 0° C. and stirred for 20 minutes. After cooling the reaction mixture to −78° C., a solution of 2,4,6-trifluorobenzenesulfonyl chloride (175.0 g, 758.9 mmol) in anhydrous tetrahydrofuran (200 mL) was slowly added to it. The reaction mixture was allowed to warm to ambient temperature, stirred for 12 h, and then quenched by addition of saturated aqueous ammonium chloride (200 mL). The mixture was extracted with ethyl acetate (3×1000 mL). The organic phase was washed with brine (3×1000 mL), dried over anhydrous sodium sulfate, and filtered. Concentration in vacuo and trituration of the residue in methanol (100 mL) provided the title compound as a colorless solid (140.0 g, 58% yield): $^1$H NMR (400 MHz, CDCl$_3$) δ 8.81 (d, J=2.1 Hz, 1H), 7.53 (d, J=2.1 Hz, 1H), 6.85 (br t, J=8.4 Hz, 2H), 1.39 (s, 9H); MS (ES+) m/z 417.0 (M+23).

Step 3. Preparation of 2-bromo-3,6-difluorobenzaldehyde

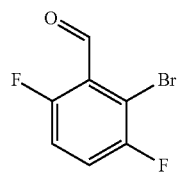

To a solution of 2-bromo-1,4-difluorobenzene (100 g, 518 mmol) in anhydrous tetrahydrofuran (500 mL) was added a solution of lithium diisopropylamide (61.1 g, 570 mmol) in anhydrous tetrahydrofuran (100 mL) over 30 minutes at −78° C. The reaction mixture was then stirred at −78° C. for 1 h, and N,N-dimethylformamide (45.5 g, 622 mmol) was added to it. The reaction mixture was stirred at −78° C. for 30 minutes, and then quenched by addition of saturated aqueous ammonium chloride (200 mL). The mixture was allowed to warm to ambient temperature and extracted with ethyl acetate (500 mL). The combined extracts were dried over anhydrous sodium sulfate, filtered, and the filtrate was concentrated in vacuo. Purification of the residue by column chromatography, eluting with 5% of ethyl acetate in petroleum ether, provided the title compound as a colorless oil (69.0 g, 60% yield): $^1$H NMR (400 MHz, CDCl$_3$) δ 10.35-10.20 (m, 1H), 7.27 (ddd, J=9.2, 7.4, 4.4 Hz, 1H), 7.08 (dt, J=9.2, 4.0, Hz, 1H).

Step 4. Preparation of 2-bromo-3-fluoro-6-methoxybenzaldehyde

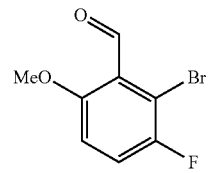

To anhydrous methanol (750 mL) was slowly added sodium metal (8.62 g, 375 mmol) in several portions over the course of 1 h. After the last addition, the mixture was stirred for additional 10 minutes until all sodium was dissolved. To the mixture was then added 2-bromo-3,6-difluorobenzaldehyde (75.0 g, 341 mmol) and the reaction mixture was heated to reflux for 20 h. After cooling to ambient temperature, the reaction mixture was concentrated in vacuo. The residue was dissolved in ethyl acetate (800 mL) and washed with saturated aqueous ammonium chloride solution (2×400 mL). The aqueous layers were extracted with ethyl acetate (2×100 mL). The combined organic layers were washed with brine (2×100 mL), dried over anhydrous magnesium sulfate, and filtered. Concentration of the filtrate in vacuo yielded a waxy yellow solid that was used without further purification (82.6 g, quantitative yield): $^1$H NMR (300 MHz, CDCl$_3$) δ 10.39 (d, J=0.8 Hz, 1H), 7.32-7.28 (m, 1H), 6.95 (dd, J=9.2, 3.8 Hz, 1H), 3.94 (s, 3H).

Step 5. Preparation of N-(2-bromo-3-fluoro-6-methoxybenzyl)-N-methylpropan-2-amine

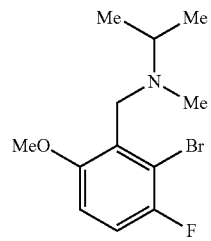 [SMILES: COc1ccc(F)c(Br)c1CN(C)C(C)C]

To a flask charged with 2-bromo-3-fluoro-6-methoxybenzaldehyde (82.6 g, 354.4 mmol) were added anhydrous dichloromethane (1500 mL), glacial acetic acid (1 mL), and N-methylpropan-2-amine (40 g, 459 mmol). The reaction flask was placed in a water bath at 21° C., and sodium cyanoborohydride (13.35 g, 212.6 mmol) was added to the reaction mixture in 5 portions (2.67 g), waiting 30 minutes between each addition. After stirring the reaction mixture at ambient temperature for 8 h, more N-methylpropan-2-amine (7.0 g, 96.0 mmol) was added to it. The reaction mixture was stirred at ambient temperature for a further 16 h, and then quenched by addition of 1 M sodium hydroxide solution (200 mL). The layers were separated, and the volume of the organic phase was reduced by half in vacuo. The remaining organic phase was washed with 1 M sodium hydroxide solution (200 mL), brine (200 mL), and dried over anhydrous magnesium sulfate. Filtration and concentration of the filtrate in vacuo provided a residue, which was dissolved in ethyl acetate (400 mL) and extracted with 3 M hydrochloric acid (100 mL, 50 mL, and 30 mL). The combined aqueous layers were cooled to 0° C., the pH was adjusted to pH 12 with solid sodium hydroxide, and the aqueous layer was extracted with ethyl acetate (3×200 mL). The combined organic layers were washed with 1 M sodium hydroxide solution (100 mL), brine (200 mL), and dried over anhydrous magnesium sulfate. Filtration and concentration of the filtrate in vacuo provided the title compound as a red oil (81.4 g, 79% yield), which was used without further purification: $^1$H NMR (300 MHz, CDCl$_3$) δ 7.02 (dd, J=9.0, 8.0 Hz, 1H), 6.79 (dd, J=9.0, 4.2 Hz, 1H), 3.83 (s, 3H), 3.70 (s, 2H), 3.02 (dt, J=13.2, 6.6 Hz, 1H), 2.20 (s, 3H), 1.13 (d, J=6.6 Hz, 6H).

Step 6. Preparation of (E)-6-fluoro-2-((isopropyl (methyl)amino)methyl)-3-methoxybenzaldehyde Oxime

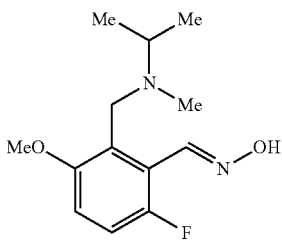 [SMILES: COc1ccc(F)c(/C=N/O)c1CN(C)C(C)C]

To a flask charged with N-(2-bromo-3-fluoro-6-methoxybenzyl)-N-methylpropan-2-amine (10.0 g, 34.5 mmol) was added anhydrous tetrahydrofuran (140 mL). The solution was cooled to an internal temperature of 0° C. using an ice-water bath. The bath was removed and a 1.3 M solution of isopropylmagnesium chloride lithium chloride complex in tetrahydrofuran (53 mL, 69 mmol) was added dropwise via an addition funnel over the course of 45 minutes. The reaction mixture was then stirred at ambient temperature for 10 minutes, and additional 1.3 M solution of isopropylmagnesium chloride lithium chloride complex in tetrahydrofuran (53 mL, 69 mmol) was added dropwise over the course of 45 minutes. The reaction mixture was stirred at ambient temperature for 30 minutes and N,N-dimethylformamide (13 mL, 172.3 mmol) was added to it. After stirring at ambient temperature for 3 h, a solution of hydroxylamine hydrochloride (14.4 g, 206.8 mmol) in water (40 mL) was added and the reaction mixture was stirred vigorously at ambient temperature for 16 h. To the reaction mixture was then added a brine/water mixture (1:1, 200 mL) and the aqueous layer was extracted with ethyl acetate (2×50 mL). The combined organic extracts were washed with brine (2×50 mL), dried over anhydrous magnesium sulfate, and filtered. Concentration of the filtrate in vacuo provided a residue which was purified by column chromatography, eluting with a gradient of 20 to 80% of ethyl acetate (containing 10% of 2-propanol and 10% of triethylamine) in heptane, to afford the title compound as a yellow wax (6.20 g, 71% yield): $^1$H NMR (300 MHz, CDCl$_3$) δ 8.51 (s, 1H), 7.00 (t, J=9.6 Hz, 1H), 6.83 (dd, J=9.1, 4.2 Hz, 1H), 3.82 (d, J=3.2 Hz, 3H), 3.69 (s, 2H), 2.89 (t, J=6.6 Hz, 1H), 2.10 (s, 3H), 1.10-1.06 (m, 6H), OH not observed.

Step 7. Preparation of N-(2-(aminomethyl)-3-fluoro-6-methoxybenzyl)-N-methylpropan-2-amine

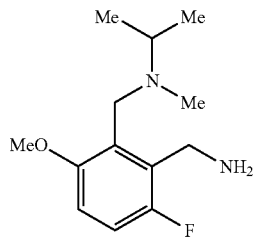 [SMILES: COc1ccc(F)c(CN)c1CN(C)C(C)C]

To a flask charged with (E)-6-fluoro-2-((isopropyl (methyl)amino)methyl)-3-methoxybenzaldehyde oxime (36.8 g, 145 mmol) was added glacial acetic acid (690 mL). To it was then added zinc powder (56 g, 868 mmol) and the reaction mixture was heated to 65° C. for 1 h. A second portion of zinc powder (56 g, 868 mmol) was added to it and the reaction mixture was heated to 65° C. for 1 h. After cooling to ambient temperature, the reaction mixture was filtered through a bed of celite, and the filter cake was washed with ethyl acetate (2×100 mL). The combined filtrate was concentrated in vacuo and the residue was dissolved in ethyl acetate (500 mL). To the organic phase was added 5 M sodium hydroxide until the aqueous layer of the mixture had reached pH 12. The aqueous layer was extracted with ethyl acetate (2×200 mL). The combined organic layers were washed with brine (200 mL), dried over anhydrous magnesium sulfate, and filtered. Concentration of the filtrate in vacuo provided the title compound as a red oil (36.4 g, quantitative yield), which was used without further purification: $^1$H NMR (300 MHz, CDCl$_3$) δ 6.95 (t, J=9.1 Hz, 1H), 6.73 (dd, J=9.0, 4.4 Hz, 1H), 3.84 (d, J=2.2 Hz, 2H), 3.79 (s, 3H), 3.67 (s, 2H), 2.99-2.83 (m, 1H), 2.47-2.42 (m, 2H), 2.08 (s, 3H), 1.08 (d, J=6.6 Hz, 6H).

Step 8. Preparation of tert-butyl ((2,6-difluoro-4-((6-fluoro-2-((isopropyl(methyl)-amino)methyl)-3-methoxybenzyl)amino)phenyl)sulfonyl)(thiazol-4-yl) carbamate

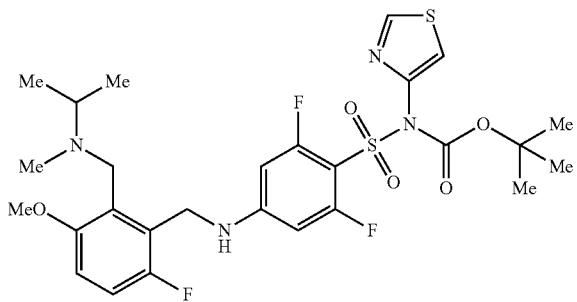 [SMILES: COc1ccc(F)c(CNc2cc(F)c(S(=O)(=O)N(C(=O)OC(C)(C)C)c3cscn3)c(F)c2)c1CN(C)C(C)C]

To a mixture of tert-butyl thiazol-4-yl((2,4,6-trifluorophenyl)sulfonyl)carbamate (26.26 g, 66.58 mmol) and N,N-diisopropylethylamine (23.2 mL, 133.2 mmol) in anhydrous dimethyl sulfoxide (190 mL) was added a solution of N-(2-(aminomethyl)-3-fluoro-6-methoxybenzyl)-N-methylpropan-2-amine (21.00 g, 87.38 mmol) in anhydrous dimethyl sulfoxide (60 mL) via a dropping funnel over 40 minutes. The reaction mixture was stirred at ambient temperature for 18 h. The mixture was then diluted with ethyl acetate (400 mL) and washed with saturated aqueous sodium bicarbonate (250 mL). The aqueous layer was extracted with ethyl acetate (200 mL). The combined organic layers were washed with saturated aqueous sodium bicarbonate (200 mL), saturated ammonium chloride (200 mL), brine (100 mL), dried over anhydrous sodium sulfate, and filtered. The filtrate was concentrated in vacuo to a total volume of approximately 150 mL and cooled to 5° C. The obtained precipitate was filtered off and washed with ethyl acetate (50 mL) to afford the title compound as a colorless solid (14.73 g, 36% yield): $^1$H NMR (300 MHz, CDCl$_3$) δ 8.79 (d, J=2.3 Hz, 1H), 8.37 (s, 1H), 7.50 (d, J=2.3 Hz, 1H), 7.02 (t, J=9.0 Hz, 1H), 6.83 (dd, J=9.2, 4.4 Hz, 1H), 6.20 (d, J=12.1 Hz, 2H), 4.35 (s, 2H), 3.82 (s, 3H), 3.70 (s, 2H), 2.99-2.85 (m, 1H), 2.13 (s, 3H), 1.40 (s, 9H), 1.13 (d, J=6.6 Hz, 6H); MS (ES+) m/z 615.2 (M+1).

Step 9. Preparation of 2,6-difluoro-4-((6-fluoro-2-((isopropyl(methyl)amino)methyl)-3-methoxybenzyl)amino)-N-(thiazol-4-yl)benzenesulfonamide

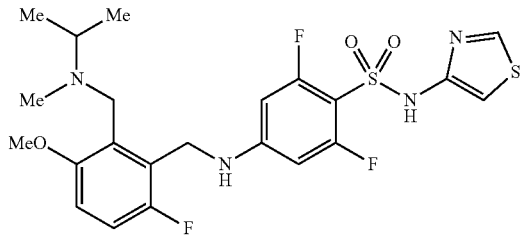 [SMILES: COc1ccc(F)c(CNc2cc(F)c(S(=O)(=O)Nc3cscn3)c(F)c2)c1CN(C)C(C)C]

To a flask containing tert-butyl ((2,6-difluoro-4-((6-fluoro-2-((isopropyl(methyl)amino)-methyl)-3-methoxybenzyl)amino)phenyl)sulfonyl)(thiazol-4-yl)carbamate (19.67 g, 32.01 mmol) was added 2-butanol (100 mL) and water (40 mL). The slurry was degassed by sparging with nitrogen for 15 minutes and then heated to reflux for 24 h. The suspension was then cooled to approximately 50° C., and diluted with ethanol (100 mL). The mixture was heated to reflux for an additional 1 h, and then cooled to 35° C. The precipitate was filtered off and rinsed with ethanol (60 mL) to afford the title compound as an off-white solid (15.09 g, 92% yield): $^1$H NMR (300 MHz, DMSO-d$_6$) δ 11.11 (s, 1H), 8.89 (d, J=2.2 Hz, 1H), 7.42 (s, 1H), 7.14 (t, J=9.2 Hz, 1H), 7.02 (dd, J=9.2, 4.6 Hz, 1H), 6.88 (d, J=2.2 Hz, 1H), 6.37 (d, J=12.7 Hz, 2H), 4.36 (s, 2H), 3.77 (s, 3H), 3.58 (s, 2H), 2.83-2.70 (m, 1H), 1.98 (s, 3H), 0.95 (d, J=6.6 Hz, 6H); MS (ES+) m/z 515.0 (M+1).

Example 3

Synthesis of 4-((2-((7-azabicyclo[2.2.1]heptan-7-yl)methyl)-6-fluorobenzyl)amino)-2,3-difluoro-N-(thiazol-4-yl)benzenesulfonamide

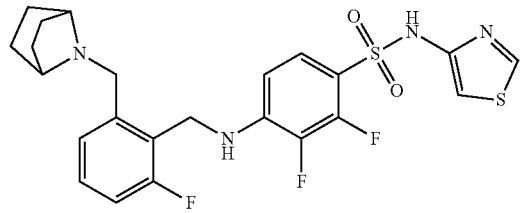 [SMILES: O=S(=O)(Nc1cscn1)c1ccc(NCc2c(F)cccc2CN2C3CCC2CC3)c(F)c1F]

Step 1. Preparation of Tert-Butyl thiazol-4-yl((2,3,4-trifluorophenyl)sulfonyl)carbamate

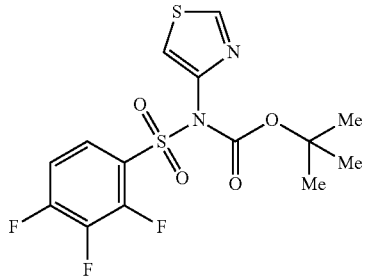 [SMILES: CC(C)(C)OC(=O)N(c1cscn1)S(=O)(=O)c1ccc(F)c(F)c1F]

To a solution of tert-butyl thiazol-4-ylcarbamate (2.87 g, 14.3 mmol) in anhydrous tetrahydrofuran 50 mL) was added a 1 M solution of lithium bis(trimethylsilyl)amide in tetrahydrofuran (14.3 mL, 14.3 mmol) at −50° C. The reaction mixture was allowed to warm to 0° C. and stirred for 1 h. After cooling the reaction mixture to 0° C., a solution of 2,3,4-trifluorobenzenesulfonyl chloride (3.0 g, 13.0 mmol) in anhydrous tetrahydrofuran (60 mL) was slowly added to the reaction mixture. The reaction mixture was allowed to warm to ambient temperature, stirred for 12 h, and then quenched by addition of saturated aqueous ammonium chloride (50 mL). The mixture was extracted with ethyl acetate (3×100 mL). The combined organic phase was washed with brine (2×50 mL), dried over anhydrous sodium sulfate, filtered and the filtrate was concentrated in vacuo. The residue was purified by column chromatography, eluting with a gradient of 0-30% of ethyl acetate in heptane, to provide the title compound as a colorless solid (4.34 g, 85% yield): $^1$H NMR (400 MHz, CDCl$_3$) δ 8.73 (d, J=2.2 Hz, 1H), 7.93-7.82 (m, 1H), 7.47 (d, J=2.4 Hz, 1H), 7.11 (ddt, J=2.2, 6.8, 9.0 Hz, 1H), 1.29 (s, 9H); MS (ES+) m/z 295.0 (M−99).

Step 2. Preparation of tert-butyl ((4-((2-((7-azabicyclo[2.2.1]heptan-7-yl)methyl)-6-fluorobenzyl) amino)-2,3-difluorophenyl)sulfonyl)(thiazol-4-yl) carbamate

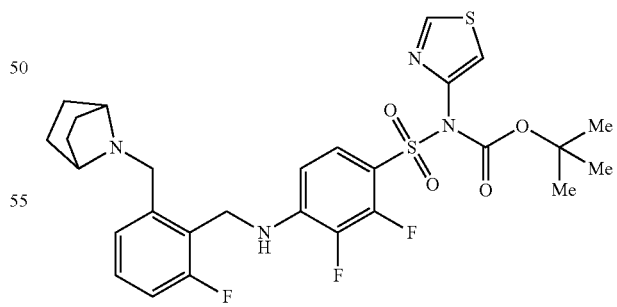

To a solution of (2-((7-azabicyclo[2.2.1]heptan-7-yl) methyl)-6-fluorophenyl)methanamine (1.19 g, 5.08 mmol) and tert-butyl thiazol-4-yl((2,3,4-trifluorophenyl)sulfonyl) carbamate (1.82 g, 4.62 mmol) in anhydrous dimethyl sulfoxide (35 mL) was added N,N-diisopropylethylamine (2.4 mL, 13.9 mmol)). The reaction mixture was stirred at ambient temperature for 3 h. The reaction mixture was then added dropwise to a rapidly stirring aqueous ammonium chloride solution (500 mL) and the obtained precipitate was filtered off. The precipitate was dissolved in ethyl acetate (250 mL) with washed with brine (2×50 mL), dried over anhydrous sodium sulfate and filtered. Concentration of the filtrate in vacuo and purification of the residue by column chromatography, eluting with a gradient of 0 to 35% of ethyl acetate (containing 10% of 2-propanol and 10% of trimethylamine) in heptane, provided the title compound as a colourless solid (1.09 g, 39% yield): MS (ES+) m/z 609.1 (M+1).

Step 3. Preparation of 4-((2-((7-azabicyclo[2.2.1]heptan-7-yl)methyl)-6-fluorobenzyl)amino)-2,3-difluoro-N-(thiazol-4-yl)benzenesulfonamide

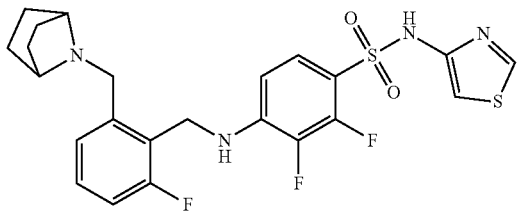 [SMILES: O=S(=O)(Nc1cscn1)c1ccc(NCc2c(F)cccc2CN2C3CCC2CC3)c(F)c1F]

To a suspension of tert-butyl ((4-((2-((7-azabicyclo[2.2.1]heptan-7-yl)methyl)-6-fluorobenzyl)amino)-2,3-difluorophenyl)sulfonyl)(thiazol-4-yl)carbamate (1.09 g, 1.79 mmol) in water (20 mL) was added ethanol (40 mL) and the reaction mixture was heated to 80° C. for 8 h. The reaction mixture was filtered hot through a pad of celite and then concentrated in vacuo to provide a wet slurry. To this was added ethanol (750 mL) and the mixture was heated until a clear solution was obtained. Concentration in vacuo provided a residue which was redissolved in ethanol (750 mL). Concentration in vacuo provided a residue was triturated with a minimal amount of ethanol to provide the title compound as a colourless solid (0.85 g, 93% yield): $^1$H NMR (300 MHz, DMSO-d$_6$) δ 11.13-11.12 (m, 1H), 8.87 (d, J=2.2 Hz, 1H), 7.46-7.40 (m, 1H), 7.32 (td, J=7.8, 5.9 Hz, 1H), 7.18-7.12 (m, 3H), 6.96 (d, J=2.2 Hz, 1H), 6.92-6.86 (m, 1H), 4.52-4.51 (m, 2H), 3.59 (s, 2H), 3.15 (s, 2H), 1.72-1.69 (m, 4H), 1.26 (d, J=6.7 Hz, 4H); $^{19}$F NMR (565 MHz, DMSO-d$_6$) δ –116.6, –137.9, –160.7; MS (ES+) m/z 509.0 (M+1), 510.0 (M+1).

Example 4

Synthesis of 4-((2-((7-azabicyclo[2.2.1]heptan-7-yl)methyl)-6-fluorobenzyl)amino)-2,6-difluoro-N-(isoxazol-3-yl)-3-methylbenzenesulfonamide

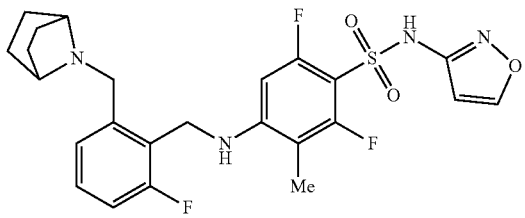 [SMILES: Cc1c(NCc2c(F)cccc2CN2C3CCC2CC3)cc(F)c(S(=O)(=O)Nc2ccon2)c1F]

Step 1. Preparation of 3-bromo-2,4,6-trifluoro-N-(isoxazol-3-yl)benzenesulfonamide

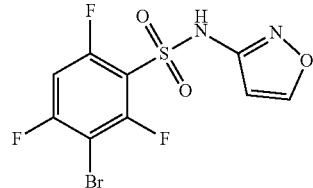 [SMILES: O=S(=O)(Nc1ccon1)c1c(F)cc(F)c(Br)c1F]

To a mixture of isoxazol-3-amine (3.96 g, 47.2 mmol), 4-(dimethylamino)-pyridine (1.10 g, 9.00 mmol) and pyridine (9.09 mL, 112.5 mmol) in anhydrous dichloromethane (40 mL) was added a solution of 3-bromo-2,4,6-trifluorobenzene-1-sulfonyl chloride (14.0 g, 45.0 mmol) in anhydrous dichloromethane (50 mL) at 0° C. The reaction mixture was stirred at 0° C. for 0.5 h and at ambient temperature for 12 h. After concentration in vacuo, the residue was purified by column chromatography, eluting with a gradient of 30 to 80% of ethyl acetate in heptane, to yield the title compound as a colourless solid (6.65 g, 40% yield): $^1$H NMR (400 MHz, CDCl$_3$) δ 8.31 (d, J=1.8 Hz, 1H), 6.94 (ddd, J=10.0, 7.8, 2.2 Hz, 1H), 6.63 (d, J=1.8 Hz, 1H), NH not observed; $^{19}$F NMR (376 MHz, CDCl$_3$) δ –90.8 (m, 1F), –96.0 (d, J=9.2 Hz, 1F), –104.3 (d, J=12.6 Hz, 1F).

Step 2. Preparation of 3-bromo-2,4,6-trifluoro-N-(isoxazol-3-yl)-N-((2-(trimethylsilyl)ethoxy)methyl)benzenesulfonamide

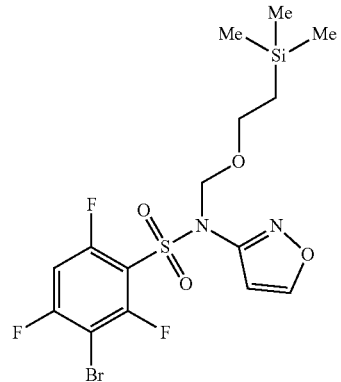 [SMILES: C[Si](C)(C)CCOCN(c1ccon1)S(=O)(=O)c1c(F)cc(F)c(Br)c1F]

To a mixture of 3-bromo-2,4,6-trifluoro-N-(isoxazol-3-yl)benzenesulfonamide (6.71 g, 18.8 mmol) and potassium carbonate (5.18 g, 37.6 mmol) in anhydrous N,N-dimethylformamide (100 mL) was added 2-(trimethylsilyl)ethoxymethyl chloride (3.76 g, 22.5 mmol) at 0° C. The reaction mixture was allowed to warm to ambient temperature and stirred for 2 h. The reaction mixture was then quenched by addition of water (300 mL), and extracted with ethyl acetate (3×150 mL). The combined organic layers were washed with brine (3×100 mL), dried over anhydrous sodium sulfate, and filtered. Concentration of the filtrate under reduced pressure and purification of the residue by column chromatography, eluting with a gradient of 0 to 20% of ethyl acetate in heptane, provided the title compound as a yellow solid (8.24 g, 90% yield): $^1$H NMR (400 MHz, CDCl$_3$) δ 8.31 (d, J=1.8 Hz, 1H), 6.89 (ddd, J=10.1, 7.8, 2.2 Hz, 1H), 6.65 (d, J=1.8 Hz, 1H), 5.42 (s, 2H), 3.77-3.66 (m, 2H), 0.96-0.84 (m, 2H), 0.00 (s, 9H).

Step 3. Preparation of 4-((2-((7-azabicyclo[2.2.1] heptan-7-yl)methyl)-6-fluorobenzyl)amino)-3-bromo-2,6-difluoro-N-(isoxazol-3-yl)-N-((2-(trimethylsilyl)ethoxy)methyl)benzenesulfonamide

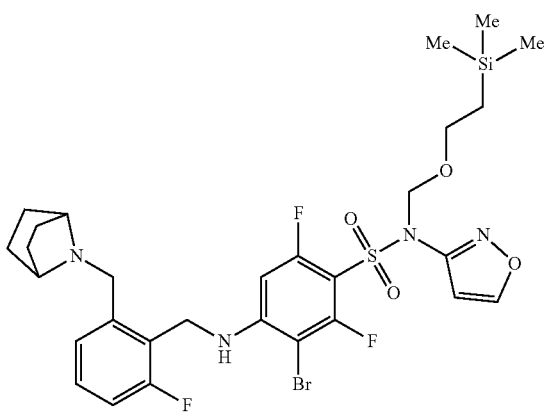 [SMILES: C[Si](C)(C)CCOCN(c1ccon1)S(=O)(=O)c1c(F)cc(NCc2c(F)cccc2CN2C3CCC2CC3)c(Br)c1F]

To a mixture of 3-bromo-2,4,6-trifluoro-N-(isoxazol-3-yl)-N-((2-(trimethylsilyl)ethoxy)methyl)benzene sulfonamide (8.24 g, 16.9 mmol) and (2-((7-azabicyclo[2.2.1]heptan-7-yl)methyl)-6-fluorophenyl)methanamine (4.15 g, 17.8 mmol) in anhydrous dimethyl sulfoxide (150 mL) was added N,N-diisopropylethylamine (6.56 g/8.8 mL, 50.7 mmol) and the reaction mixture was stirred at ambient temperature for 12 h. The reaction mixture was then added slowly to a rapidly stirring aqueous ammonium chloride solution (1500 mL) and the obtained precipitate was filtered off. The precipitate was then dissolved in ethyl acetate (500 mL). The organic phase was washed with brine (2×100 mL), dried over anhydrous sodium sulfate, and filtered. Concentration of the filtrate in vacuo and purification of the residue by column chromatography, eluting with a gradient of 0 to 20% of ethyl acetate (containing 10% of 2-propanol and 10% of trimethylamine) in heptane, provided the title compound as a colourless solid (6.23 g, 53% yield): MS (ES+) m/z 701.0 (M+1), 703.0 (M+1).

Step 4. Preparation of 4-((2-((7-azabicyclo[2.2.1] heptan-7-yl)methyl)-6-fluorobenzyl)amino)-2,6-difluoro-N-(isoxazol-3-yl)-3-methyl-N-((2-(trimethylsilyl)ethoxy)methyl)benzenesulfonamide

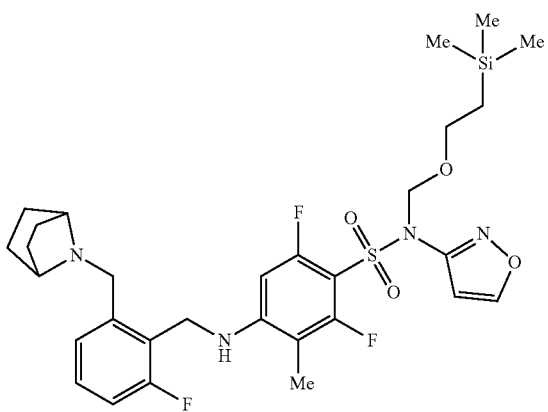

To a suspension of 4-((2-((7-azabicyclo[2.2.1]heptan-7-yl)methyl)-6-fluorobenzyl)amino)-3-bromo-2,6-difluoro-N-(isoxazol-3-yl)-N-((2-(trimethylsilyl)ethoxy)-methyl)benzenesulfonamide (5.33 g, 7.60 mmol) and potassium phosphate tribasic (9.7 g, 45.6 mmol) in anhydrous 1,4-dioxane (190 mL) was added methylboronic acid (3.64 g, 60.8 mmol) and the mixture was degassed by sparging with argon for 15 minutes. To it was then added tetrakis(triphenylphosphine)palladium(0) (0.88 g, 0.76 mmol) and the reaction mixture was heated to 90° C. for 4 h. After cooling to ambient temperature, the reaction mixture was filtered through a plug of celite. The filter cake was washed with 1,4-dioxane (2×50 mL) and the combined filtrate was concentrated in vacuo. Purification of the residue by column chromatography, eluting with a gradient of 0 to 15% of ethyl acetate (containing 10% of 2-propanol and 10% of trimethylamine) in heptane, provided the title compound as a colourless solid (4.01 g, 83% yield): $^1$H NMR (300 MHz, DMSO-$d_6$) δ 8.82 (d, J=1.8 Hz, 1H), 7.35-7.28 (m, 1H), 7.23-7.20 (m, 1H), 7.14-7.07 (m, 1H), 6.64-6.54 (m, 3H), 5.28 (s, 2H), 4.54 (dd, J=4.6, 0.3 Hz, 2H), 3.57 (dd, J=17.7, 9.7 Hz, 4H), 3.11 (dd, J=0.9, 0.5 Hz, 2H), 1.88 (d, J=2.0 Hz, 3H), 1.68-1.64 (m, 4H), 1.24-1.22 (m, 4H), 0.81 (t, J=8.0 Hz, 2H), −0.06 (s, 9H); MS (ES+) m/z 637.2 (M+1).

Step 5. Preparation of 4-((2-((7-azabicyclo[2.2.1]heptan-7-yl)methyl)-6-fluorobenzyl)amino)-2,6-difluoro-N-(isoxazol-3-yl)-3-methylbenzenesulfonamide

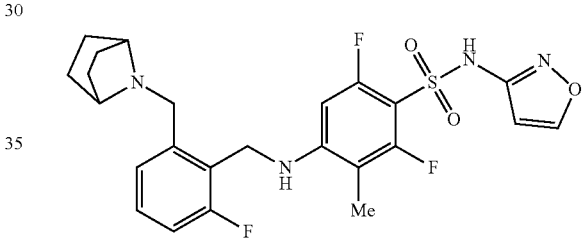

To a mixture of 4-((2-((7-azabicyclo[2.2.1]heptan-7-yl)methyl)-6-fluorobenzyl)amino)-2,6-difluoro-N-(isoxazol-3-yl)-3-methyl-N-((2-(trimethylsilyl)ethoxy)methyl)benzenesulfonamide (6.33 g, 9.94 mmol) in 1,2-dichloroethane (300 mL) was added trifluoroacetic acid (35 mL, 400 mmol) and the reaction mixture was stirred at ambient temperature for 4 h. Concentration in vacuo and purification of the residue by column chromatography, eluting with a gradient of 0-50% of ethyl acetate in heptane, followed by a gradient of 0-15% of methanol in dichloromethane, provided the title compound as a colorless solid as its trifluoroacetic acid salt. The material was dissolved in dichloromethane (500 mL) and washed with saturated aqueous sodium bicarbonate solution (2×200 mL). The combined aqueous layers were extracted with dichloromethane (3×200 mL). The combined organic layers were partially concentrated, then diluted with an equal volume of acetone, and further concentrated. The procedure of partially concentrating and diluting with acetone was repeated four times before the organic phase was concentrated to dryness. The residual solid was triturated with acetone to provide the title compound as a colourless solid (3.10 g, 62% yield): $^1$H NMR (300 MHz, DMSO-$d_6$) δ 11.43-11.31 (m, 1H), 8.62 (d, J=1.5 Hz, 1H), 7.34 (dt, J=7.8, 5.8 Hz, 1H), 7.26-7.23 (m, 1H), 7.18-7.11 (m, 1H), 6.51 (d, J=14.0 Hz, 1H), 6.41-6.37 (m, 1H), 6.28 (d, J=1.8 Hz, 1H), 4.50-4.49 (m, 2H), 3.64 (s, 2H), 3.29-3.26 (m, 2H), 1.89 (d, J=1.9 Hz, 3H), 1.74-1.68 (m, 4H), 1.31-

1.26 (m, 4H); $^{19}$F NMR (565 MHz, DMSO) δ−111.0, −112.2, −116.9; MS (ES+) m/z 507.1 (M+1).

Example 5

Synthesis of 4-((2-((7-azabicyclo[2.2.1]heptan-7-yl)methyl)-6-fluorobenzyl)amino)-2-fluoro-N-(isoxazol-3-yl)-3-methylbenzenesulfonamide 2,2,2-trifluoroacetate

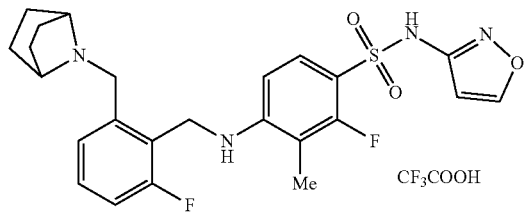 [SMILES: Cc1c(NCc2c(F)cccc2CN2C3CCC2CC3)ccc(S(=O)(=O)Nc2ccon2)c1F ; "CF3COOH"]

Step 1. Preparation of tert-butyl ((3-bromo-2,4-difluorophenyl)sulfonyl)(isoxazol-3-yl)carbamate

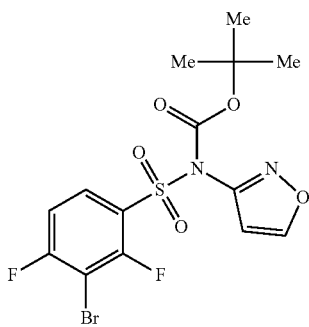 [SMILES: CC(C)(C)OC(=O)N(c1ccon1)S(=O)(=O)c1ccc(F)c(Br)c1F]

To a solution of tert-butyl isoxazol-3-ylcarbamate (3.81 g, 20.7 mmol) in anhydrous tetrahydrofuran (160 mL) was added a 1 M solution of lithium bis(trimethylsilyl)amide in tetrahydrofuran (26 mL, 26.0 mmol) at −78° C. The reaction mixture was stirred for 10 minutes at −78° C., and then allowed to warm to ambient temperature and stirred for 1 h. After cooling the reaction mixture to −78° C., a cold (−78° C.) solution of 3-bromo-2,4-difluorobenzenesulfonyl chloride (6.00 g, 20.7 mmol) in anhydrous tetrahydrofuran (100 mL) was added to it by cannula. The reaction mixture was allowed to warm to ambient temperature and stirred for 16 h. The reaction mixture was diluted with ethyl acetate (300 mL) and quenched by addition of saturated aqueous ammonium chloride solution (100 mL). The aqueous layer was separated and extracted with ethyl acetate (2×100 mL). The combined organic layers were washed with brine (100 mL), dried over anhydrous magnesium sulfate, and filtered. Concentration of the filtrate in vacuo and purification of the residue by trituration in diethyl ether (20 mL), provided the title compound as a pale yellow solid (3.50 g, 39% yield): $^1$H NMR (300 MHz, DMSO-d$_6$) δ 9.14 (d, J=1.8 Hz, 1H), 8.16 (ddd, J=9.1, 8.1, 5.8 Hz, 1H), 7.63 (ddd, J=9.2, 7.8, 1.5 Hz, 1H), 6.97 (t, J=1.6 Hz, 1H), 1.30 (s, 9H); $^{19}$F NMR (282 MHz, DMSO-d$_6$) δ−93.4, −98.0; MS (ES+) m/z 438.9 (M+1), 441.0 (M+1).

Step 2. Preparation of tert-butyl ((4-((2-((7-azabicyclo[2.2.1]heptan-7-yl)methyl)-6-fluorobenzyl)amino)-3-bromo-2-fluorophenyl)sulfonyl)(isoxazol-3-yl)carbamate

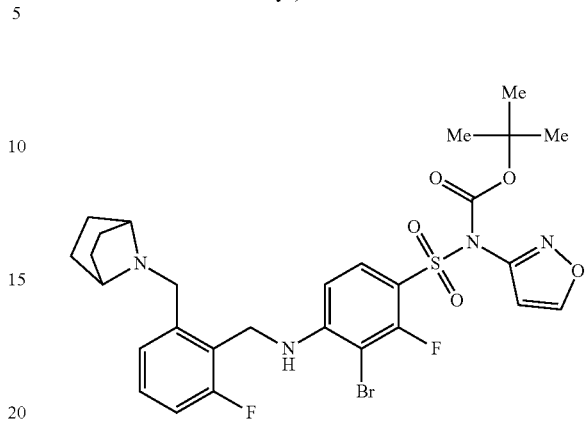

To a mixture of tert-butyl ((3-bromo-2,4-difluorophenyl)sulfonyl)(isoxazol-3-yl)carbamate (0.439 g, 1.00 mmol) and (2-((7-azabicyclo[2.2.1]heptan-7-yl)methyl)-6-fluorophenyl)methanamine (0.258 g, 1.10 mmol) in anhydrous dimethyl sulfoxide (10 mL) was added N,N-diisopropylethylamine (0.522 mL, 3.00 mmol) dropwise and the reaction mixture was stirred at ambient temperature for 14 h. The reaction mixture was diluted with ethyl acetate (150 mL) and aqueous ammonium chloride solution (50 mL) and the layers were separated. The aqueous phase was extracted with ethyl acetate (3×50 mL). The combined organic phases were washed with brine (3×30 mL), dried over anhydrous sodium sulfate, filtered and concentrated to yield the title compound as a yellow solid (0.269 g, 41% yield) which was used without further purification: MS (ES+) m/z 653.2 (M+1), 655.2 (M+1)).

Step 3. Preparation of 4-((2-((7-azabicyclo[2.2.1]heptan-7-yl)methyl)-6-fluorobenzyl)amino)-2-fluoro-N-(isoxazol-3-yl)-3-methylbenzenesulfonamide 2,2,2-trifluoroacetate

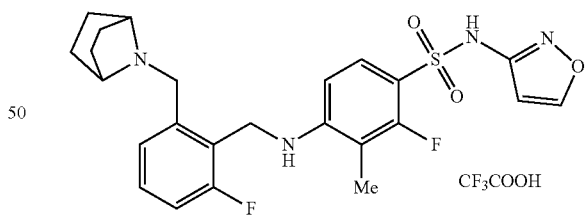

To a suspension of tert-butyl ((4-((2-((7-azabicyclo[2.2.1]heptan-7-yl)methyl)-6-fluorobenzyl)amino)-3-bromo-2-fluorophenyl)sulfonyl)(isoxazol-3-yl)carbamate (0.269 g, 0.412 mmol) and potassium phosphate tribasic (0.350 g, 1.65 mmol) in anhydrous 1,4-dioxane (10 mL) was added methylboronic acid (0.148 g, 2.47 mmol) and the mixture was degassed by sparging with argon for 15 minutes. To it was then added tetrakis(triphenylphosphine)palladium(0) (0.047 g, 0.041 mmol) and the reaction mixture was heated to 90° C. for 4 h. After cooling to ambient temperature, the reaction mixture was filtered through a plug of celite. The filter cake was washed with 1,4-dioxane (2×50 mL) and the combined filtrate was concentrated in vacuo. The resulting residue was dissolved in dichloromethane (10 mL) and trifluoroacetic acid (5 mL) under an atmosphere of nitrogen. The reaction mixture was stirred at ambient temperature for 2 h. The reaction mixture was concentrated in vacuo and the residue was purified by preparative reverse phase HPLC using acetonitrile in water containing 0.1% trifluoroacetic acid as eluent, to yield the title compound as a colorless solid (0.057 g, 22% yield): $^1$H NMR (300 MHz, DMSO-$d_6$) δ 11.52 (s, 1H), 9.55-9.52 (m, 1H), 8.67 (d, J=1.8 Hz, 1H), 7.60-7.32 (m, 4H), 6.60 (d, J=9.0 Hz, 1H), 6.36-6.32 (m, 2H), 4.48 (td, J=1.2, 0.5 Hz, 2H), 4.35-4.33 (m, 2H), 4.14 (s, 2H), 2.20-2.16 (m, 2H), 1.97-1.90 (m, 5H), 1.76-1.67 (m, 4H); MS (ES+) m/z 489.1 (M+1).

Example 6

Synthesis of 4-((2-((7-azabicyclo[2.2.1]heptan-7-yl)methyl)-6-fluorobenzyl)amino)-3-chloro-2-fluoro-N-(thiazol-4-yl)benzenesulfonamide 2,2,2-trifluoroacetate

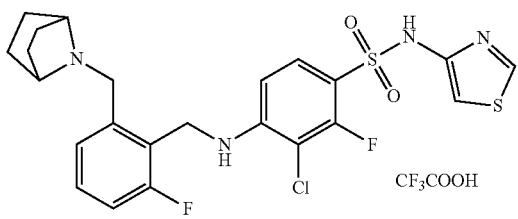 [SMILES: O=S(=O)(Nc1cscn1)c1ccc(NCc2c(F)cccc2CN2C3CCC2CC3)c(Cl)c1F ; "CF3COOH"]

Step 1. Preparation of tert-butyl ((3-chloro-2,4-difluorophenyl)sulfonyl)(thiazol-4-yl)carbamate

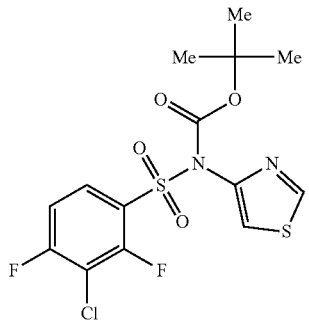 [SMILES: CC(C)(C)OC(=O)N(c1cscn1)S(=O)(=O)c1ccc(F)c(Cl)c1F]

To a solution of tert-butyl N-thiazol-4-ylcarbamate (110 g, 549 mmol) in tetrahydrofuran (1000 mL) was added lithium bis(trimethylsilyl)amide (1 M in tetrahydrofuran, 659 mL, 659 mmol) at −78° C. The mixture was warmed to 5° C. before a cooled (−78° C.) solution of 3-chloro-2,4-difluorobenzenesulfonyl chloride (163 g, 659 mmol) in tetrahydrofuran (300 mL) was added to it dropwise. The reaction mixture was stirred at ambient temperature for 12 h. The reaction mixture was diluted with saturated aqueous ammonium chloride (200 mL) and extracted with ethyl acetate (3×1000 mL). The combined organic layers were washed with brine (3×1000 mL), dried over anhydrous sodium sulfate, filtered and concentrated in vacuo. The residue was triturated with methanol (300 mL) to give the title compound as a colorless solid (75 g, 33% yield): $^1$H NMR (400 MHz, CDCl$_3$) δ 9.14 (s, 1H), 8.26-8.09 (m, 1H), 8.03 (s, 1H), 7.66 (t, J=8.6 Hz, 1H), 1.27 (s, 9H); MS (ES+) m/z 432.8 (M+23), 434.8 (M+23).

Step 2. Preparation of tert-butyl ((4-((2-((7-azabicyclo[2.2.1]heptan-7-yl)methyl)-6-fluorobenzyl)amino)-3-chloro-2-fluorophenyl)sulfonyl)(thiazol-4-yl)carbamate

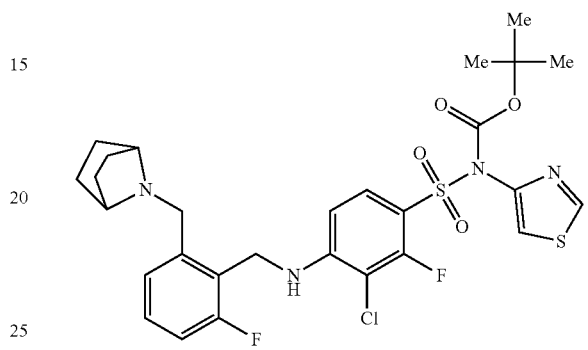

To a suspension of tert-butyl ((3-chloro-2,4-difluorophenyl)sulfonyl)(thiazol-4-yl)carbamate (0.410 g, 1.00 mmol) and (2-((7-azabicyclo[2.2.1]heptan-7-yl)methyl)-6-fluorophenyl)methanamine (0.258 g, 1.10 mmol) in anhydrous dimethyl sulfoxide (10 mL) was added N,N-diisopropylethylamine (0.522 mL, 3.00 mmol) and the reaction mixture was stirred at ambient temperature for 14 h. The reaction mixture was diluted with ethyl acetate (150 mL) and aqueous ammonium chloride solution (50 mL) and the layers were separated. The aqueous phase was extracted with ethyl acetate (3×50 mL). The combined organic phases were washed with brine (3×30 mL), dried over anhydrous sodium sulfate, filtered and concentrated in vacuo to yield the title compound as a yellow solid (0.338 g, 54% yield) which was used without further purification: MS (ES+) m/z 625.2 (M+1), 627.2 (M+1)).

Step 3. Preparation of 4-((2-((7-azabicyclo[2.2.1]heptan-7-yl)methyl)-6-fluorobenzyl)amino)-3-chloro-2-fluoro-N-(thiazol-4-yl)benzenesulfonamide 2,2,2-trifluoroacetate

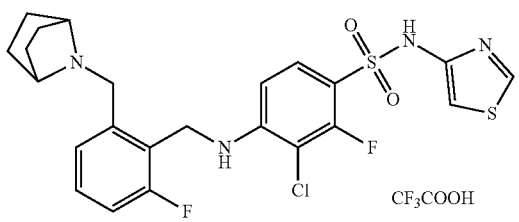 [SMILES: O=S(=O)(Nc1cscn1)c1ccc(NCc2c(F)cccc2CN2C3CCC2CC3)c(Cl)c1F ; "CF3COOH"]

To a solution of tert-butyl ((4-((2-((7-azabicyclo[2.2.1] heptan-7-yl)methyl)-6-fluorobenzyl)amino)-3-chloro-2-fluorophenyl)sulfonyl)(thiazol-4-yl)carbamate (0.200 g, 0.320 mmol) in dichloromethane (5 mL) was added trifluoroacetic acid (10 mL) and the the reaction mixture was stirred at ambient temperature for 2 h. The reaction mixture was then concentrated in vacuo and the residue was purified by preparative reverse phase HPLC using acetonitrile in water containing 0.1% trifluoroacetic acid as eluent, to yield the title compound as a colorless solid (0.102 g, 50% yield): $^1$H NMR (300 MHz, DMSO-$d_6$) δ 11.21 (s, 1H), 9.61-9.57 (m, 1H), 8.88 (d, J=2.2 Hz, 1H), 7.60 (t, J=8.5 Hz, 1H), 7.53-7.31 (m, 3H), 6.98 (d, J=2.2 Hz, 1H), 6.90-6.87 (m, 1H), 6.72 (d, J=9.1 Hz, 1H), 4.56-4.55 (m, 2H), 4.37-4.36 (m, 2H), 4.16 (d, J=0.3 Hz, 2H), 2.21-2.18 (m, 2H), 1.94-1.91 (m, 2H), 1.77-1.66 (m, 4H); MS (ES+) m/z 525.1 (M+1), 527.1 (M+1).

Example 7

Synthesis of 4-((2-((7-azabicyclo[2.2.1]heptan-7-yl)methyl)-6-fluorobenzyl)amino)-2-fluoro-3-methyl-N-(thiazol-4-yl)benzenesulfonamide 2,2,2-trifluoroacetate

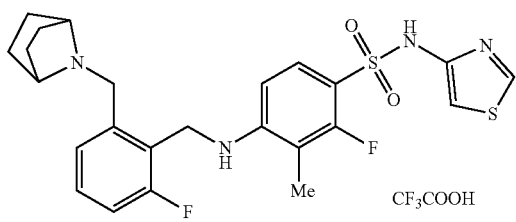 [SMILES: Cc1c(NCc2c(F)cccc2CN2C3CCC2CC3)ccc(S(=O)(=O)Nc2cscn2)c1F ; "CF3COOH"]

To a microwave vial was added tert-butyl ((4-((2-((7-azabicyclo[2.2.1]heptan-7-yl)methyl)-6-fluorobenzyl)amino)-3-chloro-2-fluorophenyl)sulfonyl)(thiazol-4-yl)carbamate (0.138 g, 0.221 mmol), potassium phosphate tribasic (0.141 g, 0.663 mmol), methylboronic acid (0.106 g, 1.77 mmol), tricyclohexylphosphine tetrafluoroborate (0.275 g, 0.75 mmol) and anhydrous 1,4-dioxane (4 mL). The resulting suspension was degassed by sparging with argon for 15 minutes before palladium(II) acetate (0.007 g, 0.033 mmol) was added to it. The vial was sealed and then heated in a microwave reactor to 120° C. for 3 h. After cooling to ambient temperature, the reaction mixture was filtered through a plug of celite. The filter cake was washed with 1,4-dioxane (2×50 mL) and the combined filtrate was concentrated in vacuo. The resulting residue was dissolved in dichloromethane (5 mL) and trifluoroacetic acid (5 mL) was added to it. The reaction mixture was stirred at ambient temperature for 2 h. The reaction mixture was concentrated in vacuo and the residue was purified by preparative reverse phase HPLC using acetonitrile in water containing 0.1% trifluoroacetic acid as eluent, to yield the title compound as a colorless solid (0.043 g, 31% yield): $^1$H NMR (300 MHz, DMSO-$d_6$) δ 11.05 (s, 1H), 9.50 (ddd, J=2.6, 1.4, 0.7 Hz, 1H), 8.86 (d, J=2.2 Hz, 1H), 7.55-7.32 (m, 4H), 6.88 (d, J=2.2 Hz, 1H), 6.56 (d, J=8.9 Hz, 1H), 6.27-6.24 (m, 1H), 4.46 (dd, J=2.5, 0.7 Hz, 2H), 4.33 (d, J=4.9 Hz, 2H), 4.13 (d, J=0.4 Hz, 2H), 2.19-2.15 (m, 2H), 1.96 (d, J=1.8 Hz, 3H), 1.96-1.89 (m, 2H), 1.75-1.66 (m, 4H); MS (ES+) m/z 505.1 (M+1).

Example 8

Synthesis of 2,6-difluoro-4-((6-fluoro-3-isopropoxy-2-((isopropyl(methyl)amino)methyl)benzyl)amino)-N-(thiazol-4-yl)benzenesulfonamide

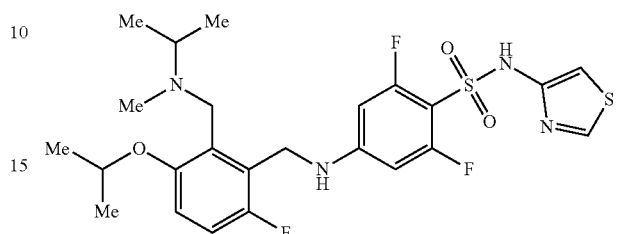

Step 1. Preparation of 2-bromo-3-fluoro-6-hydroxybenzaldehyde

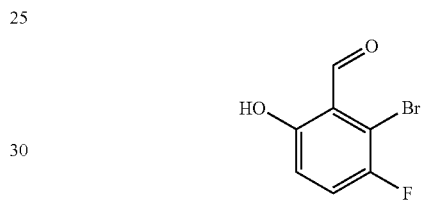

To a solution of 2-bromo-3-fluoro-6-methoxybenzaldehyde (5.0 g, 21.5 mmol) in anhydrous dichloromethane (100 mL) was slowly added boron tribromide (2.5 mL, 25.8 mmol) at −78° C. The reaction was then allowed to warm to ambient temperature and stirred for 18 h. The solution was cooled to 0° C. and quenched by addition of saturated aqueous ammonium chloride (100 mL). The aqueous layer was extracted with dichloromethane (2×100 mL) and the combined organic layers were washed with brine (2×50 mL), dried over anhydrous magnesium sulfate, and filtered. Concentration of the filtrate in vacuo and purification of the residue by column chromatography, eluting with 0 to 100% of ethyl acetate in heptane, provided the title compound as a colorless oil (2.35 g, 50% yield): $^1$H NMR (300 MHz, DMSO-$d_6$) δ 11.37-11.31 (m, 1H), 10.23 (d, J=16.2 Hz, 1H), 7.58 (dd, J=9.1, 8.5 Hz, 1H), 7.05 (dd, J=9.2, 4.3 Hz, 1H).

Step 2. Preparation of 2-bromo-3-fluoro-6-isopropoxybenzaldehyde

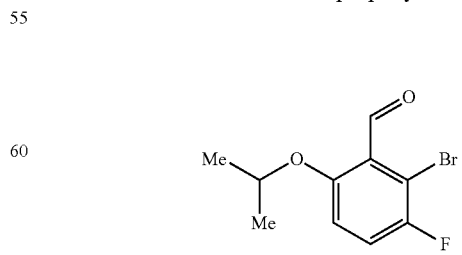

To a mixture of 2-bromo-3-fluoro-6-hydroxybenzaldehyde (1.41 g, 6.44 mmol) and potassium carbonate (2.67 g, 19.3 mmol) in anhydrous N,N-dimethylformamide (35 mL) was added 2-iodopropane (0.77 mL, 7.73 mmol) and the reaction was heated to 60° C. for 18 h. The reaction was then allowed to cool to ambient temperature, and diluted with ethyl acetate (50 mL) and water (50 mL). The aqueous layer was extracted with ethyl acetate (3×50 mL) and the combined organic layers were washed with brine (2×50 mL), dried over anhydrous magnesium sulfate, and filtered. Concentration of the filtrate in vacuo and purification of the residue by column chromatography, eluting with a gradient of 5 to 60% of ethyl acetate in heptane, afforded the title compound as a yellow oil (1.68 g, quantitative yield): $^1$H NMR (300 MHz, CDCl$_3$) δ 10.39 (d, J=1.2 Hz, 1H), 7.29-7.24 (m, 1H), 6.96 (dd, J=9.2, 3.9 Hz, 1H), 4.61 (sept, J=6.1 Hz, 1H), 1.39 (d, J=6.0 Hz, 6H).

Step 3. Preparation of N-(2-bromo-3-fluoro-6-isopropoxybenzyl)-N-methylpropan-2-amine

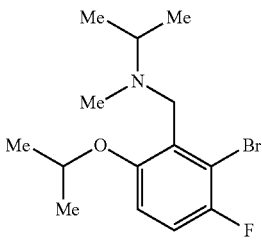 [SMILES: CC(C)Oc1ccc(F)c(Br)c1CN(C)C(C)C]

To a mixture of 2-bromo-3-fluoro-6-isopropoxybenzaldehyde (1.67 g, 6.44 mmol) and N-methylpropan-2-amine (1.3 mL, 12.88 mmol) in anhydrous dichloromethane (32 mL) was added sodium triacetoxyborohydride (6.25 g, 29.6 mmol). The reaction mixture was stirred at ambient temperature for 18 h and then quenched by addition of saturated aqueous ammonium chloride solution (50 mL). The aqueous layer was extracted with dichloromethane (3×50 mL) and the combined organic layers were washed with brine (50 mL), dried over anhydrous magnesium sulfate, and filtered. Concentration of the filtrate in vacuo and purification of the residue by column chromatography, eluting with a gradient of 0-20% of methanol in dichloromethane, afforded the title compound as a colorless oil (2.05 g, quantitative yield): MS (ES+) m/z 318.0 (M+1), 320.0 (M+1).

Step 4. Preparation of (E)-6-fluoro-3-isopropoxy-2-((isopropyl(methyl)amino)methyl)benzaldehyde Oxime

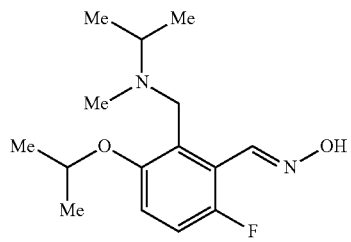 [SMILES: CC(C)Oc1ccc(F)c(/C=N/O)c1CN(C)C(C)C]

To a flask charged with N-(2-bromo-3-fluoro-6-isopropoxybenzyl)-N-methylpropan-2-amine (2.05 g, 6.44 mmol) was added anhydrous tetrahydrofuran (13 mL) and the mixture was cooled to an internal temperature of 0° C. using an ice-water bath. To it was then added a 1.3 M solution of isopropylmagnesium chloride lithium chloride complex in tetrahydrofuran (9.7 mL, 19.32 mmol). The reaction mixture was stirred at 0° C. for 30 minutes and a second portion of 1.3 M solution of isopropylmagnesium chloride lithium chloride complex in tetrahydrofuran (9.7 mL, 19.32 mmol) was added to it. The reaction mixture was stirred at 0° C. for 30 minutes, after which anhydrous N,N-dimethylformamide (5 mL, 64.4 mmol) was added to it. The reaction mixture was allowed to warm to ambient temperature and stirred for 45 minutes. To it was then added a 50% solution of hydroxylamine hydrochloride in water (4.3 mL, 64.4 mmol) and the reaction mixture was stirred vigorously at ambient temperature for 18 h. The reaction mixture was diluted with ethyl acetate (100 mL) and water (100 mL). The aqueous phase was extracted with ethyl acetate (3×50 mL), and the combined organic layers were washed with brine (100 mL), dried over anhydrous magnesium sulfate, and filtered. Concentration of the filtrate in vacuo and purification of the residue by column chromatography, eluting with a gradient of 10 to 70% of ethyl acetate (containing 10% of 2-propanol and 10% of triethylamine) in heptane, afforded the title compound as a colorless solid (0.778 g, 43% yield): MS (ES+) m/z 283.2 (M+1).

Step 5. Preparation of N-(2-(aminomethyl)-3-fluoro-6-isopropoxybenzyl)-N-methylpropan-2-amine

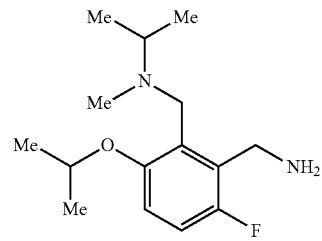 [SMILES: CC(C)Oc1ccc(F)c(CN)c1CN(C)C(C)C]

To (E)-6-fluoro-3-isopropoxy-2-((isopropyl(methyl)amino)methyl)benzaldehyde oxime (0.778 g, 2.75 mmol) was added glacial acetic acid (14 mL) and the mixture was stirred for 15 minutes before being cooled in a water/ice bath. To it was then added zinc powder (1.07 g, 16.5 mmol) and the reaction mixture was heated to 60° C. for 1.5 h. After cooling to ambient temperature, the reaction mixture was filtered, and the filter cake was washed with dichloromethane (3×50 mL). The combined organic filtrate was washed with saturated aqueous sodium bicarbonate solution (3×100 mL), brine (100 mL), dried over anhydrous magnesium sulfate, and filtered. Concentration of the filtrate in vacuo afforded the title compound as an orange wax (0.498 g, 67% yield) that was used without further purification: $^1$H NMR (300 MHz, CDCl$_3$) δ 7.05-6.97 (m, 1H), 6.84-6.79 (m, 1H), 4.56-4.49 (m, 1H), 4.14-4.09 (m, 2H), 3.91-3.84 (m, 2H), 3.53-3.48 (m, 2H), 3.14-3.05 (m, 1H), 2.28-2.24 (m, 3H), 1.38-1.30 (m, 6H), 1.17-1.08 (m, 6H).

Step 6. Preparation of 2,6-difluoro-4-((6-fluoro-3-isopropoxy-2-((isopropyl(methyl)amino)methyl)benzyl)amino)-N-(thiazol-4-yl)benzenesulfonamide

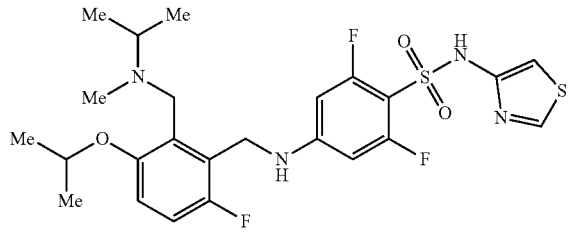 [SMILES: CC(C)Oc1ccc(F)c(CNc2cc(F)c(S(=O)(=O)Nc3cscn3)c(F)c2)c1CN(C)C(C)C]

To a mixture of tert-butyl thiazol-4-yl((2,4,6-trifluorophenyl)sulfonyl)carbamate (0.729 g, 1.85 mmol) and N-(2-(aminomethyl)-3-fluoro-6-isopropoxybenzyl)-N-methylpropan-2-amine (0.498 g, 1.85 mmol) in anhydrous dimethyl sulfoxide (9 mL) was added N,N-diisopropylethylamine (1.0 mL, 5.55 mmol). The reaction mixture was stirred at ambient temperature for 18 h. The mixture was then diluted with ethyl acetate (50 mL) and saturated aqueous ammonium chloride solution (50 mL). The aqueous layer was extracted with ethyl acetate (3×50 mL). The combined organic layers were washed with brine (100 mL), dried over anhydrous magnesium sulfate, and filtered. The filtrate was concentrated in vacuo and purified by column chromatography, eluting with a gradient of 5 to 60% of ethyl acetate (containing 10% of 2-propanol and 10% of triethylamine) in heptane to afford a colorless oil. The oil was then dissolved in dichloromethane (10 mL) and trifluoroacetic acid (2 mL) was added to it. The reaction mixture was stirred at ambient temperature for 18 h and then concentrated in vacuo. Purification of the residue by column chromatography, eluting with a gradient of 10 to 80% of ethyl acetate (containing 20% of ethanol and 2% of saturated ammonium hydroxide) in heptane, afforded the title compound as a colorless solid (0.304 g, 31% yield): $^1$H NMR (300 MHz, DMSO-$d_6$) δ 11.22-11.08 (m, 1H), 8.89 (d, J=2.2 Hz, 1H), 7.45-7.42 (m, 1H), 7.17-7.09 (m, 1H), 7.07-7.00 (m, 1H), 6.89 (d, J=2.2 Hz, 1H), 6.38-6.33 (m, 2H), 4.64-4.55 (m, 1H), 4.35-4.33 (m, 2H), 3.66-3.58 (m, 2H), 2.88-2.62 (m, 1H), 2.09-2.01 (m, 3H), 1.26 (d, J=6.0 Hz, 6H), 1.01-0.97 (m, 6H); MS (ES+) m/z 543.1 (M+1).

Example 9

Synthesis of 4-((2-((7-azabicyclo[2.2.1]heptan-7-yl)methyl)-6-fluorobenzyl)amino)-2,6-difluoro-N-(thiazol-4-yl)benzenesulfonamide 2,2,2-trifluoroacetate

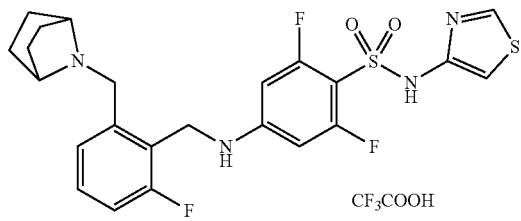 [SMILES: O=S(=O)(Nc1cscn1)c1c(F)cc(NCc2c(F)cccc2CN2C3CCC2CC3)cc1F ; "CF3COOH"]

Step 1. Preparation of 4-((2-((7-azabicyclo[2.2.1]heptan-7-yl)methyl)-6-fluorobenzyl)amino)-2,6-difluoro-N-(4-methoxybenzyl)-N-(thiazol-4-yl)benzenesulfonamide

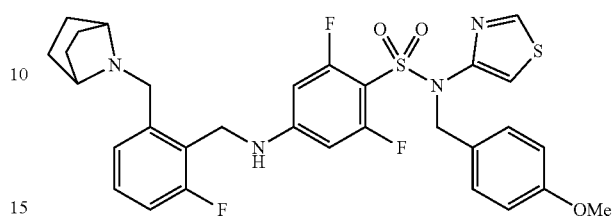

To a mixture of 2,4,6-trifluoro-N-(4-methoxybenzyl)-N-(thiazol-4-yl)benzenesulfonamide (0.44 g, 1.07 mmol, prepared according to PCT Published Patent Application No. WO 2018/106284) and (2-((7-azabicyclo[2.2.1]heptan-7-yl)methyl)-6-fluorophenyl)methanamine (0.25 g, 1.07 mmol) in anhydrous dimethyl sulfoxide (10 mL) was added potassium carbonate (0.30 g, 2.14 mmol) and the reaction mixture was stirred at ambient temperature for 16 h. The reaction mixture was diluted with saturated aqueous ammonium chloride solution (20 mL), and extracted with ethyl acetate (3×30 mL). The combined organic layers were washed with water (40 mL), brine (40 mL), dried over anhydrous magnesium sulfate, filtered, and concentrated in vacuo. Purification of the residue by column chromatography, eluting with a gradient of 0 to 40% of ethyl acetate (containing 10% of isopropanol and 10% of triethylamine) in hexanes, provided the title compound as a colorless solid (0.38 g, 56% yield): MS (ES+) m/z 629.3 (M+1).

Step 2. Preparation of 4-((2-((7-azabicyclo[2.2.1]heptan-7-yl)methyl)-6-fluorobenzyl)amino)-2,6-difluoro-N-(thiazol-4-yl)benzenesulfonamide 2,2,2-trifluoroacetate

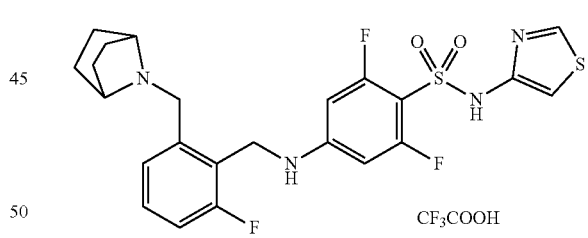

To a solution of 4-((2-((7-azabicyclo[2.2.1]heptan-7-yl)methyl)-6-fluorobenzyl)amino)-2,6-difluoro-N-(4-methoxybenzyl)-N-(thiazol-4-yl)benzenesulfonamide (0.38 g, 0.75 mmol) in anhydrous dichloromethane (3 mL) was added trifluoroacetic acid (3 mL) and the reaction mixture was heated to reflux for 16 h. After cooling to ambient temperature, the reaction mixture was concentrated in vacuo. Purification of the residue by column chromatography, eluting with a gradient of 0 to 10% of methanol in dichloromethane, afforded the title compound as colorless solid (0.29 g, 62% yield): $^1$H NMR (300 MHz, DMSO-$d_6$) δ 11.23 (s, 1H), 9.56 (s, 1H), 8.90 (d, J=2.2 Hz, 1H), 7.59-7.30 (m, 4H), 6.92 (d, J=2.1 Hz, 1H), 6.41-6.32 (m, 2H), 4.39-4.06 (m, 6H), 2.22-2.06 (m, 2H), 2.01-1.86 (m, 2H), 1.78-1.57 (m, 4H); MS (ES+) m/z 509.1 (M+1).

Example 10

Synthesis of 4-((2-((7-azabicyclo[2.2.1]heptan-7-yl)methyl)-3,6-difluorobenzyl)amino)-2,6-difluoro-N-(thiazol-4-yl)benzenesulfonamide

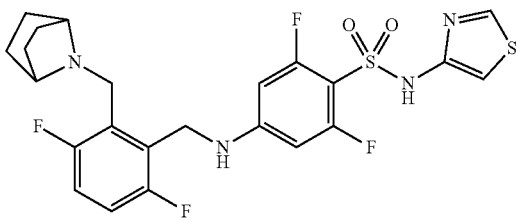 [SMILES: O=S(=O)(Nc1cscn1)c1c(F)cc(NCc2c(F)ccc(F)c2CN2C3CCC2CC3)cc1F]

Step 1. Preparation of 2-bromo-3-(bromomethyl)-1,4-difluorobenzene

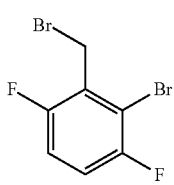

To a solution of (2-bromo-3,6-difluorophenyl)methanol (10.75 g, 48.20 mmol, prepared according to PCT Published Patent Application No. WO 2018/106284) in anhydrous dichloromethane (150 mL) at 0° C. was added carbon tetrabromide (25.58 g, 77.12 mmol) and triphenylphosphine (15.17 g, 57.84 mmol). The reaction mixture was stirred at 0° C. for 2 h and then concentrated in vacuo. Purification of the residue by column chromatography, eluting with a gradient of 0 to 10% of ethyl acetate in heptane, afforded the title compound as colorless oil (8.51 g, 62% yield): $^1$H NMR (300 MHz, CDCl$_3$): δ 7.14-7.01 (m, 2H), 4.66-4.61 (m, 2H); MS (ES+) m/z 286.0 (M+1), 288.0 (M+1).

Step 2. Preparation of 7-(2-bromo-3,6-difluorobenzyl)-7-azabicyclo[2.2.1]heptane

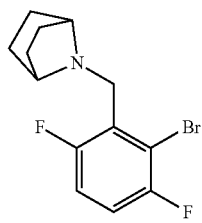 [SMILES: Fc1ccc(F)c(CN2C3CCC2CC3)c1Br]

Following the procedure as described in EXAMPLE 1, Step 1 and making non-critical variations as required to replace 2-(bromomethyl)-6-fluorobenzonitrile with 2-bromo-3-(bromomethyl)-1,4-difluorobenzene, the title compound was obtained as a colorless solid (5.15 g, 98% yield): MS (ES+) m/z 302.0 (M+1), 304.0 (M+1).

Step 3. Preparation of (E)-2-((7-azabicyclo[2.2.1]heptan-7-yl)methyl)-3,6-difluorobenzaldehyde Oxime

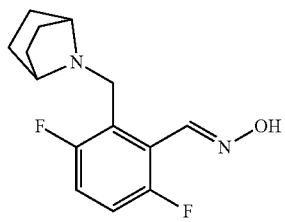 [SMILES: O/N=C/c1c(F)ccc(F)c1CN1C2CCC1CC2]

Following the procedure as described in EXAMPLE 2, Step 6, and making non-critical variations as required to replace N-(2-bromo-3-fluoro-6-methoxybenzyl)-N-methylpropan-2-amine with 7-(2-bromo-3,6-difluorobenzyl)-7-azabicyclo[2.2.1]heptane, the title compound was obtained as a colorless solid (1.02 g, 97% yield): MS (ES+) m/z 267.2 (M+1).

Step 4. Preparation of (2-((7-azabicyclo[2.2.1]heptan-7-yl)methyl)-3,6-difluorophenyl)methanamine

To a solution of (E)-2-((7-azabicyclo[2.2.1]heptan-7-yl)methyl)-3,6-difluorobenzaldehyde oxime (0.53 g, 1.98 mmol) in anhydrous tetrahydrofuran (10 mL) at 0° C. was added a 1 M solution of lithium aluminum hydride in tetrahydrofuran (4.0 mL, 4.0 mmol). The reaction mixture was stirred at 0° C. for 15 minutes, and at ambient temperature for 16 h, and then heated under reflux for 30 minutes. The reaction mixture was cooled to 0° C. and sodium sulfate decahydrate (4.0 g) was added to it in small portions. The reaction mixture was stirred at 0° C. for 30 minutes and then at ambient temperature for 1.5 h. The mixture was filtered, and the filter cake was rinsed with ethyl acetate (2×10 mL). The combined filtrate was dried over anhydrous magnesium sulfate. Filtration and concentration of the filtrate in vacuo afforded the title compound as a brown oil (0.45 g, 90% yield): MS (ES+) m/z 253.2 (M+1).

Step 5. Preparation of 4-((2-((7-azabicyclo[2.2.1]heptan-7-yl)methyl)-3,6-difluorobenzyl)amino)-2,6-difluoro-N-(4-methoxybenzyl)-N-(thiazol-4-yl)benzenesulfonamide

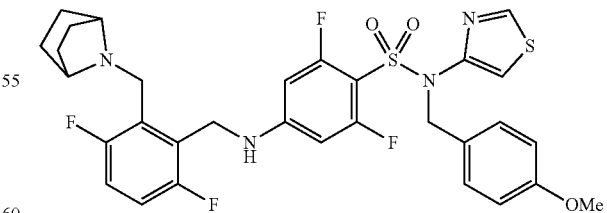

Following the procedure as described in EXAMPLE 9, Step 1 and making non-critical variations as required to replace (2-((7-azabicyclo[2.2.1]heptan-7-yl)methyl)-6-fluorophenyl)methanamine with of (2-((7-azabicyclo[2.2.1]heptan-7-yl)methyl)-3,6-difluorophenyl)methanamine, the title compound was obtained as a colorless solid (0.19 g, 16% yield): MS (ES+) m/z 647.2 (M+1).

Step 6. Preparation of 4-((2-((7-azabicyclo[2.2.1]heptan-7-yl)methyl)-3,6-difluorobenzyl)amino)-2,6-difluoro-N-(thiazol-4-yl)benzenesulfonamide

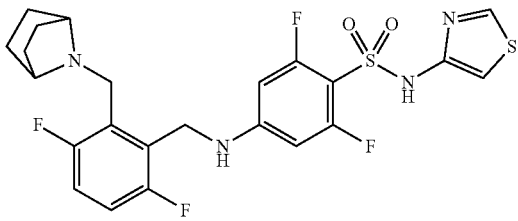 [SMILES: O=S(=O)(Nc1cscn1)c1c(F)cc(NCc2c(F)ccc(F)c2CN2C3CCC2CC3)cc1F]

Following the procedure as described in EXAMPLE 9, Step 2 and making non-critical variations as required to replace 4-((2-((7-azabicyclo[2.2.1]heptan-7-yl)methyl)-6-fluorobenzyl)amino)-2,6-difluoro-N-(4-methoxybenzyl)-N-(thiazol-4-yl)benzenesulfonamide with 4-((2-((7-azabicyclo[2.2.1]heptan-7-yl)methyl)-3,6-difluorobenzyl)amino)-2,6-difluoro-N-(4-methoxybenzyl)-N-(thiazol-4-yl)benzenesulfonamide, the title compound was obtained as a colorless solid (0.096 g, 52% yield): $^1$H NMR (300 MHz, DMSO-d$_6$) δ 11.18 (br s, 1H), 8.89 (d, J=2.2 Hz, 1H), 7.46-7.21 (m, 3H), 6.90 (d, J=2.2 Hz, 1H), 6.42-6.30 (m, 2H), 4.51-4.39 (m, 2H), 3.61 (br s, 2H), 3.13 (br s, 2H), 1.68 (br s, 4H), 1.29 (br s, 4H); MS (ES+) m/z 527.1 (M+1).

Example 11

Synthesis of 4-((2-((7-azabicyclo[2.2.1]heptan-7-yl)methyl)-6-fluoro-3-methoxybenzyl)amino)-2,6-difluoro-N-(thiazol-4-yl)benzenesulfonamide 2,2,2-trifluoroacetate

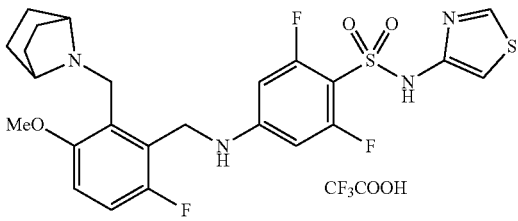 [SMILES: COc1ccc(F)c(CNc2cc(F)c(S(=O)(=O)Nc3cscn3)c(F)c2)c1CN1C2CCC1CC2 ; "CF3COOH"]

Step 1. Preparation of (2-bromo-3-fluoro-6-methoxyphenyl)methanol

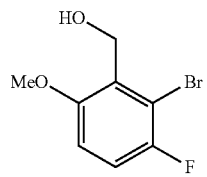 [SMILES: COc1ccc(F)c(Br)c1CO]

To a solution of 2-bromo-3-fluoro-6-methoxybenzaldehyde (4.19 g, 17.98 mmol) in anhydrous methanol (37 mL) was added sodium borohydride (1.36 g, 35.96 mmol) at 0° C. in small portions. The reaction mixture was stirred at 0° C. for 1 h and then concentrated in vacuo. The residue was diluted with saturated aqueous ammonium chloride solution (100 mL), and extracted with ethyl acetate (3×60 mL). The combined organic layers were washed with water (50 mL), brine (60 mL), dried over anhydrous magnesium sulfate, and filtered. Concentration of the filtrate in vacuo afforded the title compound as a colorless solid (4.23 g, quantitative yield): MS (ES+) m/z 258.0 (M+1), 259.8 (M+1).

Step 2. Preparation of 2-bromo-3-(bromomethyl)-1-fluoro-4-methoxybenzene

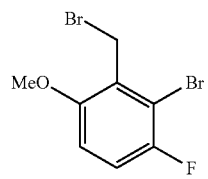 [SMILES: COc1ccc(F)c(Br)c1CBr]

Following the procedure as described in EXAMPLE 10, Step 1 and making non-critical variations as required to replace (2-bromo-3,6-difluorophenyl)methanol with (2-bromo-3-fluoro-6-methoxyphenyl)methanol, the title compound was obtained as a colorless solid (2.85 g, 53% yield): $^1$H NMR (300 MHz, CDCl$_3$) δ 7.12-7.03 (m, 1H), 6.84-6.78 (m, 1H), 4.75-4.70 (m, 2H), 3.90 (s, 3H).

Step 3. Preparation of 7-(2-bromo-3-fluoro-6-methoxybenzyl)-7-azabicyclo[2.2.1]-heptane

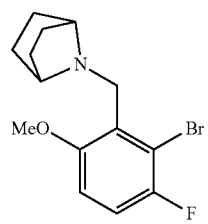 [SMILES: COc1ccc(F)c(Br)c1CN1C2CCC1CC2]

Following the procedure as described in EXAMPLE 1, Step 1 and making non-critical variations as required to replace 2-(bromomethyl)-6-fluorobenzonitrile with 2-bromo-3-(bromomethyl)-1-fluoro-4-methoxybenzene, the title compound was obtained as a colorless solid (2.09 g, 70% yield): MS (ES+) m/z 314.0 (M+1), 316.0 (M+1).

Step 4. Preparation of (E)-2-((7-azabicyclo[2.2.1]heptan-7-yl)methyl)-6-fluoro-3-methoxybenzaldehyde Oxime

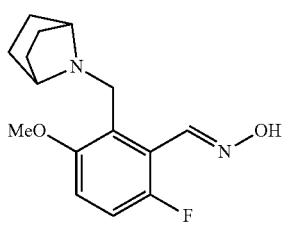 [SMILES: COc1ccc(F)c(/C=N/O)c1CN1C2CCC1CC2]

Following the procedure as described in EXAMPLE 2, Step 6 and making non-critical variations as required to replace N-(2-bromo-3-fluoro-6-methoxybenzyl)-N-methylpropan-2-amine with 7-(2-bromo-3-fluoro-6-methoxybenzyl)-7-azabicyclo[2.2.1]heptane, the title compound was obtained as a colorless solid (1.9 g, 51% yield): MS (ES+) m/z 279.2 (M+1).

Step 5. Preparation of (2-((7-azabicyclo[2.2.1]heptan-7-yl)methyl)-6-fluoro-3-methoxyphenyl)methanamine

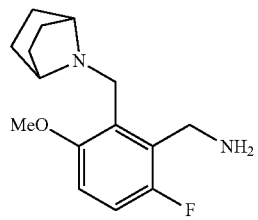 [SMILES: COc1ccc(F)c(CN)c1CN1C2CCC1CC2]

Following the procedure as described in EXAMPLE 2, Step 7 and making non-critical variations as required to replace (E)-6-fluoro-2-((isopropyl(methyl)amino)methyl)-3-methoxybenzaldehyde oxime with (E)-2-((7-azabicyclo[2.2.1]heptan-7-yl)methyl)-6-fluoro-3-methoxybenzaldehyde oxime, the title compound was obtained as a colorless solid (0.84 g, 46% yield): MS (ES+) m/z 265.2 (M+1).

Step 6. Preparation of 4-((2-((7-azabicyclo[2.2.1]heptan-7-yl)methyl)-6-fluoro-3-methoxybenzyl)amino)-2,6-difluoro-N-(4-methoxybenzyl)-N-(thiazol-4-yl)benzenesulfonamide

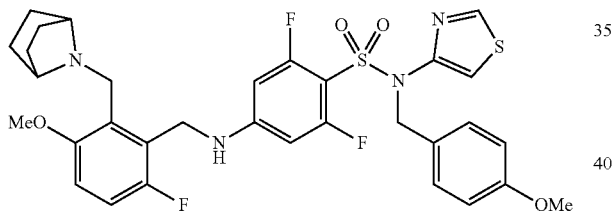

Following the procedure as described in EXAMPLE 9, Step 1 and making non-critical variations as required to replace (2-((7-azabicyclo[2.2.1]heptan-7-yl)methyl)-6-fluorophenyl)methanamine with of (2-((7-azabicyclo[2.2.1]heptan-7-yl)methyl)-6-fluoro-3-methoxyphenyl)methanamine, the title compound was obtained as a colorless solid (0.13 g, 21% yield): MS (ES+) m/z 659.2 (M+1).

Step 7. Preparation of 4-((2-((7-azabicyclo[2.2.1]heptan-7-yl)methyl)-6-fluoro-3-methoxybenzyl)amino)-2,6-difluoro-N-(thiazol-4-yl)benzenesulfonamide 2,2,2-trifluoroacetate

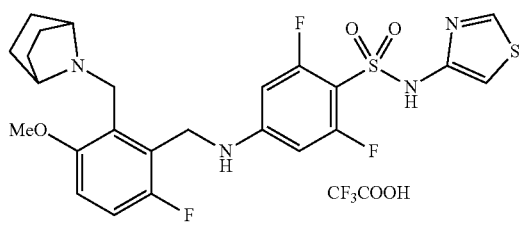 [SMILES: COc1ccc(F)c(CNc2cc(F)c(S(=O)(=O)Nc3cscn3)c(F)c2)c1CN1C2CCC1CC2 ; "CF3COOH"]

Following the procedure as described in EXAMPLE 9, Step 2 and making non-critical variations as required to replace 4-((2-((7-azabicyclo[2.2.1]heptan-7-yl)methyl)-6-fluorobenzyl)amino)-2,6-difluoro-N-(4-methoxybenzyl)-N-(thiazol-4-yl)benzenesulfonamide with 4-((2-((7-azabicyclo[2.2.1]heptan-7-yl)methyl)-6-fluoro-3-methoxybenzyl)amino)-2,6-difluoro-N-(4-methoxybenzyl)-N-(thiazol-4-yl)benzenesulfonamide, the title compound was obtained as a colorless solid (0.096 g, 75% yield): $^1$H NMR (300 MHz, DMSO-$d_6$) δ 11.23 (s, 1H), 9.18 (s, 1H), 8.90 (d, J=2.2 Hz, 1H), 7.40-7.31 (m, 1H), 7.20-7.12 (m, 1H), 6.91 (d, J=2.1 Hz, 1H), 6.58 (s, 1H), 6.40-6.31 (m, 2H), 4.39-4.29 (m, 2H), 4.24-4.01 (m, 4H), 3.86 (s, 3H), 2.26-2.09 (m, 2H), 1.97-1.81 (m, 2H), 1.77-1.51 (m, 4H); MS (ES+) m/z 539.1 (M+1).

Example 12

Synthesis of 4-((2-((7-azabicyclo[2.2.1]heptan-7-yl)methyl)-6-fluoro-3-methoxybenzyl)amino)-2,3-difluoro-N-(thiazol-4-yl)benzenesulfonamide 2,2,2-trifluoroacetate

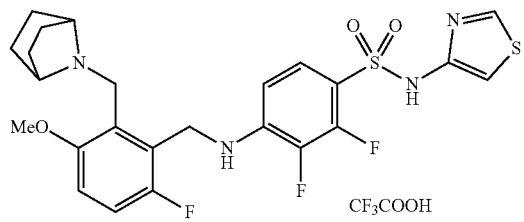 [SMILES: COc1ccc(F)c(CNc2ccc(S(=O)(=O)Nc3cscn3)c(F)c2F)c1CN1C2CCC1CC2 ; "CF3COOH"]

Step 1. Preparation of tert-butyl ((4-((2-((7-azabicyclo[2.2.1]heptan-7-yl)methyl)-6-fluoro-3-methoxybenzyl)amino)-2,3-difluorophenyl)sulfonyl)(thiazol-4-yl)carbamate

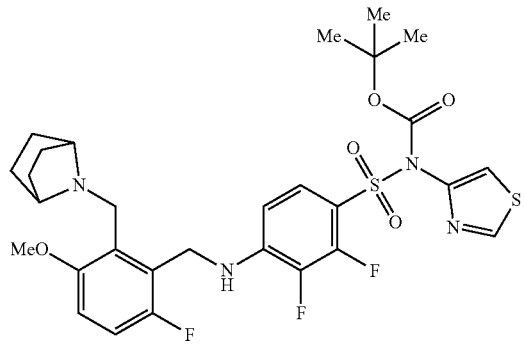 [SMILES: COc1ccc(F)c(CNc2ccc(S(=O)(=O)N(C(=O)OC(C)(C)C)c3cscn3)c(F)c2F)c1CN1C2CCC1CC2]

To a mixture of tert-butyl thiazol-4-yl((2,3,4-trifluorophenyl)sulfonyl)carbamate (0.39 g, 0.99 mmol) and (2-((7-azabicyclo[2.2.1]heptan-7-yl)methyl)-6-fluoro-3-methoxyphenyl)methanamine (0.26 g, 0.99 mmol) in anhydrous dimethyl sulfoxide (10 mL) was added potassium carbonate (0.27 g, 1.98 mmol) and the reaction mixture was stirred at ambient temperature for 16 h. The reaction mixture was diluted with saturated aqueous ammonium chloride solution (30 mL), and extracted with ethyl acetate (3×50 mL). The combined organic layers were washed with water (50 mL), brine (50 mL), dried over anhydrous magnesium sulfate, and filtered. Concentration of the filtrate in vacuo and purification of the residue by column chromatography, eluting with a gradient of 0 to 40% of ethyl acetate (containing 10% of isopropanol and 10% of triethylamine) in hexanes, provided the title compound as a colorless solid (0.12 g, 19% yield): MS (ES+) m/z 639.2 (M+1).

Step 2. Preparation of 4-((2-((7-azabicyclo[2.2.1]heptan-7-yl)methyl)-6-fluoro-3-methoxybenzyl)amino)-2,3-difluoro-N-(thiazol-4-yl)benzenesulfonamide 2,2,2-trifluoroacetate

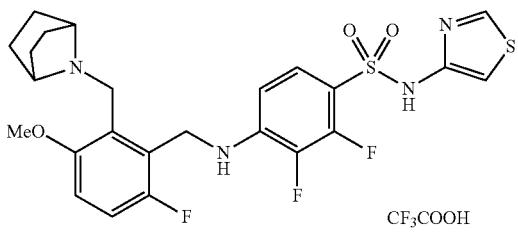 [SMILES: COc1ccc(F)c(CNc2ccc(S(=O)(=O)Nc3cscn3)c(F)c2F)c1CN1C2CCC1CC2 ; "CF3COOH"]

To a solution of tert-butyl ((4-((2-((7-azabicyclo[2.2.1]heptan-7-yl)methyl)-6-fluoro-3-methoxybenzyl)amino)-2,3-difluorophenyl)sulfonyl)(thiazol-4-yl)carbamate (0.12 g, 0.19 mmol) in dichloromethane (3 mL) was added trifluoroacetic acid (0.72 mL, 9.39 mmol). The reaction mixture was stirred at ambient temperature for 3 h, and then concentrated in vacuo. Purification of the residue by column chromatography, eluting with a gradient of 0 to 10% of methanol in dichloromethane, afforded the title compound as colorless solid (0.101 g, 81% yield): $^1$H NMR (300 MHz, DMSO-$d_6$) δ 11.21 (s, 1H), 9.07-8.84 (m, 2H), 7.49-7.41 (m, 1H), 7.37-7.29 (m, 1H), 7.19-7.10 (m, 1H), 7.09-7.01 (m, 1H), 6.99 (d, J=2.2 Hz, 1H), 6.81-6.72 (m, 1H), 4.51-4.41 (m, 2H), 4.30-3.95 (m, 4H), 3.85 (s, 3H), 2.28-2.06 (m, 2H), 1.93-1.55 (m, 6H); MS (ES+) m/z 539.0 (M+1).

Example 13

Synthesis of 4-((2-((7-azabicyclo[2.2.1]heptan-7-yl)methyl)-6-fluorobenzyl)amino)-2,3-difluoro-N-(isothiazol-3-yl)benzenesulfonamide 2,2,2-trifluoroacetate

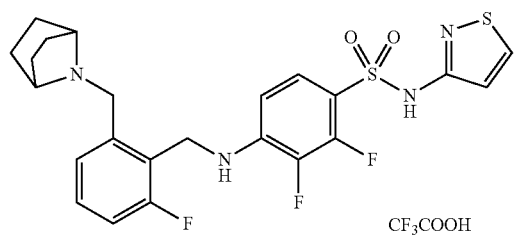 [SMILES: O=S(=O)(Nc1ccsn1)c1ccc(NCc2c(F)cccc2CN2C3CCC2CC3)c(F)c1F ; "CF3COOH"]

Step 1. Preparation of Tert-Butyl isothiazol-3-yl((2,3,4-trifluorophenyl)sulfonyl)-carbamate

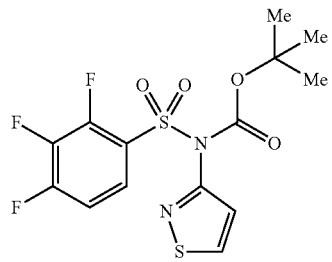 [SMILES: CC(C)(C)OC(=O)N(c1ccsn1)S(=O)(=O)c1ccc(F)c(F)c1F]

Following the procedure as described in EXAMPLE 1, Step 5 and making non-critical variations as required to replace 3-bromo-2,4,6-trifluorobenzenesulfonyl chloride with 2,3,4-trifluorobenzenesulfonyl chloride, the title compound was obtained as a colorless solid (2.74 g, 46% yield): MS (ES+) m/z 395.0 (M+1).

Step 2. Preparation of tert-butyl ((4-((2-((7-azabicyclo[2.2.1]heptan-7-yl)methyl)-6-fluorobenzyl)amino)-2,3-difluorophenyl)sulfonyl)(isothiazol-3-yl)carbamate

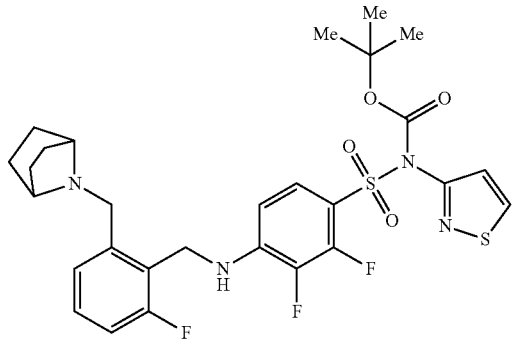 [SMILES: CC(C)(C)OC(=O)N(c1ccsn1)S(=O)(=O)c1ccc(NCc2c(F)cccc2CN2C3CCC2CC3)c(F)c1F]

To a mixture of tert-butyl isothiazol-3-yl((2,3,4-trifluorophenyl)sulfonyl)carbamate (0.51 g, 1.30 mmol) and (2-((7-azabicyclo[2.2.1]heptan-7-yl)methyl)-6-fluorophenyl)methanamine (0.31 g, 1.30 mmol) in anhydrous dimethyl sulfoxide (13 mL) was added potassium carbonate (0.36 g, 2.60 mmol) and the reaction mixture was stirred at ambient temperature for 16 h. The reaction mixture was diluted with saturated aqueous ammonium chloride solution (30 mL), and extracted with ethyl acetate (3×50 mL). The combined organic layers were washed with water (50 mL), brine (50 mL), dried over anhydrous magnesium sulfate, and filtered. Concentration of the filtrate in vacuo and purification of the residue by column chromatography, eluting with a gradient of 0 to 40% of ethyl acetate (containing 10% of isopropanol and 10% of triethylamine) in hexanes, provided the title compound as a colorless solid (0.144 g, 18% yield): MS (ES+) m/z 609.4 (M+1)

Step 3. Preparation of 4-((2-((7-azabicyclo[2.2.1]
heptan-7-yl)methyl)-6-fluorobenzyl)amino)-2,3-
difluoro-N-(isothiazol-3-yl)benzenesulfonamide 2,2,
2-trifluoroacetate

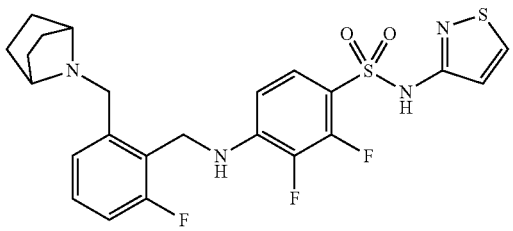 [SMILES: O=S(=O)(Nc1ccsn1)c1ccc(NCc2c(F)cccc2CN2C3CCC2CC3)c(F)c1F]

Following the procedure as described in EXAMPLE 12, Step 2 and making non-critical variations as required to replace tert-butyl ((4-((2-((7-azabicyclo[2.2.1]heptan-7-yl)methyl)-6-fluoro-3-methoxybenzyl)amino)-2,3-difluorophenyl)sulfonyl)(thiazol-4-yl)carbamate with tert-butyl ((4-((2-((7-azabicyclo[2.2.1]heptan-7-yl)methyl)-6-fluorobenzyl)amino)-2,3-difluorophenyl)sulfonyl)(isothiazol-3-yl)carbamate, the title compound was obtained as a colorless solid (0.146 g, 96% yield): $^1$H NMR (300 MHz, DMSO-$d_6$) δ 11.69 (s, 1H), 9.30 (s, 1H), 8.91 (d, J=4.7 Hz, 1H), 7.59-7.51 (m, 1H), 7.49-7.43 (m, 1H), 7.40-7.27 (m, 2H), 7.15-7.07 (m, 1H), 6.94-6.92 (m, 1H), 6.86-6.76 (m, 1H), 4.49 (dd, J=3.8, 0.4 Hz, 2H), 4.30-4.12 (m, 2H), 4.08-3.87 (m, 2H), 2.22-1.82 (m, 4H), 1.75-1.49 (m, 4H); MS (ES+) m/z 509.0 (M+1).

Example 14

Synthesis of 4-((2-(1-(7-azabicyclo[2.2.1]heptan-7-yl)ethyl)-3,6-difluorobenzyl)amino)-2,6-difluoro-N-(thiazol-4-yl)benzenesulfonamide 2,2,2-trifluoroacetate

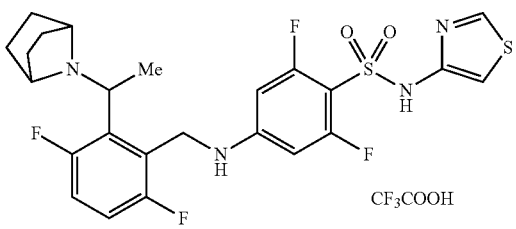 [SMILES: CC(c1c(F)ccc(F)c1CNc1cc(F)c(S(=O)(=O)Nc2cscn2)c(F)c1)N1C2CCC1CC2 ; "CF3COOH"]

Step 1. Preparation of
1-(2-bromo-3,6-difluorophenyl)ethan-1-ol

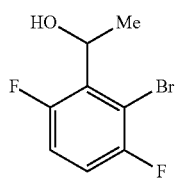

To a solution of 2-bromo-3,6-difluorobenzaldehyde (1 g, 4.53 mmol) in anhydrous diethyl ether was slowly added a 3 M solution of methylmagnesium bromide in diethyl ether (2 mL, 5 89 mmol) at −10° C. The reaction mixture was stirred at −10° C. for 3 h after which an additional amount of a 3 M solution of methylmagnesium bromide in diethyl ether (4.53 mL, 13.59 mmol) was added dropwise to it. The reaction mixture was stirred at −10° C. for 1 h, and then poured into a stirred saturated aqueous ammonium chloride solution at 0° C. in small portions. The mixture was extracted with ethyl acetate (3×50 mL). The combined organic layers were washed with brine (50 mL), dried over anhydrous magnesium sulfate, and filtered. Concentration of the filtrate in vacuo and purification of the residue by column chromatography, eluting with a gradient of 0 to 20% of ethyl acetate in hexanes, provided the title compound as a colorless oil (0.97 g, 91% yield): $^1$H NMR (300 MHz, CDCl$_3$) δ 7.07-6.99 (m, 2H), 5.41-5.30 (m, 1H), 2.56-2.44 (m, 1H), 1.65-1.59 (m, 3H); MS (ES+) m/z 260.2 (M+23), 262.1 (M+23).

Step 2. Preparation of
2-bromo-3-(1-bromoethyl)-1,4-difluorobenzene

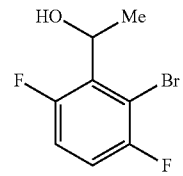

Following the procedure as described in EXAMPLE 10, Step 1 and making non-critical variations as required to replace (2-bromo-3,6-difluorophenyl)methanol with 1-(2-bromo-3,6-difluorophenyl)ethan-1-ol, the title compound was obtained as a colorless solid (8.24 g, 65% yield): $^1$H NMR (300 MHz, CDCl$_3$) δ 7.12-6.99 (m, 2H), 5.72-5.57 (m, 1H), 2.18-2.04 (m, 3H).

Step 3. Preparation of 7-(1-(2-bromo-3,6-difluorophenyl)ethyl)-7-azabicyclo[2.2.1]heptane

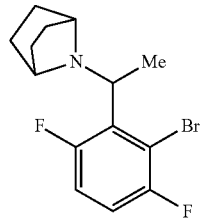 [SMILES: CC(c1c(F)ccc(F)c1Br)N1C2CCC1CC2]

To a mixture of 2-bromo-3-(1-bromoethyl)-1,4-difluorobenzene (4.2 g, 14.0 mmol) and 7-azabicyclo[2.2.1]heptane hydrochloride (1.87 g, 14.0 mmol) in anhydrous dimethyl sulfoxide (25 mL) was added potassium carbonate (3.87 g, 28.0 mmol). The reaction mixture was stirred at ambient temperature for 16 h, and then at 80° C. for 4 h. The reaction mixture was allowed to cool to ambient temperature, diluted with water (100 mL), and extracted with ethyl acetate (3×60 mL). The combined organic layers were washed with brine (80 mL), dried over anhydrous sodium sulfate, and filtered. Concentration of the filtrate in vacuo and purification of the residue by column chromatography, eluting with a gradient of 0 to 10% methanol in dichloromethane, afforded the title compound as a pale yellow oil (2.83 g, 64% yield): MS (ES+) m/z 316.1 (M+1), 318.1 (M+1).

Step 4. Preparation of (E)-2-(1-(7-azabicyclo[2.2.1]heptan-7-yl)ethyl)-3,6-difluorobenzaldehyde Oxime

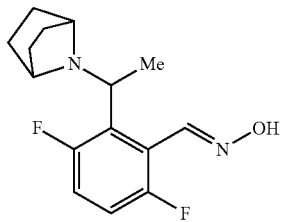 [SMILES: CC(c1c(F)ccc(F)c1/C=N/O)N1C2CCC1CC2]

Following the procedure as described in EXAMPLE 2, Step 6 and making non-critical variations as required to replace N-(2-bromo-3-fluoro-6-methoxybenzyl)-N-methylpropan-2-amine with 7-(1-(2-bromo-3,6-difluorophenyl)ethyl)-7-azabicyclo[2.2.1]heptane, the title compound was obtained as a colorless solid (0.635 g, 27% yield): MS (ES+) m/z 281.2 (M+1).

Step 5. Preparation of (2-(1-(7-azabicyclo[2.2.1]heptan-7-yl)ethyl)-3,6-difluorophenyl)methanamine

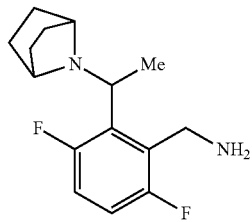 [SMILES: CC(c1c(F)ccc(F)c1CN)N1C2CCC1CC2]

Following the procedure as described in EXAMPLE 2, Step 7 and making non-critical variations as required to replace (E)-6-fluoro-2-((isopropyl(methyl)amino)methyl)-3-methoxybenzaldehyde oxime with (E)-2-(1-(7-azabicyclo[2.2.1]heptan-7-yl)ethyl)-3,6-difluorobenzaldehyde oxime, the title compound was obtained as a pale yellow oil (0.53 g, 88% yield): MS (ES+) m/z 267.2 (M+1).

Step 6. Preparation of tert-butyl ((4-((2-(1-(7-azabicyclo[2.2.1]heptan-7-yl)ethyl)-3,6-difluorobenzyl)amino)-2,6-difluorophenyl)sulfonyl)(thiazol-4-yl)carbamate

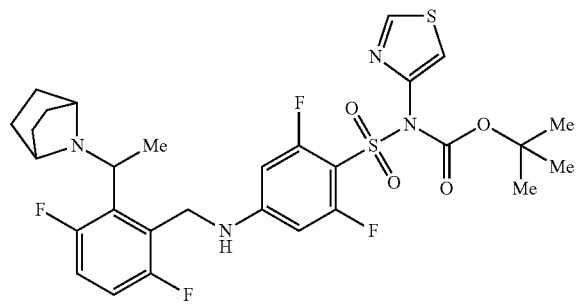 [SMILES: CC(c1c(F)ccc(F)c1CNc1cc(F)c(S(=O)(=O)N(C(=O)OC(C)(C)C)c2cscn2)c(F)c1)N1C2CCC1CC2]

To a mixture tert-butyl thiazol-4-yl((2,4,6-trifluorophenyl)sulfonyl)carbamate (0.77 g, 1.95 mmol) and (2-(1-(7-azabicyclo[2.2.1]heptan-7-yl)ethyl)-3,6-difluorophenyl)methanamine (0.52 g, 1.95 mmol) in anhydrous dimethyl sulfoxide (20 mL) was added N,N-diisopropylethylamine (1.02 mL, 5.85 mmol) and the reaction mixture was stirred at ambient temperature for 16 h. The reaction mixture was diluted with saturated aqueous ammonium chloride solution (30 mL), and extracted with ethyl acetate (3×50 mL). The combined organic layers were washed with water (50 mL), brine (50 mL), dried over anhydrous magnesium sulfate, and filtered. Concentration of the filtrate in vacuo and purification of the residue by column chromatography, eluting with a gradient of 0 to 40% of ethyl acetate (containing 10% of isopropanol and 10% of triethylamine) in hexanes, provided the title compound as a colorless solid (0.58 g, 46% yield): MS (ES+) m/z 641.3 (M+1).

Step 7. Preparation of 4-((2-(1-(7-azabicyclo[2.2.1]heptan-7-yl)ethyl)-3,6-difluorobenzyl)amino)-2,6-difluoro-N-(thiazol-4-yl)benzenesulfonamide 2,2,2-trifluoroacetate

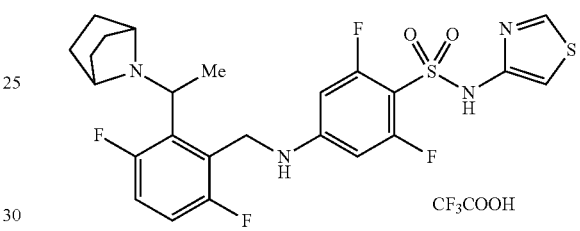

Following the procedure as described in EXAMPLE 12, Step 2 and making non-critical variations as required to replace tert-butyl ((4-((2-((7-azabicyclo[2.2.1]heptan-7-yl)methyl)-6-fluoro-3-methoxybenzyl)amino)-2,3-difluorophenyl)sulfonyl)(thiazol-4-yl)carbamate with tert-butyl ((4-((2-(1-(7-azabicyclo[2.2.1]heptan-7-yl)ethyl)-3,6-difluorobenzyl)amino)-2,6-difluorophenyl)sulfonyl)(thiazol-4-yl)carbamate, the title compound was obtained as a colorless solid (0.47 g, 83% yield): $^1$H NMR (300 MHz, DMSO-$d_6$) δ 11.24 (s, 1H), 9.49-9.34 (m, 1H), 8.90 (d, J=2.2 Hz, 1H), 7.57-7.44 (m, 2H), 7.45-7.36 (m, 1H), 6.92 (d, J=2.2 Hz, 1H), 6.45-6.31 (m, 2H), 4.47-4.11 (m, 4H), 3.60 (s, 1H), 2.28-2.08 (m, 2H), 1.98-1.47 (m, 9H); MS (ES+) m/z 541.3 (M+1).

Example 15A and 15B

Synthesis of (S)-4-((2-(1-(7-azabicyclo[2.2.1]heptan-7-yl)ethyl)-3,6-difluorobenzyl)amino)-2,6-difluoro-N-(thiazol-4-yl)benzenesulfonamide and (R)-4-((2-(1-(7-azabicyclo[2.2.1]heptan-7-yl)ethyl)-3,6-difluorobenzyl)amino)-2,6-difluoro-N-(thiazol-4-yl)benzenesulfonamide

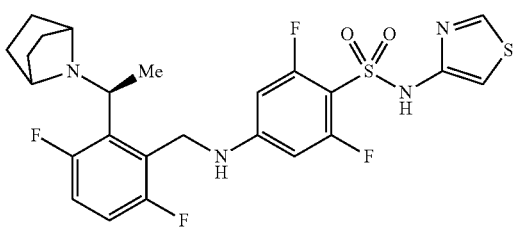

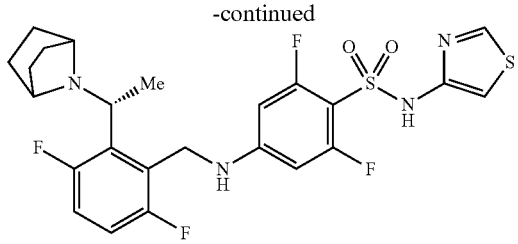

To a mixture of 4-((2-(1-(7-azabicyclo[2.2.1]heptan-7-yl)ethyl)-3,6-difluorobenzyl)amino)-2,6-difluoro-N-(thiazol-4-yl)benzenesulfonamide 2,2,2-trifluoroacetate (0.100 g, 0.153 mmol) in ethyl acetate (50 mL) and water (10 mL) was added aqueous ammonium hydroxide (0.2 mL of a 25-28% solution). The reaction mixture was stirred at 25° C. for 30 minutes. The organic layer was separated, dried over anhydrous sodium sulfate, and filtered. The filtrate was concentrated under reduced pressure. Purification and resolution of the residue by preparative supercritical fluid chromatography, using 30% of ethanol (containing 0.1% of ammonium hydroxide) in supercritical carbon dioxide as eluent and a Chiralpak AS column (250×30 mm, 5 μm), provided (S)-4-((2-(1-(7-azabicyclo[2.2.1]heptan-7-yl)ethyl)-3,6-difluorobenzyl)amino)-2,6-difluoro-N-(thiazol-4-yl)benzenesulfonamide (colorless solid, 0.014 g, 17% yield, 99% ee) as the first eluting enantiomer and (R)-4-((2-(1-(7-azabicyclo[2.2.1]heptan-7-yl)ethyl)-3,6-difluorobenzyl)amino)-2,6-difluoro-N-(thiazol-4-yl)benzenesulfonamide (colorless solid, 0.015 g, 18% yield, 96% ee) as the second eluting enantiomer. The absolute configuration was arbitrarily assigned. Data for (S)-4-((2-(1-(7-azabicyclo[2.2.1]heptan-7-yl)ethyl)-3,6-difluorobenzyl)amino)-2,6-difluoro-N-(thiazol-4-yl)benzenesulfonamide: $^1$H NMR (400 MHz, CDCl$_3$) δ 8.65 (d, J=2.4 Hz, 1H), 7.04 (d, J=2.4 Hz, 1H), 6.97-7.00 (m, 2H), 6.10-6.13 (m, 2H), 4.72 (d, J=13.6 Hz, 1H), 4.43 (dd, J=13.6, 2.8 Hz, 1H), 4.13-4.19 (m, 1H), 3.62 (brs, 1H), 2.93 (m, 1H), 1.90-1.96 (m, 2H), 1.72-1.78 (m, 2H), 1.41-1.43 (m, 4H), 1.28-1.37 (m, 3H), 2 NH not observed; $^{19}$F NMR (376 MHz, CDCl$_3$) δ −107.8 (s, 2F), −119.0 (d, J=17.6, 1F), −119.6 (d, J=17.5, 1F); MS (ES+) m/z 541.4 (M+1). Data for (R)-4-((2-(1-(7-azabicyclo[2.2.1]heptan-7-yl)ethyl)-3,6-difluorobenzyl)amino)-2,6-difluoro-N-(thiazol-4-yl)benzenesulfonamide: $^1$H NMR (400 MHz, CDCl$_3$) δ 8.62 (d, J=2.4 Hz, 1H), 7.03 (d, J=2.4 Hz, 1H), 6.90-7.00 (m, 2H), 6.10-6.13 (m, 2H), 4.72 (d, J=13.6 Hz, 1H), 4.42 (dd, J=13.6, 2.8 Hz, 1H), 4.13-4.18 (m, 1H), 3.62 (brs, 1H), 2.93 (m, 1H), 1.90-1.96 (m, 2H), 1.72-1.78 (m, 2H), 1.41-1.43 (m, 4H), 1.28-1.37 (m, 3H), 2 NH not observed; $^{19}$F NMR (376 MHz, CDCl$_3$) δ −107.7 (s, 2F), −119.0 (d, J=17.5, 1F), −119.6 (d, J=17.4, 1F); MS (ES+) m/z 541.4 (M+1).

Example 16

Synthesis of 2,3-difluoro-4-((6-fluoro-2-((isopropyl(methyl)amino)methyl)-3-methoxybenzyl)amino)-N-(thiazol-4-yl)benzenesulfonamide

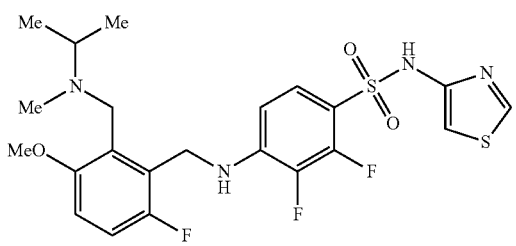 [SMILES: COc1ccc(F)c(CNc2ccc(S(=O)(=O)Nc3cscn3)c(F)c2F)c1CN(C)C(C)C]

Step 1. Preparation of tert-butyl ((2,3-difluoro-4-((6-fluoro-2-((isopropyl(methyl)amino)methyl)-3-methoxybenzyl)amino)phenyl)sulfonyl)(thiazol-4-yl)carbamate

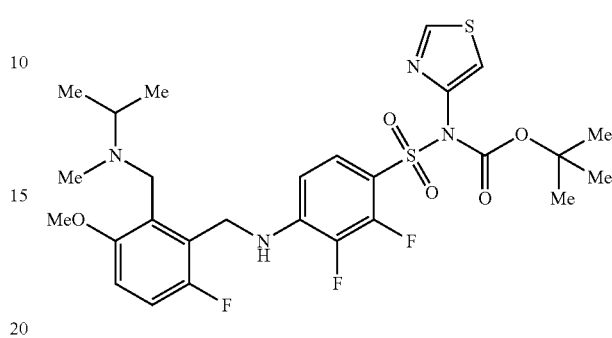

Following the procedure as described in EXAMPLE 12, Step 1 and making non-critical variations as required to replace (2-((7-azabicyclo[2.2.1]heptan-7-yl)methyl)-6-fluoro-3-methoxyphenyl)methanamine with of N-(2-(aminomethyl)-3-fluoro-6-methoxybenzyl)-N-methylpropan-2-amine, the title compound was obtained as a colorless solid (0.06 g, 12% yield): MS (ES+) m/z 615.2 (M+1).

Step 2. Preparation of 2,3-difluoro-4-((6-fluoro-2-((isopropyl(methyl)amino)methyl)-3-methoxybenzyl)amino)-N-(thiazol-4-yl)benzenesulfonamide

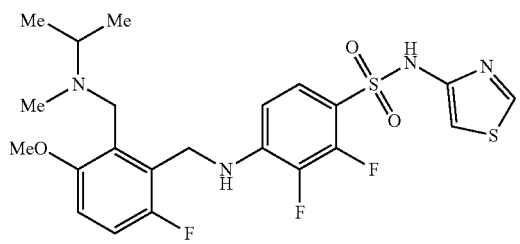 [SMILES: COc1ccc(F)c(CNc2ccc(S(=O)(=O)Nc3cscn3)c(F)c2F)c1CN(C)C(C)C]

Following the procedure as described in EXAMPLE 12, Step 2 and making non-critical variations as required to replace tert-butyl ((4-((2-((7-azabicyclo[2.2.1]heptan-7-yl)methyl)-6-fluoro-3-methoxybenzyl)amino)-2,3-difluorophenyl)sulfonyl)(thiazol-4-yl)carbamate with tert-butyl ((2,3-difluoro-4-((6-fluoro-2-((isopropyl(methyl)amino)methyl)-3-methoxybenzyl)amino)phenyl)sulfonyl)(thiazol-4-yl)carbamate, the title compound was obtained as a colorless solid (0.059, 97%): $^1$H NMR (300 MHz, DMSO-d$_6$) δ 11.09 (s, 1H), 8.88 (d, J=2.2 Hz, 1H), 7.69 (s, 1H), 7.47-7.38 (m, 1H), 7.26-7.13 (m, 1H), 7.09-7.01 (m, 1H), 6.99-6.95 (m, 1H), 6.89-6.76 (m, 1H), 4.52-4.37 (m, 2H), 3.95-3.61 (m, 5H), 2.91 (br s, 1H), 2.09 (br s, 3H), 1.08 (br s, 6H); MS (ES+) m/z 515.1 (M+1).

Example 17

Synthesis of 5-chloro-2-fluoro-4-((6-fluoro-2-((isopropyl(methyl)amino)methyl)-3-methoxybenzyl)amino)-N-(thiazol-4-yl)benzenesulfonamide 2,2,2-trifluoroacetate

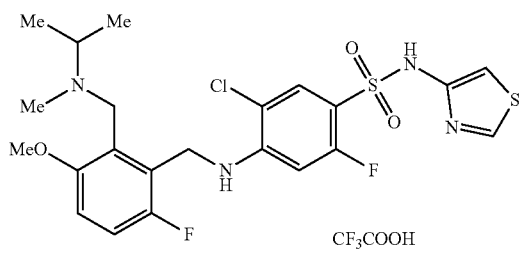 [SMILES: COc1ccc(F)c(CNc2cc(F)c(S(=O)(=O)Nc3cscn3)cc2Cl)c1CN(C)C(C)C ; "CF3COOH"]

Step 1. Preparation of tert-butyl ((5-chloro-2-fluoro-4-((6-fluoro-2-((isopropyl(methyl)amino)methyl)-3-methoxybenzyl)amino)phenyl)sulfonyl)(thiazol-4-yl)carbamate

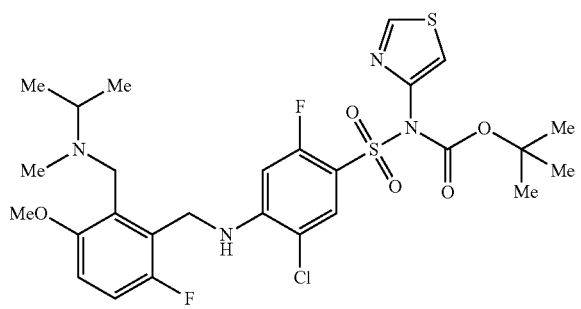 [SMILES: COc1ccc(F)c(CNc2cc(F)c(S(=O)(=O)N(C(=O)OC(C)(C)C)c3cscn3)cc2Cl)c1CN(C)C(C)C]

To a mixture of tert-butyl ((5-chloro-2,4-difluorophenyl)sulfonyl)(thiazol-4-yl)carbamate (0.85 g, 2.08 mmol, prepared according to U.S. Published Patent Application No. 2017/0334902) and N-(2-(aminomethyl)-3-fluoro-6-methoxybenzyl)-N-methylpropan-2-amine (0.50 g, 2.08 mmol) in anhydrous dimethyl sulfoxide (17 mL) was added N,N-diisopropylethylamine (1.09 mL, 6.24 mmol) and the reaction mixture was stirred at ambient temperature for 16 h. The reaction mixture was diluted with saturated aqueous ammonium chloride solution (30 mL), and extracted with ethyl acetate (3×50 mL). The combined organic layers were washed with water (50 mL), brine (50 mL), dried over anhydrous magnesium sulfate, and filtered. Concentration in vacuo and purification of the residue by column chromatography, eluting with a gradient of 0 to 40% of ethyl acetate (containing 10% of isopropanol and 10% of triethylamine) in hexanes, provided the title compound as a colorless solid (0.60 g, 46% yield): MS (ES+) m/z 631.1 (M+1), 633.1 (M+1).

Step 2. Preparation of 5-chloro-2-fluoro-4-((6-fluoro-2-((isopropyl(methyl)amino)methyl)-3-methoxybenzyl)amino)-N-(thiazol-4-yl)benzenesulfonamide 2,2,2-trifluoroacetate

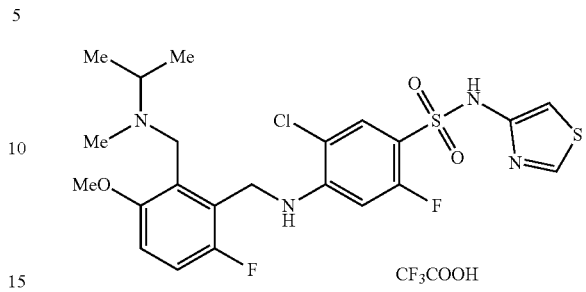

Following the procedure as described in EXAMPLE 12, Step 2 and making non-critical variations as required to replace tert-butyl ((4-((2-((7-azabicyclo[2.2.1]heptan-7-yl)methyl)-6-fluoro-3-methoxybenzyl)amino)-2,3-difluorophenyl)sulfonyl)(thiazol-4-yl)carbamate with tert-butyl ((5-chloro-2-fluoro-4-((6-fluoro-2-((isopropyl(methyl)amino)methyl)-3-methoxybenzyl)amino)phenyl)sulfonyl)(thiazol-4-yl)carbamate the title compound was obtained as a colorless solid (0.139, 90%): $^1$H NMR (300 MHz, DMSO-$d_6$) δ 11.17 (s, 1H), 8.88 (d, J=2.2 Hz, 1H), 8.42 (s, 1H), 7.61 (d, J=7.4 Hz, 1H), 7.42-7.36 (m, 1H), 7.21-7.09 (m, 1H), 7.00 (t, J=1.9 Hz, 1H), 6.86-6.78 (m, 1H), 6.75-6.71 (m, 1H), 4.59-4.36 (m, 3H), 4.21-4.06 (m, 1H), 3.83 (s, 3H), 3.68-3.54 (m, 1H), 2.59 (d, J=4.3 Hz, 3H), 1.33 (dd, J=15.4, 6.4 Hz, 6H); MS (ES+) m/z 531.0 (M+1), 533.0 (M+1).

Example 18

Synthesis of 2-fluoro-4-((6-fluoro-2-((isopropyl(methyl)amino)methyl)-3-methoxybenzyl)amino)-5-methyl-N-(thiazol-4-yl)benzenesulfonamide 2,2,2-trifluoroacetate

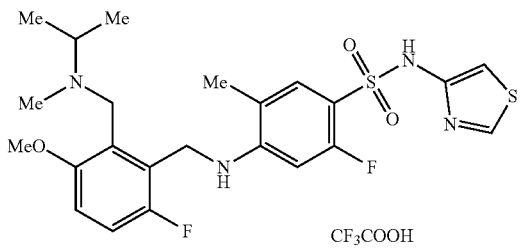 [SMILES: COc1ccc(F)c(CNc2cc(F)c(S(=O)(=O)Nc3cscn3)cc2C)c1CN(C)C(C)C ; "CF3COOH"]

Step 1. Preparation of tert-butyl ((2-fluoro-4-((6-fluoro-2-((isopropyl(methyl)amino)methyl)-3-methoxybenzyl)amino)-5-methylphenyl)sulfonyl)(thiazol-4-yl)carbamate

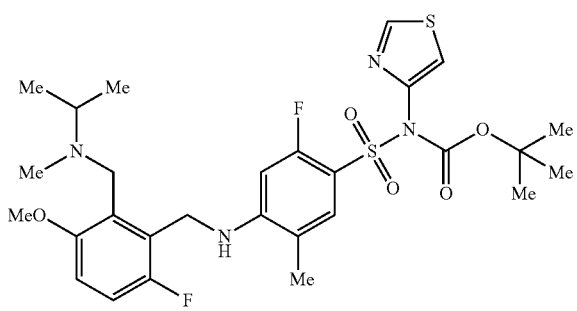

To a mixture of tert-butyl ((5-chloro-2-fluoro-4-((6-fluoro-2-((isopropyl(methyl)amino)methyl)-3-methoxybenzyl)amino)phenyl)sulfonyl)(thiazol-4-yl)carbamate (0.26 g, 0.41 mmol) and methylboronic acid (0.196 g, 3.28 mmol) in anhydrous 1,4-dioxane (10 mL) was added potassium phosphate tribasic (0.21 g, 1.24 mmol) and the mixture was purged with argon for 20 minutes. To it was then tricyclohexylphosphonium tetrafluoroborate (0.45 g, 0.12 mmol) and palladium(II) acetate (0.014 g, 0.062 mmol) and the resulting mixture was heated at 105° C. After cooling to ambient temperature, the reaction mixture was filtered through a pad of celite. The filter pad was washed with ethyl acetate (20 mL) and the combined filtrate was concentrated in vacuo. The obtained residue was diluted with saturated aqueous ammonium chloride solution (20 mL), and extracted with ethyl acetate (3×30 mL). The combined organic layers were washed with brine (40 mL), dried over anhydrous magnesium sulfate, and filtered. Concentration of the filtrate in vacuo and purification of the residue by column chromatography, eluting with a gradient of 0 to 10% of methanol in dichloromethane, provided the title compound as a pale brown oil (0.25 g, quantitative yield): MS (ES+) m/z 611.1 (M+1).

Step 2. Preparation of 2-fluoro-4-((6-fluoro-2-((isopropyl(methyl)amino)methyl)-3-methoxybenzyl)amino)-5-methyl-N-(thiazol-4-yl)benzenesulfonamide 2,2,2-trifluoroacetate

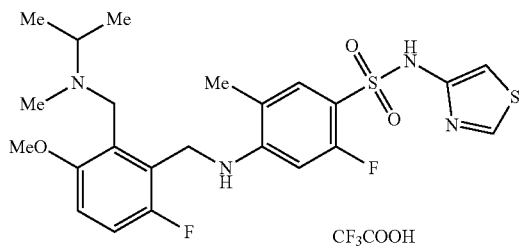 [SMILES: COc1ccc(F)c(CNc2cc(F)c(S(=O)(=O)Nc3cscn3)cc2C)c1CN(C)C(C)C ; "CF3COOH"]

Following the procedure as described in EXAMPLE 12, Step 2 and making non-critical variations as required to replace tert-butyl ((4-((2-((7-azabicyclo[2.2.1]heptan-7-yl)methyl)-6-fluoro-3-methoxybenzyl)amino)-2,3-difluorophenyl)sulfonyl)(thiazol-4-yl)carbamate with tert-butyl ((2-fluoro-4-((6-fluoro-2-((isopropyl(methyl)amino)methyl)-3-methoxybenzyl)amino)-5-methylphenyl)sulfonyl)(thiazol-4-yl)carbamate, the title compound was obtained as a colorless solid (0.131, 51%): $^1$H NMR (300 MHz, DMSO-$d_6$) δ 11.00 (s, 1H), 8.86 (d, J=2.2 Hz, 1H), 8.42 (s, 1H), 7.44-7.35 (m, 2H), 7.19-7.12 (m, 1H), 6.88 (d, J=2.2 Hz, 1H), 6.49 (d, J=13.7 Hz, 1H), 6.28-6.21 (m, 1H), 4.50-4.30 (m, 3H), 4.18-4.05 (m, 1H), 3.84 (s, 3H), 3.66-3.52 (m, 1H), 2.60 (d, J=4.8 Hz, 3H), 2.03 (s, 3H), 1.31 (dd, J=15.0, 6.5 Hz, 6H); MS (ES+) m/z 511.1 (M+1).

Biological Assays

Various techniques are known in the art for testing the activity of the compound of the invention or determining their solubility in known pharmaceutically acceptable excipients. In order that the invention described herein may be more fully understood, the following biological assays are set forth. It should be understood that these examples are for illustrative purposes only and are not to be construed as limiting this invention in any manner.

Biological Example 1

Electrophysiological Assay (In Vitro Assay)

Patch voltage clamp electrophysiology allows for the direct measurement and quantification of block of voltage-gated sodium channels ($Na_V$'s), and allows the determination of the time- and voltage-dependence of block which has been interpreted as differential binding to the resting, open, and inactivated states of the sodium channel (Hille, B., *Journal of General Physiology* (1977), 69: 497-515).

The following patch voltage clamp electrophysiology studies may be performed on representative compounds of the invention using human embryonic kidney cells (HEK), permanently transfected with an expression vector containing the full-length cDNA coding for the desired human sodium channel α-subunit, grown in culture media containing 10% FBS, 1% PSG, and 0.5 mg/mL G418 at 37° C. with 5% $CO_2$. HEK cells used for the electrophysiology (EP) recordings have a passage number of less than 40 for all studies and are used within three days from the time of plating. $Na_V1.1$, $Na_V1.5$ and $Na_V1.6$ cDNAs (NM_001165964 (SCN1A), NM_000335 (SCN5A) and NM_014191 (SCN8A), respectively) are stably expressed in HEK-293 cells.

Sodium currents are measured using the patch clamp technique in the whole-cell configuration using either a PatchXpress automated voltage clamp or manually using an Axopatch 200B (Axon Instruments) or Model 2400 (A-M systems) amplifier. The manual voltage clamp protocol is as follows: Borosilicate glass micropipettes are fire-polished to a tip diameter yielding a resistance of 2-4 Mohms in the working solutions. The pipette is filled with a solution comprised of: 5 mM NaCl, 10 mM CsCl, 120 mM CsF, 0.1 mM $CaCl_2$, 2 mM $MgCl_2$, 10 mM HEPES, 10 mM EGTA; and adjusted to pH 7.2 with CsOH. The external solution has the following composition: 140 mM NaCl, 5 mM KCl, 2 mM $CaCl_2$, 1 mM $MgCl_2$, 10 mM HEPES; and adjusted to pH 7.4 with NaOH. In some studies, the external sodium can be reduced by equimolar replacement with choline. Osmolarity in the CsF internal and NaCl external solutions is adjusted to 300 mOsm/kg and 310 mOsm/kg with glucose, respectively. All recordings are performed at ambient temperature in a bath chamber with a volume of 150 μL. Control sodium currents are measured in 0.5% DMSO. Controls and representative compounds of the invention are applied to the recording chamber through a 4-pinch or 8-pinch valve bath perfusion system manufactured by ALA Scientific Instruments.

Currents are recorded at 40 kHz sampling frequency, filtered at 5 Hz, and stored using a Digidata-1322A analogue/digital interface with the pClamp software (Axon Instruments). Series resistance compensation is applied (60-80%). Cells are rejected if currents showed inadequate voltage control (as judged by the IV relationship during stepwise activation). All statistics in this study are to be given as mean±SD.

The membrane potential is maintained at a voltage where inactivation of the channel is complete. The voltage is then stepped back to a very negative (Vhold=−150 mV) voltage for 20 ms and then a test pulse is applied to quantify the compound block. The 20 ms brief repolarization is long enough for compound-free channels to completely recover from fast inactivation, but the compound-bound channels recover more slowly such that negligible recovery could occur during this interval. The percent decrease in sodium current following wash-on of compound is taken as the percent block of sodium channels.

Biological Example 2

Sodium Influx Assay (In Vitro Assay)

This sodium influx assay employs the use of the cell permeable, sodium sensitive dye ANG2 to quantify sodium ion influx through sodium channels which are maintained in an open state by use of sodium channel modulators. This high throughput sodium influx assay allows for rapid profiling and characterization of sodium channel blockers.

In general, Trex HEK293 cells were stably transfected with an inducible expression vector containing the full-length cDNA coding for the desired human sodium channel α-subunit and with an expression vector containing full length cDNA coding for the β1-subunit. Sodium channel expressing cell lines were induced with tetracycline (1 μg/mL) and plated on 384-well PDL-coated plates at a density of 25K-30K cells/well in culture media (DMEM, containing 10% FBS and 1% L-glutamine). After overnight incubation (37° C., 5% $CO_2$), culture media was removed and cells were loaded with 5 uM ANG2 dye for 1-1.5 h in Buffer 1 (155 mM NMDG, 5 mM KCl, 2 mM $CaCl_2$, 1 mM $MgCl_2$, 10 mM HEPES, 10 mM glucose, adjusted with Tris to pH 7.4). Access dye was removed and cells were incubated with test compounds for 1 hr in buffer 1 containing sodium channel modulator(s) at room temperature. Hamamatsu FDSS μCell was used to perform a 1:1 addition of Na/K challenge buffer (140 mM NaCl, 20 mM HEPES, 1 mM $CaCl_2$, 15 mM KCl, 1 mM $MgCl_2$, 10 mM glucose, adjusted with Tris to pH 7.4) and simultaneously read plates at excitation wavelength of 530 nm and emission wavelength set at 558 nm. Percent inhibition of sodium ion influx was calculated for each test compound at each test concentration to determine the $IC_{50}$ values.

Representative compounds of the invention, when tested in this model, demonstrated affinities for the inactivated state of $Na_V1.6$, $Na_V1.5$ and $Na_V1.1$ as set forth below in Table 1.

The Example numbers provided in Table 1 correspond to the Example numbers herein and "Flux" refers to the Sodium Influx Assay:

TABLE 1

Inhibition of Nav1.1, Nav1.5, and $Na_V1.6$

| Ex. No. | Flux $Na_V1.6$ $IC_{50}$ (μM) | Flux $Na_V1.5$ $IC_{50}$ (μM) | Flux $Na_V1.1$ $IC_{50}$ (μM) |
| --- | --- | --- | --- |
| 1 | 0.015 | >30.000 | 9.603 |
| 2 | 0.027 | 28.259 | 27.539 |
| 3 | 0.142 | >30.000 | >30.000 |
| 4 | 0.047 | >30.000 | 16.982 |
| 5 | 0.617 | >30.000 | >30.000 |
| 6 | 0.095 | 15.272 | 5.227 |
| 7 | 0.181 | 21.314 | 7.441 |
| 8 | 0.026 | 11.074 | 27.982 |
| 9 | 0.026 | 20.428 | 7.845 |
| 10 | 0.028 | 25.357 | 7.932 |
| 11 | 0.002 | 27.488 | 5.911 |
| 12 | 0.054 | >30.000 | >30.000 |
| 13 | 0.270 | >30.000 | 23.741 |
| 14 | 0.653 | 12.787 | >30.000 |
| 15a | 0.530 | >30.000 | >30.000 |
| 15b | 0.821 | >30.000 | >30.000 |
| 16 | 0.031 | 9.459 | >30.000 |
| 17 | 0.012 | 16.285 | >30.000 |
| 18 | 0.016 | 11.817 | >30.000 |

Biological Example 3

Electrical Stimulation Seizure Assays

Many electric stimulation seizure tests have been used to identify compounds with anti-convulsion activity, i.e., which raise seizure threshold. Two examples of electrical stimulation seizure assays frequently used in the field are the 6 Hz psychomotor seizure assay (6 Hz) and the Maximal Electroshock Seizure (MES). The 6 Hz assay is considered a model of partial seizures observed in humans (Löscher, W. and Schmidt, D., *Epilepsy Res*. (1988), Vol. 2, pp 145-81; Barton, M. E. et al., *Epilepsy Res*. (2001), Vol. 47, pp. 217-27). The MES assay is a model for generalized tonic-clonic seizures in humans and provides an indication of a compound's ability to prevent seizure spread when all neuronal circuits in the brain are maximally active. These seizures are highly reproducible and are electrophysiologically consistent with human seizures (Toman et al., 1946; Piredda et al., 1984; White et al., 1995). Experiments can be performed with healthy animals, or with seizure prone animals that have been genetically modified to model genetic epilepsy syndromes (Piredda, S. G. et al., *J. Pharmacol. Exp. Ther*. (1985), Vol. 232, pp. 741-5; Toman, J. E. et al., *J. Neurophysiol*. (1946), Vol. 9, pp. 231-9; and White, H. S. et al., *Ital. J. Neurol. Sci*. (1995), Vol. 16 (1-2), pp. 73-7).

To facilitate testing mice can be pretreated with the test compound or with the appropriate vehicle prior to the application of the electroshock. Each treatment group (n=4-8 mice/group) is examined for anticonvulsive effects at different time points after administration of the compound and the vehicle. The eyes of mice are first anesthetized with a topical application of Alcaine (proparacaine hydrochloride) 0.5%, one drop in each eye 30 minutes prior to the stimulation. Seizures are then induced by placing electrodes on the eyes which deliver a transcorneal current.

The 6 Hz Psychomotor Seizure Test:

Following pretreatment, each mouse is challenged with the low-frequency (6 Hz, 0.3 ms pulse width) stimulation for 3 sec. delivered through corneal electrodes at several intensities (12-44 mA). Animals are manually restrained and released immediately following the stimulation and observed for the presence or absence of seizure activity. Typically, the 6 Hz stimulation results in a seizure characterized by a minimal clonic phase that is followed by stereotyped, automatist behaviors, including twitching of the vibrissae, and Straub-tail or by a generalized tonic clonic seizure. The presence, type and latency to seizure (in seconds) after the application of the current are monitored. Animals not displaying a clonic or generalized tonic clonic seizure are considered "protected". All animals are euthanized at the end of assay. Plasma and brain samples are collected.

Maximal Electroshock Test (MES):

Following pretreatment, each mouse is challenged with an alternating current (60 Hz, 0.4-0.6 ms pulse width) for 0.2-0.5 sec. delivered through corneal electrodes at intensities (44-55 mA).

Typically, the MES stimulation results in a generalized tonic seizure that can be followed by a clonic seizure, automatist behaviors and Straub-tail. The presence, type and latency to seizure (in seconds) after the application of the current are monitored. An animal is considered "protected" from MES-induced seizures upon abolition of the hindlimb tonic extensor component of the seizure. After the seizure, mice are expected to resume normal exploratory behaviour within 1 to 4 minutes. Latency to seizure is recorded with a cut-off of 1 minute after which all animals are euthanized.

All of the U.S. patents, U.S. patent application publications, U.S. patent applications, foreign patents, foreign patent applications and non-patent publications referred to in this specification are incorporated herein by reference in their entireties.

Although the foregoing invention has been described in some detail to facilitate understanding, it will be apparent that certain changes and modifications may be practiced within the scope of the appended claims. Accordingly, the described embodiments are to be considered as illustrative and not restrictive, and the invention is not to be limited to the details given herein, but may be modified within the scope and equivalents of the appended claims.

What is claimed is:

1. A compound of formula (I):

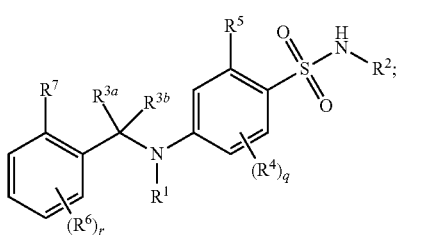

as an individual stereoisomer, enantiomer or tautomer thereof or a mixture thereof;
or a pharmaceutically acceptable salt or solvate thereof, wherein:
q is 1 or 2;
r is 1 or 2;
$R^1$ is hydrogen or alkyl;
$R^2$ is thiazolyl, isothiazolyl or isoxazolyl;
$R^{3a}$ and $R^{3b}$ are each independently hydrogen or alkyl;
each $R^4$ is independently halo or alkyl;
$R^5$ is halo;
each $R^6$ is independently halo or alkoxy; and
$R^7$ is azabicyclo[2.2.1]heptanylalkyl or $R^7$ is ((methyl)(prop-2-yl)amino)alkyl when r is 2 and at least one $R^6$ is alkoxy.

2. The compound of claim 1, as an individual stereoisomer, enantiomer or tautomer thereof or a mixture thereof; or a pharmaceutically acceptable salt or solvate thereof, wherein $R^7$ is azabicyclo[2.2.1]heptanylalkyl.

3. The compound of claim 2, as an individual stereoisomer, enantiomer or tautomer thereof or a mixture thereof; or a pharmaceutically acceptable salt or solvate thereof, wherein $R^2$ is isothiazolyl.

4. The compound of claim 3 selected from:
4-((2-((7-azabicyclo[2.2.1]heptan-7-yl)methyl)-6-fluorobenzyl)amino)-2,6-difluoro-N-(isothiazol-3-yl)benzenesulfonamide; and
4-((2-((7-azabicyclo[2.2.1]heptan-7-yl)methyl)-6-fluorobenzyl)amino)-2,3-difluoro-N-(isothiazol-3-yl)benzenesulfonamide;
as an individual stereoisomer, enantiomer or tautomer thereof or a mixture thereof; or a pharmaceutically acceptable salt or solvate thereof.

5. The compound of claim 2, as an individual stereoisomer, enantiomer or tautomer thereof or a mixture thereof; or a pharmaceutically acceptable salt or solvate thereof, wherein $R^2$ is thiazolyl.

6. The compound of claim 5, as an individual stereoisomer, enantiomer or tautomer thereof or a mixture thereof; or a pharmaceutically acceptable salt or solvate thereof, wherein r is 1.

7. The compound of claim 6 selected from:
4-((2-((7-azabicyclo[2.2.1]heptan-7-yl)methyl)-6-fluorobenzyl)amino)-2,3-difluoro-N-(thiazol-4-yl)benzenesulfonamide;
4-((2-((7-azabicyclo[2.2.1]heptan-7-yl)methyl)-6-fluorobenzyl)amino)-3-chloro-2-fluoro-N-(thiazol-4-yl)benzenesulfonamide;
4-((2-((7-azabicyclo[2.2.1]heptan-7-yl)methyl)-6-fluorobenzyl)amino)-2-fluoro-3-methyl-N-(thiazol-4-yl)benzenesulfonamide; and
4-((2-((7-azabicyclo[2.2.1]heptan-7-yl)methyl)-6-fluorobenzyl)amino)-2,6-difluoro-N-(thiazol-4-yl)benzenesulfonamide;
as an individual stereoisomer, enantiomer or tautomer thereof or a mixture thereof; or a pharmaceutically acceptable salt or solvate thereof.

8. The compound of claim 5, as an individual stereoisomer, enantiomer or tautomer thereof or a mixture thereof; or a pharmaceutically acceptable salt or solvate thereof, where r is 2.

9. The compound of claim 8 selected from:
4-((2-((7-azabicyclo[2.2.1]heptan-7-yl)methyl)-3,6-difluorobenzyl)amino)-2,6-difluoro-N-(thiazol-4-yl)benzenesulfonamide;
4-((2-((7-azabicyclo[2.2.1]heptan-7-yl)methyl)-6-fluoro-3-methoxybenzyl)amino)-2,6-difluoro-N-(thiazol-4-yl)benzenesulfonamide;
4-((2-((7-azabicyclo[2.2.1]heptan-7-yl)methyl)-6-fluoro-3-methoxybenzyl)amino)-2,3-difluoro-N-(thiazol-4-yl)benzenesulfonamide;
54-((2-(1-(7-azabicyclo[2.2.1]heptan-7-yl)ethyl)-3,6-difluorobenzyl)amino)-2,6-difluoro-N-(thiazol-4-yl)benzenesulfonamide;
(S)-4-((2-(1-(7-azabicyclo[2.2.1]heptan-7-yl)ethyl)-3,6-difluorobenzyl)amino)-2,6-difluoro-N-(thiazol-4-yl)benzenesulfonamide; and
(R)-4-((2-(1-(7-azabicyclo[2.2.1]heptan-7-yl)ethyl)-3,6-difluorobenzyl)amino)-2,6-difluoro-N-(thiazol-4-yl)benzenesulfonamide;
as an individual stereoisomer, enantiomer or tautomer thereof or a mixture thereof; or a pharmaceutically acceptable salt or solvate thereof.

10. The compound of claim 2, as an individual stereoisomer, enantiomer or tautomer thereof or a mixture thereof; or a pharmaceutically acceptable salt or solvate thereof, wherein $R^2$ is isoxazolyl.

11. The compound of claim 10 selected from:
4-((2-((7-azabicyclo[2.2.1]heptan-7-yl)methyl)-6-fluorobenzyl)amino)-2,6-difluoro-N-(isoxazol-3-yl)-3-methylbenzenesulfonamide; and
4-((2-((7-azabicyclo[2.2.1]heptan-7-yl)methyl)-6-fluorobenzyl)amino)-2-fluoro-N-(isoxazol-3-yl)-3-methylbenzenesulfonamide;
as an individual stereoisomer, enantiomer or tautomer thereof or a mixture thereof; or a pharmaceutically acceptable salt or solvate thereof.

12. The compound of claim 1, as an individual stereoisomer, enantiomer or tautomer thereof or a mixture thereof; or a pharmaceutically acceptable salt or solvate thereof, where $R^7$ is ((methyl)(prop-2-yl)amino)alkyl, provided that r is 2 and at least one $R^6$ is alkoxy.

13. The compound of claim 12, as an individual stereoisomer, enantiomer or tautomer thereof or a mixture thereof; or a pharmaceutically acceptable salt or solvate thereof, wherein $R^2$ is isothiazolyl.

14. The compound of claim 12, as an individual stereoisomer, enantiomer or tautomer thereof or a mixture thereof; or a pharmaceutically acceptable salt or solvate thereof, wherein $R^2$ is thiazolyl.

15. The compound of claim 14 selected from:
2,6-difluoro-4-((6-fluoro-2-((isopropyl(methyl)amino)methyl)-3-methoxybenzyl)amino)-N-(thiazol-4-yl)benzenesulfonamide;
2,6-difluoro-4-((6-fluoro-3-isopropoxy-2-((isopropyl(methyl)amino)methyl)benzyl)amino)-N-(thiazol-4-yl)benzenesulfonamide;
2,3-difluoro-4-((6-fluoro-2-((isopropyl(methyl)amino)methyl)-3-methoxybenzyl)amino)-N-(thiazol-4-yl)benzenesulfonamide;
5-chloro-2-fluoro-4-((6-fluoro-2-((isopropyl(methyl)amino)methyl)-3-methoxybenzyl)amino)-N-(thiazol-4-yl)benzenesulfonamide; and
2-fluoro-4-((6-fluoro-2-((isopropyl(methyl)amino)methyl)-3-methoxybenzyl)amino)-5-methyl-N-(thiazol-4-yl)benzenesulfonamide;
as an individual stereoisomer, enantiomer or tautomer thereof or a mixture thereof; or a pharmaceutically acceptable salt or solvate thereof.

16. The compound of claim 12, as an individual stereoisomer, enantiomer or tautomer thereof or a mixture thereof, or a pharmaceutically acceptable salt or solvate thereof, wherein $R^2$ is isoxazolyl.

17. A pharmaceutical composition comprising a pharmaceutically acceptable excipient and a compound of claim 1, as a stereoisomer, enantiomer or tautomer thereof or a mixture thereof; or a pharmaceutically acceptable salt or solvate thereof.

18. The compound of claim 1, which is 4-((2-((7-azabicyclo[2.2.1]heptan-7-yl)methyl)-6-fluorobenzyl)amino)-2,6-difluoro-N-(isothiazol-3-yl)benzenesulfonamide, as an individual stereoisomer, enantiomer or tautomer thereof or a mixture thereof; or a pharmaceutically acceptable salt or solvate thereof.

19. The compound of claim 1, which is 2,6-difluoro-4-((6-fluoro-2-((isopropyl(methyl)amino)methyl)-3-methoxybenzyl)amino)-N-(thiazol-4-yl)benzenesulfonamide, as an individual stereoisomer, enantiomer or tautomer thereof or a mixture thereof; or a pharmaceutically acceptable salt or solvate thereof.

20. The compound of claim 1, which is 4-((2-((7-azabicyclo[2.2.1]heptan-7-yl)methyl)-6-fluorobenzyl)amino)-2,3-difluoro-N-(thiazol-4-yl)benzenesulfonamide, as an individual stereoisomer, enantiomer or tautomer thereof or a mixture thereof; or a pharmaceutically acceptable salt or solvate thereof.

21. The compound of claim 1, which is 4-((2-((7-azabicyclo[2.2.1]heptan-7-yl)methyl)-6-fluorobenzyl)amino)-2,6-difluoro-N-(isoxazol-3-yl)-3-methylbenzenesulfonamide, as an individual stereoisomer, enantiomer or tautomer thereof or a mixture thereof; or a pharmaceutically acceptable salt or solvate thereof.

22. The compound of claim 1, which is 4-((2-((7-azabicyclo[2.2.1]heptan-7-yl)methyl)-6-fluorobenzyl)amino)-2-fluoro-N-(isoxazol-3-yl)-3-methylbenzenesulfonamide, as an individual stereoisomer, enantiomer or tautomer thereof or a mixture thereof; or a pharmaceutically acceptable salt or solvate thereof.

23. The compound of claim 1, which is 4-((2-((7-azabicyclo[2.2.1]heptan-7-yl)methyl)-6-fluorobenzyl)amino)-2-fluoro-3-methyl-N-(thiazol-4-yl)benzenesulfonamide, as an individual stereoisomer, enantiomer or tautomer thereof or a mixture thereof; or a pharmaceutically acceptable salt or solvate thereof.

24. The compound of claim 1, which is 4-((2-((7-azabicyclo[2.2.1]heptan-7-yl)methyl)-6-fluoro-3-methoxybenzyl)amino)-2,6-difluoro-N-(thiazol-4-yl)benzenesulfonamide, as an individual stereoisomer, enantiomer or tautomer thereof or a mixture thereof; or a pharmaceutically acceptable salt or solvate thereof.

25. The compound of claim 1, which is 4-((2-((7-azabicyclo[2.2.1]heptan-7-yl)methyl)-6-fluoro-3-methoxybenzyl)amino)-2,3-difluoro-N-(thiazol-4-yl)benzenesulfonamide, as an individual stereoisomer, enantiomer or tautomer thereof or a mixture thereof; or a pharmaceutically acceptable salt or solvate thereof.

26. The compound of claim 1, which is 4-((2-((7-azabicyclo[2.2.1]heptan-7-yl)methyl)-6-fluorobenzyl)amino)-2,3-difluoro-N-(isothiazol-3-yl)benzenesulfonamide, as an individual stereoisomer, enantiomer or tautomer thereof or a mixture thereof; or a pharmaceutically acceptable salt or solvate thereof.

27. The compound of claim 1, which is 2-fluoro-4-((6-fluoro-2-((isopropyl(methyl)amino)methyl)-3-methoxybenzyl)amino)-5-methyl-N-(thiazol-4-yl)benzenesulfonamide, as an individual stereoisomer, enantiomer or tautomer thereof or a mixture thereof; or a pharmaceutically acceptable salt or solvate thereof.

28. The compound of claim 1, which is 4-((2-((7-azabicyclo[2.2.1]heptan-7-yl)methyl)-6-fluorobenzyl)amino)-2,6-difluoro-N-(isothiazol-3-yl) benzenesulfonamide, or a pharmaceutically acceptable salt or solvate thereof.

29. The compound of claim 1, which is 4-((2-((7-azabicyclo[2.2.1]heptan-7-yl)methyl)-6-fluorobenzyl)amino)-2,6-difluoro-N-(isothiazol-3-yl) benzenesulfonamide.

30. The compound of claim 1, which is 2,6-difluoro-4-((6-fluoro-2-((isopropyl(methyl)amino)methyl)-3-methoxybenzyl)amino)-N-(thiazol-4-yl) benzenesulfonamide, or a pharmaceutically acceptable salt or solvate thereof.

31. The compound of claim 1, which is 2,6-difluoro-4-((6-fluoro-2-((isopropyl(methyl)amino)methyl)-3-methoxybenzyl)amino)-N-(thiazol-4-yl)benzenesulfonamide.

32. The compound of claim 1, which is 4-((2((7-azabicyclo[2.2.1]heptan-7-yl)methyl)-6-fluorobenzyl)amino)-2,3-difluoro-N-(thiazol-4-yl) benzenesulfonamide, or a pharmaceutically acceptable salt or solvate thereof.

33. The compound of claim 1, which is 4-((2-((7-azabi-cyclo[2.2.1]heptan-7-yl)methyl)-6-fluorobenzyl)amino)-2,3-difluoro-N-(thiazol-4-yl) benzenesulfonamide.

34. The compound of claim 1, which is 4-((2-((7-azabi-cyclo[2.2.1]heptan-7-yl)methyl)-6-fluorobenzyl)amino)-2,6-difluoro-N-(isoxazol-3 -yl)-3 -methylbenzenesulfona-mide, or a pharmaceutically acceptable salt or solvate thereof.

35. The compound of claim 1, which is 4-((2-((7-azabi-cyclo[2.2.1]heptan-7-yl)methyl)-6-fluorobenzyl)amino)-2,6-difluoro-N-(isoxazol-3-yl)-3-methylbenzenesulfonamide.

36. The compound of claim 1, which is 4-((2-((7-azabi-cyclo[2.2.1]heptan-7-yl)methyl)-6-fluorobenzyl)amino)-2-fluoro-N-(isoxazol-3-yl)-3-methylbenzenesulfonamide, or a pharmaceutically acceptable salt or solvate thereof.

37. The compound of claim 1, which is 4-((2-((7-azabi-cyclo[2.2.1]heptan-7-yl)methyl)-6-fluorobenzyl)amino)-2-fluoro-N-(isoxazol-3-yl)-3-methylbenzenesulfonamide.

38. The compound of claim 1, which is 4-((2-((7-azabi-cyclo[2.2.1]heptan-7-yl)methyl)-6-fluorobenzyl)amino)-2-fluoro-3-methyl-N-(thiazol-4-yl)benzenesulfonamide, or a pharmaceutically acceptable salt or solvate thereof.

39. The compound of claim 1, which is 4-((2-((7-azabi-cyclo[2.2.1]heptan-7-yl)methyl)-6-fluorobenzyl)amino)-2-fluoro-3-methyl-N-(thiazol-4-yl)benzenesulfonamide.

40. The compound of claim 1, which is 4-((2-((7-azabi-cyclo[2.2.1]heptan-7-yl)methyl)-6-fluoro-3 -methoxyben-zyl)amino)-2, 6-difluoro-N-(thiazol-4-yl)benzenesulfona-mide, or a pharmaceutically acceptable salt or solvate thereof.

41. The compound of claim 1, which is 4-((2-((7-azabi-cyclo[2.2.1]heptan-7-yl)methyl)-6-fluoro-3-methoxyben-zyl)amino)-2,6-difluoro-N-(thiazol-4-yl)benzenesulfona-mide.

42. The compound of claim 1, which is 4-((2-((7-azabi-cyclo[2.2.1]heptan-7-yl)methyl)-6-fluoro-3-methoxyben-zyl)amino)-2,3-difluoro-N-(thiazol-4-yl)benzenesulfona-mide, or a pharmaceutically acceptable salt or solvate thereof.

43. The compound of claim 1, which is 4-((2-((7-azabi-cyclo[2.2.1]heptan-7-yl)methyl)-6-fluoro-3-methoxyben-zyl)amino)-2,3-difluoro-N-(thiazol-4-yl)benzenesulfona-mide.

44. The compound of claim 1, which is 4-((2-((-azabicy-clo[2.2.1]heptan-7-yl)methyl)-6-fluorobenzyl)amino)-2,3-difluoro-N-(isothiazol-3-yl)benzenesulfonamide, or a phar-maceutically acceptable salt or solvate thereof.

45. The compound of claim 1, which is 4-((2((7-azabi-cyclo[2.2.1]heptan-7-yl)methyl)-6-fluorobenzyl)amino)-2,3-difluoro-N-(isothiazol-3-yl)benzenesulfonamide.

46. The compound of claim 1, which is 2-fluoro-4-((6-fluoro-2-((isopropyl(methyl)amino) methyl)-3 -methoxy-benzyl)amino)-5 -methyl-N-(thiazol-4-yl)benzenesulfona-mide, or a pharmaceutically acceptable salt or solvate thereof.

47. The compound of claim 1, which is 2-fluoro-4-((6-fluoro-2-((isopropyl(methyl)amino) methyl)-3 -methoxy-benzyl)amino)-5 -methyl-N-(thiazol-4-yl)benzenesulfona-mide.

\* \* \* \* \*

UNITED STATES PATENT AND TRADEMARK OFFICE
CERTIFICATE OF CORRECTION

PATENT NO. : 10,745,392 B2
APPLICATION NO. : 16/440459
DATED : August 18, 2020
INVENTOR(S) : Kristen Nicole Burford et al.

It is certified that error appears in the above-identified patent and that said Letters Patent is hereby corrected as shown below:

In the Claims

Column 99, Line 45, Claim 16, delete "thereof," and insert -- thereof; --.

Column 100, Line 64, Claim 32, delete "4-((2((7" and insert -- 4-((2-((7 --.

Column 100, Line 66, Claim 32, delete "(thiazol-4-yl) benzenesulfonamide." and insert -- "(thiazol-4-yl)benzenesulfonamide." --.

Column 101, Line 3, Claim 33, delete "(thiazol-4-yl) benzenesulfonamide." and insert -- "(thiazol-4-yl)benzenesulfonamide." --.

Column 102, Line 14, Claim 44, delete "4-(2-((-azabicy-" and insert -- 4-((2-((7-azabicy- --.

Column 102, Line 18, Claim 45, delete "4-((2((7" and insert -- 4-((2-((7 --.

Signed and Sealed this
Eleventh Day of November, 2025

John A. Squires
*Director of the United States Patent and Trademark Office*